United States Patent
Barrett et al.

(10) Patent No.: US 10,059,763 B2
(45) Date of Patent: Aug. 28, 2018

(54) COMPOUND TARGETING IL-23A AND TNF-ALPHA AND USES THEREOF

(71) Applicants: Boehringer Ingelheim International GmbH, Ingelheim am Rhein (DE); MacroGenics, Inc., Rockville, MD (US)

(72) Inventors: Rachel Rebecca Barrett, Bethel, CT (US); Leslie S. Johnson, Darnestown, MD (US); Sanjaya Singh, Sandy Hook, CT (US); Kathleen Last-Barney, Ridgefield, CT (US); Daw-Tsun Shih, Ridgefield, CT (US); Patricia Giblin, Ridgefield, CT (US); Scott Brodeur, Ridgefield, CT (US); Nelamangala Nagaraja, Ridgefield, CT (US)

(73) Assignees: BOEHRINGER INGELHEIM INTERNATIONAL GMBH, Ingelheim am Rhein (DE); MACROGENICS, INC., Rockville, MD (US)

( * ) Notice: Subject to any disclaimer, the term of this patent is extended or adjusted under 35 U.S.C. 154(b) by 0 days.

(21) Appl. No.: 14/844,338

(22) Filed: Sep. 3, 2015

(65) Prior Publication Data
US 2016/0060338 A1    Mar. 3, 2016

Related U.S. Application Data

(60) Provisional application No. 62/045,498, filed on Sep. 3, 2014.

(51) Int. Cl.
| | |
|---|---|
| *C07K 16/24* | (2006.01) |
| *C07K 16/18* | (2006.01) |
| *A61K 39/395* | (2006.01) |
| *A61K 38/23* | (2006.01) |
| *A61K 31/59* | (2006.01) |
| *G01N 33/574* | (2006.01) |
| *C12N 5/0783* | (2010.01) |
| *A61K 39/00* | (2006.01) |

(52) U.S. Cl.
CPC .......... *C07K 16/244* (2013.01); *C07K 16/241* (2013.01); *A61K 39/3955* (2013.01); *A61K 2039/505* (2013.01); *C07K 2317/31* (2013.01); *C07K 2317/76* (2013.01); *C07K 2317/92* (2013.01); *C07K 2317/94* (2013.01); *C12N 5/0638* (2013.01); *G01N 33/574* (2013.01)

(58) Field of Classification Search
None
See application file for complete search history.

(56) References Cited

U.S. PATENT DOCUMENTS

| | | |
|---|---|---|
| 5,624,821 A | 4/1997 | Winter et al. |
| 5,648,260 A | 7/1997 | Winter et al. |
| 6,060,284 A | 5/2000 | Bazan |
| 6,277,375 B1 | 8/2001 | Ward |
| 6,479,634 B1 | 11/2002 | Bazan |
| 6,492,123 B1 | 12/2002 | Holliger et al. |
| 6,495,667 B1 | 12/2002 | Bazan |
| 6,610,285 B1 | 8/2003 | Hirata |
| 6,623,940 B1 | 9/2003 | Ledbetter et al. |
| 6,756,481 B2 | 6/2004 | Chirica et al. |
| 6,821,505 B2 | 11/2004 | Ward |
| 6,835,825 B1 | 12/2004 | Bazan |
| 6,875,741 B2 | 4/2005 | Pillutla et al. |
| 7,090,847 B1 | 8/2006 | Oppmann et al. |
| 7,122,646 B2 | 10/2006 | Holliger et al. |
| 7,183,382 B2 | 2/2007 | Oppmann et al. |
| 7,252,967 B2 | 8/2007 | Hirata |
| 7,282,204 B2 | 10/2007 | Oft et al. |
| 7,332,156 B2 | 2/2008 | Bowman et al. |
| 7,411,041 B2 | 8/2008 | Chirica et al. |
| 7,422,743 B2 | 9/2008 | Chirica et al. |
| 7,427,402 B2 | 9/2008 | Kastelein et al. |
| 7,491,391 B2 | 2/2009 | Benson et al. |
| 7,501,247 B2 | 3/2009 | Kastelein et al. |
| 7,510,709 B2 | 3/2009 | Gurney |
| 7,510,853 B2 | 3/2009 | Chirica et al. |
| 7,575,741 B2 | 8/2009 | Bowman et al. |
| 7,608,690 B2 | 10/2009 | Bazan |
| 7,740,848 B2 | 6/2010 | Kastelein et al. |
| 7,749,718 B2 | 7/2010 | Chirica et al. |
| 7,750,126 B2 | 7/2010 | Hirata |
| 7,754,214 B2 | 7/2010 | Chirica et al. |
| 7,790,862 B2 | 9/2010 | Lewis et al. |
| 7,807,160 B2 | 10/2010 | Presta et al. |

(Continued)

FOREIGN PATENT DOCUMENTS

| | | |
|---|---|---|
| EP | 1 072 610 A1 | 1/2001 |
| EP | 1072610 | 1/2001 |

(Continued)

OTHER PUBLICATIONS

[No Author Listed] Anti-human IL-23 p. 19 Antibody. Catalog No. AF1716. R&D Systems, Inc. Dated Dec. 17, 2003. 1 page.
[No Author Listed] Anti-Mouse IL-23 p. 19 Purified. Catalog No. 14-7232. eBioscience. 2005. 2 pages.
[No Author Listed] Anti-Mouse IL-23 p. 19 Purified. Catalog No. 14-7233. eBioscience. 2007. 1 page.
[No Author Listed] Mouse IL-23 ELISA Ready-Set-Go! ELISA Kit . Catalog No. 88-7923. eBioscience. 2007. 6 pages.
[No Author Listed] New Products from R&D Systems. De Novo Catalogue. Mar. 2004. 10 pgs.

(Continued)

*Primary Examiner* — Bridget E Bunner
*Assistant Examiner* — Fozia Hamud
(74) *Attorney, Agent, or Firm* — Robin L. Teskin; LeClairRyan PLLC

(57) ABSTRACT

The disclosure relates to compounds specific for IL23A and TNF-alpha, compositions comprising the compounds, and methods of use thereof. Nucleic acids, cells, and methods of production related to the compounds and compositions are also disclosed.

23 Claims, 5 Drawing Sheets
Specification includes a Sequence Listing.

(56) References Cited

U.S. PATENT DOCUMENTS

| | | |
|---|---|---|
| 7,807,414 B2 | 10/2010 | Benson et al. |
| 7,820,168 B2 | 10/2010 | Cua et al. |
| 7,872,102 B2 | 1/2011 | Beidler et al. |
| 7,883,695 B2 | 2/2011 | Oppmann et al. |
| 7,887,806 B2 | 2/2011 | Chirica et al. |
| 7,893,215 B2 | 2/2011 | Bowman et al. |
| 7,910,703 B2 | 3/2011 | Lewis et al. |
| 7,935,344 B2 | 5/2011 | Benson et al. |
| 7,993,645 B2 | 8/2011 | Benson et al. |
| 8,106,177 B2 | 1/2012 | Benson et al. |
| 8,772,459 B2 | 7/2014 | Ho et al. |
| 8,778,346 B2 | 7/2014 | Barrett et al. |
| 9,284,375 B2 | 3/2016 | Johnson et al. |
| 9,296,816 B2 | 3/2016 | Johnson et al. |
| 9,376,495 B2 | 6/2016 | Bonvini et al. |
| 9,441,036 B2 | 9/2016 | Barrett et al. |
| 2003/0092059 A1 | 5/2003 | Salfeld et al. |
| 2004/0058400 A1 | 3/2004 | Holliger et al. |
| 2004/0219150 A1 | 11/2004 | Cua et al. |
| 2004/0220388 A1 | 11/2004 | Mertens et al. |
| 2004/0258686 A1 | 12/2004 | Chirica et al. |
| 2005/0039222 A1 | 2/2005 | Habu et al. |
| 2005/0100917 A1 | 5/2005 | Chirica et al. |
| 2005/0100918 A1 | 5/2005 | Chirica et al. |
| 2005/0100965 A1 | 5/2005 | Ghayur et al. |
| 2005/0208052 A1 | 9/2005 | Katsikis et al. |
| 2005/0244874 A1 | 11/2005 | Kastelein et al. |
| 2005/0287593 A1 | 12/2005 | Kastelein et al. |
| 2006/0088523 A1 | 4/2006 | Andya et al. |
| 2006/0140958 A1 | 6/2006 | Hogan et al. |
| 2007/0004909 A1 | 1/2007 | Johnson et al. |
| 2007/0009526 A1 | 1/2007 | Benson et al. |
| 2008/0085277 A1 | 4/2008 | Cho et al. |
| 2008/0199460 A1 | 8/2008 | Cua et al. |
| 2008/0200655 A1 | 8/2008 | Sek |
| 2008/0254026 A1 | 10/2008 | Long et al. |
| 2009/0041770 A1 | 2/2009 | Chamberlain et al. |
| 2009/0060906 A1 | 3/2009 | Barry et al. |
| 2009/0060910 A1 | 3/2009 | Johnson et al. |
| 2009/0092604 A1 | 4/2009 | Cua et al. |
| 2009/0123479 A1 | 5/2009 | Bembridge et al. |
| 2009/0156788 A1 | 6/2009 | Presta et al. |
| 2009/0291062 A1 | 11/2009 | Fraunhofer et al. |
| 2010/0003251 A1 | 1/2010 | Oft et al. |
| 2010/0041144 A1 | 2/2010 | Bazan |
| 2010/0111950 A1 | 5/2010 | Cua et al. |
| 2010/0111954 A1 | 5/2010 | Cua et al. |
| 2010/0111966 A1 | 5/2010 | Presta et al. |
| 2010/0135998 A1 | 6/2010 | Bowman et al. |
| 2010/0143357 A1 | 6/2010 | Cua et al. |
| 2010/0174053 A1 | 7/2010 | Johnson et al. |
| 2010/0254991 A1 | 10/2010 | Kastelein et al. |
| 2010/0261273 A1 | 10/2010 | Chirica et al. |
| 2010/0266582 A1 | 10/2010 | Gurney |
| 2010/0266583 A1 | 10/2010 | Gurney |
| 2010/0272731 A1 | 10/2010 | Presta et al. |
| 2010/0291084 A1 | 11/2010 | Kopf et al. |
| 2010/0322863 A1 | 12/2010 | Benson et al. |
| 2011/0002942 A1 | 1/2011 | Presta et al. |
| 2011/0059087 A1 | 3/2011 | Lewis et al. |
| 2011/0110852 A1 | 5/2011 | Miller et al. |
| 2011/0135597 A1 | 6/2011 | Bowman et al. |
| 2011/0142831 A1 | 6/2011 | Cua et al. |
| 2011/0142853 A1 | 6/2011 | Presta et al. |
| 2011/0159589 A1 | 6/2011 | Lewis et al. |
| 2011/0177022 A1 | 7/2011 | Oppmann et al. |
| 2011/0195455 A1 | 8/2011 | Benson et al. |
| 2011/0206686 A1 | 8/2011 | Bembridge et al. |
| 2011/0229490 A1 | 9/2011 | Li et al. |
| 2011/0250201 A1 | 10/2011 | Smith |
| 2011/0268656 A1 | 11/2011 | Ho et al. |
| 2011/0287032 A1 | 11/2011 | Lazar et al. |
| 2011/0311527 A1 | 12/2011 | Stern et al. |
| 2012/0076800 A1 | 3/2012 | Dai et al. |
| 2012/0128689 A1 | 5/2012 | Clarkson et al. |
| 2012/0195885 A1 | 8/2012 | Correia et al. |
| 2012/0251541 A1 | 10/2012 | Baurin et al. |
| 2012/0277799 A1 | 11/2012 | Winslow et al. |
| 2012/0282269 A1 | 11/2012 | Barrett et al. |
| 2012/0283418 A1 | 11/2012 | Wu et al. |
| 2013/0004501 A1 | 1/2013 | Towne et al. |
| 2013/0028907 A1 | 1/2013 | Parshad et al. |
| 2013/0078249 A1 | 3/2013 | Ast et al. |
| 2013/0115166 A1 | 5/2013 | Clarke et al. |
| 2013/0216525 A1 | 8/2013 | Chen |
| 2013/0287775 A1 | 10/2013 | Bowman et al. |
| 2013/0295121 A1 | 11/2013 | Johnson et al. |
| 2014/0178401 A1 | 6/2014 | Nabozny et al. |
| 2014/0213772 A1 | 7/2014 | Ghayur et al. |
| 2014/0303357 A1 | 10/2014 | Lim et al. |
| 2014/0363444 A1 | 12/2014 | Barrett et al. |
| 2015/0175697 A1 | 6/2015 | Bonvini |
| 2016/0222102 A1 | 8/2016 | Arndt et al. |
| 2016/0333091 A1 | 11/2016 | Barrett et al. |

FOREIGN PATENT DOCUMENTS

| | | |
|---|---|---|
| EP | 1354600 A1 | 10/2003 |
| WO | 1988007089 | 9/1988 |
| WO | 1997034631 | 9/1997 |
| WO | 1997044362 | 11/1997 |
| WO | 1998005787 | 2/1998 |
| WO | WO 99/05280 A1 | 2/1999 |
| WO | WO 9905280 | 2/1999 |
| WO | WO 99/40195 A1 | 8/1999 |
| WO | WO 9940195 | 8/1999 |
| WO | 1999051642 | 10/1999 |
| WO | 1999058572 | 10/1999 |
| WO | WO 99/54357 A1 | 10/1999 |
| WO | WO 9954357 | 10/1999 |
| WO | WO 2000/006605 A2 | 2/2000 |
| WO | WO 200006605 | 2/2000 |
| WO | WO 2001/018051 A2 | 3/2001 |
| WO | WO 2001018051 | 3/2001 |
| WO | WO 2001/085790 A2 | 11/2001 |
| WO | WO 2001085790 | 11/2001 |
| WO | 2002002781 | 1/2002 |
| WO | 2002060919 | 8/2002 |
| WO | WO 2003/039485 A2 | 5/2003 |
| WO | WO 2003039485 | 5/2003 |
| WO | WO 2004016286 | 2/2004 |
| WO | WO 2004/042009 A2 | 5/2004 |
| WO | WO 2004042009 | 5/2004 |
| WO | WO 2004/058178 A2 | 7/2004 |
| WO | WO 2004058178 | 7/2004 |
| WO | WO 2004/071517 A2 | 8/2004 |
| WO | WO 2004071517 | 8/2004 |
| WO | WO 2004/081190 A2 | 9/2004 |
| WO | WO 2004081190 | 9/2004 |
| WO | WO 2005/044294 A2 | 5/2005 |
| WO | WO 2005044294 | 5/2005 |
| WO | WO 2005/052157 A1 | 6/2005 |
| WO | WO 2005052157 | 6/2005 |
| WO | WO 2005/079837 A1 | 9/2005 |
| WO | WO 2005079837 | 9/2005 |
| WO | WO 2005/108616 A1 | 11/2005 |
| WO | WO 2005108616 | 11/2005 |
| WO | WO 2006/036922 A2 | 4/2006 |
| WO | WO 2006036922 | 4/2006 |
| WO | WO 2006/068987 A2 | 6/2006 |
| WO | WO 2006068987 | 6/2006 |
| WO | 2006113665 | 10/2006 |
| WO | WO 2007/005647 A2 | 1/2007 |
| WO | WO 2007/005955 A2 | 1/2007 |
| WO | WO 2007005647 | 1/2007 |
| WO | WO 2007005955 | 1/2007 |
| WO | WO 2007/024846 A2 | 3/2007 |
| WO | WO 2007/027714 A2 | 3/2007 |
| WO | WO 2007/027761 A2 | 3/2007 |
| WO | WO 2007024846 | 3/2007 |
| WO | WO 2007027714 | 3/2007 |
| WO | WO 2007027761 | 3/2007 |
| WO | WO 2007/076524 A2 | 7/2007 |
| WO | WO 2007076523 | 7/2007 |

(56) References Cited

FOREIGN PATENT DOCUMENTS

| WO | WO 2007076524 | 7/2007 |
|---|---|---|
| WO | WO 2007/147019 A2 | 12/2007 |
| WO | WO 2007/149814 A1 | 12/2007 |
| WO | WO 2007147019 | 12/2007 |
| WO | WO 2007149814 | 12/2007 |
| WO | WO 2008/103432 A1 | 8/2008 |
| WO | WO 2008/103473 A1 | 8/2008 |
| WO | WO 2008103432 | 8/2008 |
| WO | WO 2008103473 | 8/2008 |
| WO | WO 2008/106131 A2 | 9/2008 |
| WO | WO 2008106131 | 9/2008 |
| WO | 2008157379 | 12/2008 |
| WO | WO 2008/153610 A2 | 12/2008 |
| WO | WO 2008153610 | 12/2008 |
| WO | WO 2009/032954 A1 | 3/2009 |
| WO | WO 2009032954 | 3/2009 |
| WO | WO 2009/043933 A1 | 4/2009 |
| WO | WO 2009043933 | 4/2009 |
| WO | WO 2009053493 | 4/2009 |
| WO | WO 2009/055936 A1 | 5/2009 |
| WO | WO 2009055936 | 5/2009 |
| WO | WO 2009073569 | 6/2009 |
| WO | WO 2009/082624 A2 | 7/2009 |
| WO | WO 2009082624 | 7/2009 |
| WO | WO 2010017598 | 2/2010 |
| WO | WO 2010017598 A1 | 2/2010 |
| WO | WO 2010/027766 A1 | 3/2010 |
| WO | WO 2010027766 | 3/2010 |
| WO | 2010080538 | 7/2010 |
| WO | WO 2010/115092 A2 | 10/2010 |
| WO | WO 2010/115786 A1 | 10/2010 |
| WO | WO 2010115092 | 10/2010 |
| WO | WO 2010115786 | 10/2010 |
| WO | WO 2011/011797 A2 | 1/2011 |
| WO | WO 2011011797 | 1/2011 |
| WO | WO 2011/056600 A1 | 5/2011 |
| WO | WO 2011056600 | 5/2011 |
| WO | 2011/066501 | 6/2011 |
| WO | WO 2011/066369 A2 | 6/2011 |
| WO | WO 2011066369 | 6/2011 |
| WO | WO 2011/070339 A1 | 6/2011 |
| WO | WO 2011070339 | 6/2011 |
| WO | WO 2011/103105 A1 | 8/2011 |
| WO | WO 2011103105 | 8/2011 |
| WO | WO 2011104381 | 9/2011 |
| WO | WO 2011109365 | 9/2011 |
| WO | WO 2011/159655 A2 | 12/2011 |
| WO | WO 2011159655 | 12/2011 |
| WO | WO 2011159750 | 12/2011 |
| WO | WO 2012/009760 A1 | 1/2012 |
| WO | WO 2012009760 | 1/2012 |
| WO | 2012018687 | 2/2012 |
| WO | WO 2012/032181 A2 | 3/2012 |
| WO | WO 2012032181 | 3/2012 |
| WO | WO 2012/061448 A1 | 5/2012 |
| WO | WO 2012061448 | 5/2012 |
| WO | WO 2012093254 | 7/2012 |
| WO | WO 2012103345 | 8/2012 |
| WO | 2012162068 | 11/2012 |
| WO | WO 2013/070565 A1 | 5/2013 |
| WO | WO 2013070565 | 5/2013 |
| WO | WO 2013/165791 A1 | 11/2013 |
| WO | WO 2013165791 | 11/2013 |
| WO | WO 2014004436 | 1/2014 |
| WO | WO 2014143540 | 9/2014 |
| WO | WO 2014149425 | 9/2014 |
| WO | 2786746 | 10/2014 |

OTHER PUBLICATIONS

[No Author Listed] R&D Systems: new products. Jun. 2005. 12 pages.

Aggarwal et al., Interleukin-23 promotes a distinct CD4 T cell activation state characterized by the production of interleukin-17. J Biol Chem. Jan. 17, 2003;278(3):1910-4. Epub Nov. 3, 2002.

Alegre et al., A non-activating "humanized" anti-CD3 monoclonal antibody retains immunosuppressive properties in vivo. Transplantation. Jun. 15, 1994;57(11):1537-43.

Beyer et al., Crystal structures of the pro-inflammatory cytokine interleukin-23 and its complex with a high-affinity neutralizing antibody. J Mol Biol. Oct. 17, 2008;382(4):942-55. doi: 10.1016/j.jmb.2008.08.001. Epub Aug. 7, 2008.

Chan et al., Therapeutic antibodies for autoimmunity and inflammation. Nat Rev Immunol. May 2010;10(5):301-16. doi: 10.1038/nri2761. Review.

Fichtner-Feigl et al., Treatment of murine Th1- and Th2-mediated inflammatory bowel disease with NF-kappa B decoy oligonucleotides. J Clin Invest. Nov 2005;115(11):3057-71. Epub Oct. 20, 2005.

Happel et al., Divergent roles of IL-23 and IL-12 in host defense against Klebsiella pneumoniae. J Exp Med. Sep. 19, 2005;202(6):761-9. Epub Sep. 12, 2005.

Hegazi et al., Carbon monoxide ameliorates chronic murine colitis through a heme oxygenase 1-dependent pathway. J Exp Med. Dec. 19, 2005;202(12):1703-13.

Hoeve et al., IL-12 receptor deficiency revisited: IL-23-mediated signaling is also impaired in human genetic IL-12 receptor beta1 deficiency. Eur J Immunol. Dec. 2003;33(12):3393-7.

Kastelein et al., Discovery and biology of IL-23 and IL-27: related but functionally distinct regulators of inflammation. Annu Rev Immunol. 2007;25:221-42. Review.

Kidoya et al., Fas ligand induces cell-autonomous IL-23 production in dendritic cells, a mechanism for Fas ligand-induced IL-17 production. J Immunol. Dec. 15, 2005;175(12):8024-31.

Kikly et al., The IL-23/Th(17) axis: therapeutic targets for autoimmune inflammation. Curr Opin Immunol. Dec. 2006;18(6):670-5. Epub Sep. 28, 2006. Review. Erratum in: Curr Opin Immunol. Feb. 2007;19(1):111.

Kuwashima et al., Delivery of dendritic cells engineered to secrete IFN-alpha into central nervous system tumors enhances the efficacy of peripheral tumor cell vaccines: dependence on apoptotic pathways. J Immunol. Aug. 15, 2005;175(4):2730-40.

Lee et al., Increased expression of interleukin 23 p. 19 and p. 40 in lesional skin of patients with psoriasis vulgaris. J Exp Med. Jan. 5, 2004;199(1):125-30.

Morelli et al., CD4+ T cell responses elicited by different subsets of human skin migratory dendritic cells. J Immunol. Dec. 15, 2005;175(12):7905-15.

Oppmann et al., Novel p. 19 protein engages IL-12 p. 40 to form a cytokine, IL-23, with biological activities similar as well as distinct from IL-12. Immunity. Nov. 2000;13(5):715-25.

Parham et al., A receptor for the heterodimeric cytokine IL-23 is composed of IL-12Rbeta1 and a novel cytokine receptor subunit, IL-23R. J Immunol. Jun. 1, 2002;168(11):5699-708.

Patel et al., Emerging therapies for the treatment of psoriasis. Dermatol Ther (Heidelb). Dec. 2012;2(1):16. doi:10.1007/s13555-012-0016-4. Epub Oct. 25, 2012.

Pirhonen et al., Regulation of virus-induced IL-12 and IL-23 expression in human macrophages. J Immunol. Nov. 15, 2002;169(10):5673-8.

Piskin et al., Clinical improvement in chronic plaque-type psoriasis lesions after narrow-band UVB therapy is accompanied by a decrease in the expression of IFN-gamma inducers—IL-12, IL-18 and IL-23. Exp Dermatol. Dec. 2004;13(12):764-72.

Piskin, In vitro and in situ expression of IL-23 by keratinocytes in healthy skin and psoriasis lesions: enhanced expression in psoriatic skin. Effects of therapies on cytokine patterns of psoriasis. Oct. 29, 2004;7:114-31.

Sehy et al., Unambiguous Detection of IL-23 (p. 19/p. 40) Protein in Native Samples Using a Novel Enzyme-Linked Immunosorbent Assay. Abstract of Annual Meeting of Professional Research Scientists, 2005, Part 1, Abstract 560.34.

Vanden Eijnden et al., Preferential production of the IL-12(p. 40)/IL-23(p. 19) heterodimer by dendritic cells from human newborns. Eur J Immunol. Jan. 2006;36(1):21-6.

Verreck et al., Human IL-23-producing type 1 macrophages promote but IL-10-producing type 2 macrophages subvert immunity to

(56) References Cited

OTHER PUBLICATIONS (myco)bacteria. Proc Natl Acad Sci U S A. Mar. 30, 2004;101(13):4560-5. Epub Mar. 19, 2004.
Woodle et al., Phase I trial of a humanized, Fc receptor nonbinding OKT3 antibody, huOKT3gamma1(Ala-Ala) in the treatment of acute renal allograft rejection. Transplantation. Sep. 15, 1999;68(5):608-16.
Zakharova et al., Paradoxical anti-inflammatory actions of TNF-alpha: inhibition of IL-12 and IL-23 via TNF receptor 1 in macrophages and dendritic cells. J Immunol. Oct. 15, 2005;175(8):5024-33.
Alt et al. (1999) FEBS Lett. 454(1-2):90-94.
Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.
Armour et al. (1999) "Recombinant Human Igg Molecules Lacking Fcgamma Receptor I Binding and Monocyte Triggering Activities," Eur J Immunol 29:2613-2624.
Asano, R. et al. (2004) "A Diabody for Cancer Immunotherapy and its Functional Enhancement by Fusion of Human Fc Region," Abstract 3P-683, J. Biochem. 76(8):992.
Burmeister et al. (1994) "Crystal Structure of the Complex of Rat Neonatal Fc Receptor with Fc," Nature 372:379-383.
Cuesta, A.M. et al. (2010) "Multivalent Antibodies: When Design Surpasses Evolution," Trends in Biotechnol., 28(7):355-362.
Gao et al. (2004) "Efficient Inhibition of Multidrug-Resistant Human Tumors With a Recombinant anti-P-glycoprotein x anti-CD3 diabody," Leukemia 18(3):513-520.
Holliger et al. (2005) "Engineered Antibody Fragments and the Rise of Single Domains," Nature Biotechnology 23(9): 1126-1135.
Hollinger et al. (1993) "Diabodies: Small Bivalent and Bispecific Antibody Fragments," Proc. Natl. Acad. Sci. (U.S.A.) 90:6444-6448.
Hudson et al. (1999) "High Avidity scFv multimers; diabodies and triabodies," Journal of Immunological Methods 231:177-189.
Kontermann et al. (1977) "Complement recruitment using bispecific diabodies," Nature Biotechnology 15:629-631.
Kontermann, R.E. (2005) "Recombinant Bispecific Antibodies for Cancer Therapy," Acta. Pharmacol. Sin. (2005) 26(1):1-9.
Kortt et al. (2001) "Dimeric and trimeric antibodies: high avidity scFvs for cancer targeting" Biomolecular Engineering 18:95-108.
Lu, D et al. (2004) "The Effect of Variable Domain Orientation and Arrangement on the Antigen-Binding Activity of a Recombinant Human Bispecific Diabody," BBRC 318:507-513.
Lu, D. et al. (2003) "Di-Diabody: A Novel Tetravalent Bispecific Antibody Molecule by Design," J. Immunol. Meth. 279:219-232.
Lu, et al. (2005) "A Fully Human Recombinant IgG-like Bispecific Antibody to Both the Epidermal Growth Factor Receptor and the Insulin-like-Growth Factor Receptor for Enhanced Antitumor Activity," J. Biol. Chem. 280(20):19665-19672.
Marvin et al. (2005) "Recombinant Approaches to IgG-Like Bispecific Antibodies," Acta Pharmacologica Sinica, 26(6):649-658.
Mertens, N. et al., "New Recombinant Bi- and Trispedfic Antibody DerivatIVEs," In: Novel Frontiers in the Production of Compounds for Biomedical Use, vol. 1; van Broekhoven, A. et al. (Eds.); Kluwer Academic Publishers, Dordrecht, The Netherlands; pp. 195-208, 2001.
Moore, P.A. et al. (2011) "Application of Dual Affinity Retargeting Molecules to Achieve Optimal Redirected T-Cell Killing of B-Cell Lymphoma," Blood 117:4542-4551.
Olafsen et al. (2004) "Covalent Disulfide-Linked Anti-CEA Diabody Allows Site-Specific Conjugation and Radiolabeling for Tumor Targeting Applications," Protein Engineering Design &Selection. 17(1):21-27.
Steplewski et al. (1988) "Biological Activity of Human-Mouse IgG1, IgG2, IgG3, and IgG4 chimeric Monoclonal Antibodies with Antitumor Specificity," Proc. Natl. Acad. Sci. (U.S.A.) 85:4852-4856.

Stork, R. et al. (2007) "A Novel Tri-Functional Antibody Fusion Protein with Improved Pharmacokinetic Properties Generated by Fusing a Bispecific Single-Chain Diabody with an Albumin-Binding Domain from *Streptococcal* Protein G," Prot. Eng. Des. Sel. 20(11):569-576.
Takemura, S. et al. (2000) "Construction of a Diabody (Small Recombinant Bispecific Antibody) Using a Refolding System," Protein Eng. 13(8):583-588.
Todorovska et al. (2001) "Design and application of diabodies, triabodies and tetrabodies for cancer targeting," Journal of Immunological and Methods 248:47-66.
Wu et al, (2001) "Multimerization of a Chimeric Anti-CD20 Single-Chain Fv-Fc Fusion Protein is Mediated Through Variable Domain Exchange," Protein Engineering 14(2): 1025-1033.
Xiong, D. et al. (2002) "Efficient Inhibition of Human B-Cell Lymphoma Xenografts with an Anti-CD20 x Anti-CD3 Bispecific Diabody," Cancer Lett. (2002) 177(1):29-39.
Zhu, Z. et al. (1997) "Remodeling Domain Interfaces to Enhance Heterodimer Formation," Protein Sci. 6:781-788.
Aggarwal, Sudeepta et al. "Interleukin-23 Promotes a Distinct CD4 T Cell Activation State Characterized by the Production of Interleukin-17*" Journal of Biological Chemistry (2003) vol. 278, No. 3, pp. 1910-1914.
Alegre, Maria-Luisa et al. "A Non-Activating "Humanized" Anti-CD3 Monoclonal Antibody Retains Immunosuppressive Properties in Vivo" Transplantation; Jun. 1994, vol. 57, No. 11, pp. 1537-1543.
Beyer, Brian M. et al. "Crystal Structures of the Pro-Inflammatory Cytokine Interleukin-23 and its Complex with a High-Affinity Neutralizing Antibody" Journal of Molecular Biology, (2008) 382, pp. 942-955.
Catalog No. AF1716. "Anti-human IL-23 p. 19 Antibody" Lot No. JMB01. R&D Systems, Inc. Dec. 17, 2003.
Chan, Andrew C. et al. "Therapeutic antibodies for autoimmunity and inflammation" Nature Reviews, Immunology, May 2010, vol. 10, pp. 301-316.
eBioscience, Anti-Mouse IL-23 p. 19 Purified; Catalog No. 14-7232; Clone G23-8; According to all information that could be obtained from publicly available sources by Applicants, G23-8 antibody was available for purchase in 2005.
eBioscience, Anti-Mouse IL-23 p. 19 Purified; Catalog No. 14-7233; Clone 5B2; According to all information that could be obtained from publicly available sources by Applicants, 5B2 antibody was available for purchase in 2007.
eBioscience, Mouse IL-23 ELISA Ready-Set-Go! ELISA Kit, Catalog No. 88-7923, 6 pgs. According to all information that could be obtained from publicly available sources by Applicants, Mouse IL-23 ELISA Ready-Set-Go! ELISA Kit was available for purchase in 2007.
Eijnden, Serge Vanden et al. "Preferential production of the IL-12(p. 40)/IL-23(19) heterodimer by dendritic cells from human newborns" Eur. J. Immunol. (2006) vol. 36, pp. 21-26.
Fichtner-Feigl, Stefan et al. "Treatment of murine Th1- and Th2-mediated inflammatory bowel disease with NF-kB decoy oligonucleotides" Journal of Clinical Investigation, Nov. 2005, vol. 115, No. 11, pp. 3057-3071.
Happel, Kyle I, et al. "Divergent roles of IL-23 and IL-12 in host defense against Klebsiella pneumoniae" Journal of Experimental Medicine, Sep. 2005, vol. 202, No. 6, pp. 761-769.
Hegazi, Refaat A.F. et al. "Carbon monoxide ameliorates chronic murine colitis through a heme oxygenase 1-dependent pathway" Journal of Experimental Medicine, Dec. 2005, vol. 202, No. 12, pp. 1703-1713.
Hoeve, Marieke A. et al. "IL-12 receptor deficiency revisited: IL-23-mediated signaling is aslo imapired in human genetic IL-23 receptor b1deficiency" Eur. J. Immunol. (2003) vol. 33, pp. 3393-3397.
International Preliminary Report on Patentability for PCT/US2011/058869 dated May 7, 2013.
International Search Report & Written Opinion for PCT/US2011/058869 filed Nov. 2, 2011, dated Feb. 27, 2012.
Kastelein, Robert A. et al. "Discovery and Biology of IL-23 and IL-27: Related but Functionally Distinct Regulators of Inflammation" Annual Reviews Immunology, (2007) vol. 25, pp. 221-242.

(56) References Cited

OTHER PUBLICATIONS

Kidoya, Hiroyasu et al. "Fas Ligand Induces Cell-Autonomous IL-23 Production in Dendritic Cells, a Mechanism for Fas Ligand-Induced IL-17 Production" Journal of Immunology (2005) pp. 8024-8031.

Kikly, Kristine et al. "The IL-23/Th17 axis: Therapeutic targets for autoimmune inflammation" Current Opinion in Immunology (2006) 18 pp. 670-675.

Kuwashima, Naruo et al. "Delivery of Dendritic Cells Engineered to Secrete IFN-a into Central Nervous System Tumors Enhances the Efficacy of Peripheral Tumor Cell Vaccines: Dependence on Apoptotic Pathways" Journal of Immunology (2005) vol. 175, pp. 2730-2740.

Lee, Edmund et al. "Increased Expression of Interleukin 23 p. 19 and p. 40 in Lesional Skin of Patients with Psoriasis Vulgaris" Journal of Experimental Medicine (2004) vol. 199, No. 1, pp. 125-130.

Morelli, Adrian E. et al. "CD4+ T Cell Responses Elicted by Different Subsets of Human Skin Migratory Dendritic Cells" The Journal of Immunology (2005) V 175, pp. 7905-7915.

Oppmann, Birgit et al. Novel p. 19 Protein Engages IL-12 p. 40 to Form a Cytokine, IL-23, with Biological Activities Similar as Well as Distinct from IL-12. Immunity, (2000) vol. 13, pp. 715-725.

Parham, Christi, et al. "A Receptor for the Heterodimeric Cytokine IL-23 is Composed of IL-12Rβ1 and a Novel Cytokine Receptor Subunit, IL-23R" Journal of Immunology, 2002, pp. 5699-5708.

Patel, Mahir et al. "Emerging Therapies for the Treatment of Psoriasis" Dermatol Ther. (Heidelb) (2012) 2:16, 10 pgs.

Pirhonen, Jaana et al. "Regulation of Virus-Induced IL-12 and IL-23 Expression in Human Macrophages" Journal of Immunology, (2002) pp. 5673-5678.

Piskin, G., "Clinical Improvement in chronic plaque-type psoriasis lesions after narrow-based UVB therapy is accompanied by a decrease in the expression of IFN-y inducers—IL-12, IL-18, and IL-23" Experimental Dermatology (2004) vol. 13, pp. 764-772.

Piskin, Gamze "Effects of therapies on cytokine patterns of psoriasis" (2004) 25 pgs.

R&D Systems New Products, Jun. 2005. 12 pgs. www.RnDSystems.com.

R&D Systems, de novo newsletter, Mar. 2004, 10 pgs. www.rndsystems.com.

Sehy, David W. et al. Abstract 560.34 "Unambiguous Detection of IL-23 (p. 19/p. 40) Protein in Native Samples Using a Novel Enzyme-Linked Immunosorbent Assay" Experimental Biology (2005) International Congress of Physiological Sciences.

Verreck, Frank A. et al. "Human IL-23-producing type 1 macrophages promote but IL-10 producing type 2 macrophages subvert immunity to (myco)bacteria" (2004) PNAS, vol. 101, No. 13, pp. 4560-4565.

Woodle, E. Steve, et al. "Phase I Trial of a Humanized, Fc Receptor Nonbinding OKT3 Antibody, huOKT3y1(Ala-Ala) In the Treatment of Acute Renal Allograft Rejection" Transplation, (1999) vol. 68, No. 5, pp. 608-616.

Zakharova, Maria et al. "Paradoxical Anti-Inflammatory Actions of TNF-a: Inhibition of IL-12 and IL-23 via TNF Receptor 1 in Macrophages and Dendritic Cells" (2005) Journal of Immunology, vol. 175, pp. 5024-5033.

International Search Report for PCT/US2013/038109 filed on Apr. 25, 2013.

Bhambhani, Akhilesh et al. "Formulation Design and High-Throughput Excipient Selection Based on Structural Integrity and Conformational Stability of Dilute and Highly Concentrated IgG1 Monoclonal Antibody Solutions" (2012) Journal of Pharmaceutical Sciences, vol. 101, No. 3, pp. 1120-1135.

Wenzel, Sally "Severe asthma: from characteristics to phenotypes to endotypes" (2012) Clinical & Experimental Allergy vol. 42, pp. 650-658.

Haldar, Pranabashis et al. "Mepolizumab and Exacerbations of Refractory Eosinophilic Asthma" The New England Journal of Medicine (2009) vol. 360, pp. 973-984.

Irvin, Chaoyu et al. "Increased frequency of dual-positive TH2/TH17 cells in bronchoalveolar lavage fluid characterizes a population of patients with severe asthma" (2014) Journal of Allergy and Clinical Immunology, vol. 134, No. 5, pp. 1175-1186.

Ciprandi, Giorgio et al. "Serum IL-23 Strongly and Inversely Correlates with FEV1 in Asthmatic Children" (2012) International Archives of Allergy and Immunology, vol. 159, No. 2, pp. 183-186.

Naji, Nizar et al. "T Helper 17 Cells and Related Cytokines after Allergen Inhalation Challenge in Allergic Asthmatics" (2014) International Archives of Allergy & Immunology, vol. 165 pp. 27-34.

Wakashin, Hidefumi et al. "IL-23 and Th17 Cells Enhance Th2-Cell-mediated Eosinophilic Airway Inflammation in MIce" (2008) American Journal of Respiratory and Critical Care Medicine, vol. 178, pp. 1023-1032.

Li, Yanchun et al. "Silencing IL-23 expresion by a small hairpin RNA protects against asthma in mice" (2011) Experimental and Molecular Medicine, vol. 43, No. 4, pp. 197-204.

McKinley, Laura et al. "TH17 Cells Mediate Steroid-Resistant Airway Inflammation and Airway Hyperresponsiveness in Mice" (2008) The Journal of Immunology, vol. 181, pp. 4089-4097.

Fahy, John V. "Eosinophilic and Neutrophilic Inflammation in Asthma, Insights from Clinical Studies" (2009) Proceedings of the American Thoracic Society, vol. 6, pp. 256-259.

International Search Report for PCT/US2015/041706 dated Oct. 15, 2015.

Sofen, Howard et al. "Guselkumab (an IL-23-specific mAb) demonstrates clinical and molecular response in patients iwth moderate-to-severe psoriasis" (2014) Journal of Allergy and Clinical Immunology, vol. 133, pp. 1032-1040.

Tian, Suyan et al. "Meta-Analysis Derived (MAD) Transcriptome of Psoriasis Defines the "Core" Patheogenesis of Disease" (2012) PLOS One, vol. 7, Issue 9, e44274, 15 pgs.

Yeilding, Newman et al. "Development of the IL-12/23 antagonist ustekinumab in psoriasis: past, present and future perspectives" (2011) Annals of the New York Academy of Sciences, vol. 1222, pp. 30-39.

Baerveldt, E.M. et al. "Ustekinumab improves psoriasis-related gene expression in noninvolved psoriatic skin without inhibition of the antimicrobial response" (2013) British Journal of Dermatology, vol. 168, pp. 990-998.

Hegyi, Zuzana et al. Vitamin D Analog Calcipotriol Suppresses the Th17 Cytokine-Induced Proinflammatory S100 "Alarmins" Psoriasin (S100A7) and Koebnerisin (S100A15) in Psoriasis (2012) Journal of Investigative Dermatology, vol. 132, pp. 1416-1424.

Gudjonsson, Johann E. et al. "Assessment of the Psoriatic Transcriptome in a Large Sample: Additional Regulated Genes and Comparisons with in Vitro Models" (2010) Journal of Investigative Dermatology, vol. 130, pp. 1829-1840.

Suarez-Farinas, Mayte et al. "Expanding the Psoriasis Disease Profile: Interrogation of the Skin and Serum of Patients with Moderate-to-Severe Psoriasis" (2012) Journal of Investigative Dermatology, vol. 132, pp. 2552-2564.

Mallbris, Lotus et al. "Neutrophil gelatinase-associated lipocalin is a marker for dysregulated keratinocyte differentiation in human skin" (2002) Experimental Dermatology, vol. 11, pp. 584-591.

Krueger, James G. et al. "Anti-IL-23A mAb BI 655066 for treatment of moderate-to-severe psoriasis: Safety, efficacy, pharmacokinetics, and biomarker results of a single-rising-dose, randomized, double-blind, placebo-controlled trial" (2015) Journal of Allergy and Clinical Immunology vol. 136, pp. 116-124.

Brodmerkel, Carrie et al. "The Skin and Circulating Immune Profile of Therapeutic IL-12/23 Blockade in Psoriasis Patients Treated with Ustekinumab" Clinical Immunology, Academic Press, vol. 131, Jan. 1, 2009, p. S5, Abstract.

McInnes, Iain B. et al. "Efficacy and safety of secukinumab, a fully human anti-interleukin-17A monoclonal antibody, in patients with moderate-to-severe psoriatic arthritis: a 24-week, randomised, double-blind, placebo-controlled, phase II proof-of-concept trail" (2014) Ann Rheum Dis, vol. 73, pp. 349-356.

Choy, David F. et al. "Th2 and Th17 inflammatory pathways are reciprocally regulated in asthma" (2015) www.ScienceTranslationalMedicine.org vol. 7, Issue 301, 301ra129, 11 pgs.

(56) References Cited

OTHER PUBLICATIONS

International Search Report for PCT/US2016/016061 dated May 18, 2016.
Anonymous: "A Phase 2 Multicecenter, Randomized, Placebo- and Active-Comparator-Controlled, Dose-Ranging Trial to Evaluate CNTO 1959 for the Treatment of Subjects with Moderate to Sever Plaque-type Psoriasis (X-PLORE)" Mar. 10, 2014, ClincialTrails Identifier NCT01483599, 4 pgs, ClinicalTrials.gov.
Kofoed, Kristian, et al. "New Drugs and Treatment Targets in Psoriasis" (2015) Acta Derm Venereol, vol. 95, pp. 133-139.
Hu, Chuanpu et al. "Information contributed by meta-analysis in exposure-response modeling: application to phase 2 does selection of guselkumab in patients with moderate-to-severe psoriasis" (2014) Journal of Pharmacokinet Pharmacodyn vol. 41, pp. 239-250.
Anonymous: "A Phase 2a, Multicenter, Randomized, Double-blind, Placebo-controlled Study Evaluating the Efficacy and Safety of Guselkumab in the Treatment of Subjects with Active Psoriatic Arthritis" 4 pgs, Jan. 26, 2015, Clinical Trials Identifier: NCT02319759, Clinicaltrials.gov.
Anonymous: "A 52-Week, Phase 3, Randomized, Active Comparator and Placebo-Controlled, Parallel Design Study to Evaluate the Efficacy and Safety/Tolerability of Subcutaneous SCH 9000222/MK-3222, Followed by an Optional Long-Term Safety Extension Study, in Subjects with Moderate-to-Severe Chronic Plaque Psoriasis" 4 pgs, Dec. 30, 2014, Clinical Trials Identifier: NCT01729754, Clinictrials.gov.
Gaffen, Sarah L. et al. "The IL-23-IL-17 immune axis: from mechanisms to therapeutic testing" (2014) Nature Reviews, vol. 14, pp. 585-600.
Papp, K. et al. "Tildrakizumab (MK-3222) an anti-interleukin-23p19 monoclonal antibody, improves psoriasis in a phase IIb randomized placebo-controlled trial" (2015) British Journal of Dermatology, vol. 173, pp. 930-939.
Kopp, Tamara et al. "Clinical improvement in psoriasis with specific targeting of interleukin-23" (2015) Nature, vol. 521, No. 7551, pp. 222-226.
Gordon, Kenneth B. et al. "A Phase 2 Trial of Guselkumab versus Adalimumab for Plaque Psoriasis" (2015) New England Journal of Medicine, vol. 373, No. 2, pp. 136-144.
Leonardi, Craig et al. "Efficacy and safety of ustekinumab, a human interleukin-12/23 monoclonal antibody, in patients with psoriasis: 76-weeks results form a randomised, double-blind, placebo-controlled trail (PHOENIX 1)" (2008) The Lancet, vol. 371, pp. 1665-1674.
International Search Report for PCT/US2016/027263 dated Jun. 29, 2016.
Cao, Hao et al. "Anti-IL-23 antibody blockade of IL-23/IL-17 pathway attenuates airway obliteration in rat orthotopic tracheal transplantation" (2011) International Immunopharmacology, vol. 11, pp. 569-575.
Cupparic, Ciprandi G. et al. "Serum IL-23 in Asthmatic Children" (2012) Journal of Biological Regulators & Homeostatic Agents, vol. 26, No. 1(8), pp. 53-61.
International Search Report for PCT/US2016/051844 dated Jan. 10, 2017.
International Search Report for PCT/US2015/048260 dated Jan. 29, 2016.
Opposition filed in Colombian Patent Application No. NC2017/0002253, dated Nov. 3, 2017 (17 pages total with English translation).
Wypych J, et al. "Human IgG2 antibodies display disulfide-mediated structural isoforms," J Biol Chem. Jun. 6, 2008; 283 (23):16194-205.

COMPOUND TARGETING IL-23A AND TNF-ALPHA AND USES THEREOF

RELATED APPLICATION

This application claims the benefit of the filing date under 35 U.S.C. §119 of U.S. Provisional Application Ser. No. 62/045,498, filed Sep. 3, 2014, and entitled Compound Targeting IL-23A and TNF-ALPHA and Uses Thereof, the entire contents of which are incorporated by reference herein.

BACKGROUND OF THE INVENTION

Inflammation involves an innate and adaptive immune response that is required for fighting infection. However, when the inflammation becomes unchecked autoimmune or autoinflammatory diseases, neurodegenerative disease, and even cancer can develop. It is well established that inhibiting activity of proinflammatory cytokines such as IL1, TNF-alpha, IL6, IL12, IL17, IL18, or IL23 reduces inflammation and suppresses specific pathways that activate immune cells.

Interleukin 23 (IL23) is a heterodimeric cytokine consisting of two subunits, p40 and p19. The p19 subunit is also referred to as IL-23A. While the p19 subunit is unique to IL23, the p40 subunit is shared with the cytokine IL12. IL23 is emerging as a key regulator of pathogenic Th17, γδ T and innate lymphoid cells (ILCs) driving the production of IL17, IL22 and other cytokines that lead to local tissue inflammation and damage. IL23 promotes upregulation of the matrix metalloprotease MMP9, increases angiogenesis, reduces CD8+ T cell infiltration, and has been implicated in the development of cancerous tumors. In addition, in conjunction with IL6 and TGF-beta1, IL23 stimulates naive CD4+ T cells to differentiate into Th17 cells. In turn, the Th17 cells produce IL17, a proinflammatory cytokine that enhances T cell priming and stimulates the production of proinflammatory cytokines such as IL1, IL6, TNF-alpha, NOS-2, and also induces expression of chemokines resulting in inflammation and disease pathogenesis. IL23 exerts its effects via a cell surface receptor composed of the IL12β1 subunit of IL12 receptor partnered with a unique IL23R subunit. Expression of the IL23R is restricted to specific populations of immune cells and is found primarily on subsets of T cells (αβ and γδ TCR+) and NK cells.

In mice, genetic ablation of the IL23p19 gene results in selective loss of IL23 function accompanied by severely compromised T-dependent immune responses, including reduced production of antigen-specific immunoglobulins and impaired delayed type hypersensitivity responses (Ghilardi N, et al. (2004) *J. Immunol.* 172(5): 2827-33). Knockout mice deficient in either IL23p40 or IL23p19, or in either subunit of the IL23 receptor (IL23R and IL12-beta1), develop less severe symptoms in animal models of multiple sclerosis, arthritis and inflammatory bowel disease. Similar results have been obtained using an antibody specific for IL23p19 in EAE and a T cell mediated colitis model further substantiates the role of IL23 in these disease settings (Chen Y. et al. (2006) *J. Clin. Invet.* 116(5):1317-26; Elson C O. et al. (2007) *Gastroenterology* 132(7): 2359-70). This highlights the importance of IL23 in chronic inflammation (Langowski et al. (2006) *Nature* 442 (7101): 461-5; Kikly K, et al. (2006) *Curr. Opin. Immunol.* 18 (6): 670-5). In addition, elevated IL23 production has been implicated as being a major factor in inflammatory arthritis and in inflammatory autoimmune diseases (Adamopoulos et al. (2011) *J. Immunol.* 187: 593-594; and Langris et al. (2005) *J. Exp. Med.* 201:233-240). A connection between IL23, its downstream cytokine IL22, and bone formation has been published in a mouse model system in which IL23 is overexpressed (Sherlock et al. (2012) *Nat. Med.* 18: 1069-76).

The homotrimeric TNF-α cytokine is expressed predominantly by macrophages, lymphocytes, endothelial cells and fibroblasts and binds two distinct receptors: TNFRI, expressed on nearly all cell types and TNFRII, with more limited expression on immune cells (CD4+ T cells, NK cells). Like many TNF superfamily members, TNF-α exists as both membrane and soluble forms, the soluble form arising from cleavage of the membrane form by the ADAM12 metalloprotease (TACE, TNFα converting enzyme). Both membrane-bound and soluble forms of the cytokine are biologically active.

Tumor necrosis factor (TNF-alpha/TNF-α) is a proinflammatory cytokine that stimulates the acute phase of inflammation. Tumor necrosis factor increases vascular permeability through induction of IL8, thereby recruiting macrophage and neutrophils to a site of infection. Once present, activated macrophages continue to produce TNF-alpha, thereby maintaining and amplifying the inflammatory response. The primary role of TNF-alpha is the regulation of immune cells; however, TNF-alpha is also involved in the regulation of a wide spectrum of biological processes including cell proliferation, differentiation, apoptosis, lipid metabolism, and coagulation. TNF-alpha is able to induce inflammation, induce apoptotic cell death, inhibit tumorigenesis and inhibit viral replication.

Dysregulation of TNF-alpha production has been implicated in a variety of human diseases, including autoimmune disease (e.g. rheumatoid arthritis (RA), Crohn's disease, multiple sclerosis), inflammatory bowel disease (IBD), ulcerative colitis, psoriasis, toxic shock, graft versus host disease, insulin resistance, Alzheimer's disease, cancer, and major depression (Swardfager W, et al. (2010) *Biol Psychiatry* 68 (10): 930-941; (Locksley R M, et al. (2001) *Cell* 104 (4): 487-501; Dowlati et al., (2010) *Biol Psychiatry* 67 (5): 446-457; Brynskov J. et al. (2002) *Gut* 51 (1): 37-43).

Antibodies have been used as biologic therapies for inhibition of TNF-alpha and IL23 in order to treat a variety of inflammatory diseases. Infliximab (Centocor, Malvern, Pa.) described in U.S. Pat. Nos. 6,277,969, 6,284,471, and 6,790,444, is a chimeric anti-TNF-alpha monoclonal IgG antibody bearing human IgG4 constant and mouse variable regions and is used clinically to treat rheumatoid arthritis, psoriatic arthritis, ankylosing spondylitis, Crohn's disease, ulcerative colitis and plaque psoriasis. Monoclonal antibody adalimumab (clone D2E7; Abbott Laboratories, Abbott Park, Ill.) described in U.S. Pat. No. 6,090,382, is an anti-TNF-alpha therapy used clinically to treat rheumatoid arthritis, Crohn's disease, psoriasis, psoriatic arthritis, ankylosing spondylitis, and juvenile idiopathic arthritis. Golimumab is a TNF-alpha blocker used to treat rheumatoid arthritis, psoriatic arthritis, ankylosing spondylitis, and ulcerative colitis. In addition, human monoclonal antibody ustekinumab (Centocor, Inc, Malvern, Pa.), described in U.S. Pat. Nos. 6,902,734 and 7,166,285, is directed against interleukin 12 and interleukin 23 (specifically the p40 subunit), is clinically used to treat severe plaque psoriasis, and is further being investigated for the treatment of psoriatic arthritis, multiple sclerosis, and sarcoidosis. However, anti-TNF-α therapies have reported side effects [see for example: Keane J et al. (2001)]. Tuberculosis is associated with infliximab, a tumor necrosis factor α-neutralizing agent. *N Engl J Med* 345 (15):1098-1104; Scheinfeld N. (2005) Adalimumab: a review of side effects. *Expert Opin Drug*

Saf. 4(4):637-41; Chovel-Sella A et al. (2012) Clinical efficacy and adverse effects of golimumab in the treatment of rheumatoid arthritis. *Isr Med Assoc J.* 14(6):390-4]. Identification of more efficacious treatments should allow for administration of reduced dosages, as well as lower costs associated with the treatment.

There remains a need for compositions with increased efficacy for treating and preventing autoimmune or inflammatory diseases.

SUMMARY OF THE INVENTION

Provided herein are compounds specific for TNF-alpha and IL23A, compositions comprising such compounds, as well as methods of use and production thereof.

Aspects of the disclosure relate to a compound comprising a first polypeptide and a second polypeptide, wherein:
(A) said first polypeptide comprises:
   (i) a light chain variable domain of a first immunoglobulin (VL1) specific for a first target protein;
   (ii) a heavy chain variable domain of a second immunoglobulin (VH2) specific for a second target protein; and
   (iii) a hinge region, a heavy chain constant region 2 (CH2) and a heavy chain constant region 3 (CH3); and
(B) said second polypeptide comprises:
   (i) a light chain variable domain of the second immunoglobulin (VL2) specific for said second target protein;
   (ii) a heavy chain variable domain of the first immunoglobulin (VH1) specific for said first target protein;
wherein:
   (i) said VL1 and VH1 associate to form a binding site that binds said first target protein;
   (ii) said VL2 and VH2 associate to form a binding site that binds said second target protein;
   (iii) said heavy chain constant region 2 (CH2) comprises a tyrosine at position 252, a threonine at position 254 and a glutamic acid a position 256, numbered according to the EU index as in Kabat for a conventional antibody; and
   (iv) said first target protein is TNF-alpha and said second target protein is IL-23A or said first target protein is IL-23A and said second target protein is TNF-alpha, wherein:
      (i) said VL1 comprises SEQ ID NO:2, said VH1 comprises SEQ ID NO:1, said VL2 comprises SEQ ID NO:8 and said VH2 comprises SEQ ID NO:7; or
      (ii) said VL1 comprises SEQ ID NO:4 or 6, said VH1 comprises SEQ ID NO:3 or 5, said VL2 comprises SEQ ID NO:8 and said VH2 comprises SEQ ID NO:7; or
      (iii) said VL1 comprises SEQ ID NO:8, said VH1 comprises SEQ ID NO:7, said VL2 comprises SEQ ID NO:2 and said VH2 comprises SEQ ID NO:1; or
      (iv) said VL1 comprises SEQ ID NO:8, said VH1 comprises SEQ ID NO:7, said VL2 comprises SEQ ID NO:4 or 6 and said VH2 comprises SEQ ID NO:3 or 5.

In some embodiments, in (ii) said VL1 comprises SEQ ID NO:4, said VH1 comprises SEQ ID NO:3, said VL2 comprises SEQ ID NO:8 and said VH2 comprises SEQ ID NO:7. In some embodiments, in (ii) said VL1 comprises SEQ ID NO:6, said VH1 comprises SEQ ID NO:5, said VL2 comprises SEQ ID NO:8 and said VH2 comprises SEQ ID NO:7. In some embodiments, in (iv) said VL2 comprises SEQ ID NO:4, said VH2 comprises SEQ ID NO:3, said VL1 comprises SEQ ID NO:8 and said VH1 comprises SEQ ID NO:7. In some embodiments, in (iv) said VL2 comprises SEQ ID NO:6, said VH2 comprises SEQ ID NO:5, said VL1 comprises SEQ ID NO:8 and said VH1 comprises SEQ ID NO:7.

In some embodiments, said first polypeptide further comprises a first linker between said VL1 and said VH2 and said second polypeptide further comprises a second linker between said VL2 and said VH1. In some embodiments, said first linker or said second linker comprises the amino acid sequence GGGSGGG (SEQ ID NO:9). In some embodiments, said first linker and said second linker comprise the amino acid sequence GGGSGGG (SEQ ID NO:9).

In some embodiments, said first polypeptide further comprises a heavy chain constant region 1 domain (CH1) and said second polypeptide further comprises a light chain constant region domain (CL), wherein said CL and said CH1 are associated together via a disulfide bond to form a C1 domain.

In some embodiments, said first polypeptide further comprises a third linker between said VH2 and said CH1 and said second polypeptide further comprises a fourth linker between said VH1 and said CL. In some embodiments, said third linker comprises the amino acid sequence FNRGES (SEQ ID NO:11). In some embodiments, said fourth linker comprises the amino acid sequence VEPKSS (SEQ ID NO:12). In some embodiments, said third linker comprises the amino acid sequence FNRGES (SEQ ID NO:11) and said fourth linker comprises the amino acid sequence VEPKSS (SEQ ID NO:12). In some embodiments, third linker or said fourth linker comprises the amino acid sequence LGGGSG (SEQ ID NO:10). In some embodiments, said third linker and said fourth linker comprise the amino acid sequence LGGGSG (SEQ ID NO:10).

In some embodiments, said heavy chain constant region 2 (CH2) comprises an alanine at positions 234 and an alanine at position 235, numbered according to the EU index as in Kabat for a conventional antibody.

In some embodiments, the amino acid sequence of said hinge region, said heavy chain constant region 2 (CH2) or said heavy chain constant region 3 (CH3) is derived from a IgG1 or from a IgG4. In some embodiments, said hinge region comprises the amino acid sequence EPKSCDKTHTCPPCP (SEQ ID NO:40).

In some embodiments, said compound comprises two said first polypeptides and two said second polypeptides, wherein said two first polypeptides are associated together via at least one disulfide bond. In some embodiments, said compound comprises two said first polypeptides and two said second polypeptides, wherein said two first polypeptides are associated together via at least one disulfide bond and wherein each of said first polypeptide is associate to one said second polypeptide via at least one disulfide bond.

In some embodiments,
(i) said first polypeptide comprises the amino acid sequence of SEQ ID NO:13 and said second polypeptide comprises the amino acid sequence of SEQ ID NO:14;
(ii) said first polypeptide comprises the amino acid sequence of SEQ ID NO:15 and said second polypeptide comprises the amino acid sequence of SEQ ID NO:16;
(iii) said first polypeptide comprises the amino acid sequence of SEQ ID NO:17 and said second polypeptide comprises the amino acid sequence of SEQ ID NO:18;
(iv) said first polypeptide comprises the amino acid sequence of SEQ ID NO:19 and said second polypeptide comprises the amino acid sequence of SEQ ID NO:20;

(v) said first polypeptide comprises the amino acid sequence of SEQ ID NO:21 and said second polypeptide comprises the amino acid sequence of SEQ ID NO:22;
(vi) said first polypeptide comprises the amino acid sequence of SEQ ID NO:23 and said second polypeptide comprises the amino acid sequence of SEQ ID NO:24;
(vii) said first polypeptide comprises the amino acid sequence of SEQ ID NO:25 and said second polypeptide comprises the amino acid sequence of SEQ ID NO:26;
(viii) said first polypeptide comprises the amino acid sequence of SEQ ID NO:27 and said second polypeptide comprises the amino acid sequence of SEQ ID NO:28;
(ix) said first polypeptide comprises the amino acid sequence of SEQ ID NO:29 and said second polypeptide comprises the amino acid sequence of SEQ ID NO:30;
(x) said first polypeptide comprises the amino acid sequence of SEQ ID NO:31 and said second polypeptide comprises the amino acid sequence of SEQ ID NO:32;
(xi) said first polypeptide comprises the amino acid sequence of SEQ ID NO:33 and said second polypeptide comprises the amino acid sequence of SEQ ID NO:34; or
(xi) said first polypeptide comprises the amino acid sequence of SEQ ID NO:35 and said second polypeptide comprises the amino acid sequence of SEQ ID NO:36.

In some embodiments, wherein said compound comprises two said first polypeptides and two said second polypeptides, wherein said two first polypeptides are associated together via at least one disulfide bond.

In some embodiments, said compound comprises two said first polypeptides and two said second polypeptides, and wherein the CH2 and CH3, and CH1 if present, of one of the first polypeptides associates with the CH2 and CH3, and CH1 if present, of the other of the first polypeptides to form a tetravalent molecule. In some embodiments, said compound comprises two said first polypeptides and two said second polypeptides, wherein each of said first polypeptides comprises a CH1, a CH2 and a CH3 and each of said second polypeptides comprises a CL and wherein the CH2 and CH3 of one of the first polypeptides associates with the CH2 and CH3 of the other of the first polypeptides and the CH1 of each said first polypeptides associates with the CL of one said second polypeptides to form a tetravalent molecule.

Other aspects of the disclosure relate to a first compound that competes with a second compound for binding to IL-23A and to TNF-alpha, wherein said first compound comprises a third polypeptide and fourth polypeptide, wherein:
(A) said third polypeptide comprises:
(i) a light chain variable domain of a first immunoglobulin (VL1) specific for a first target protein;
(ii) a heavy chain variable domain of a second immunoglobulin (VH2) specific for a second target protein; and
(iii) a hinge region, a heavy chain constant region 2 (CH2) and a heavy chain constant region 3 (CH3); and
(B) said fourth polypeptide comprises:
(i) a light chain variable domain of the second immunoglobulin (VL2) specific for said second target protein;
(ii) a heavy chain variable domain of the first immunoglobulin (VH1) specific for said first target protein;

and wherein
(i) said VL1 and VH1 associate to form a binding site that binds said first target protein;
(ii) said VL2 and VH2 associate to form a binding site that binds said second target protein; and
(iii) said first target protein is TNF-alpha and said second target protein is IL-23A or said first target protein is IL-23A and said second target protein is TNF-alpha, and wherein said second compound comprises a first polypeptide and a second polypeptide, wherein:
(i) said first polypeptide comprises the amino acid sequence of SEQ ID NO:13 and said second polypeptide comprises the amino acid sequence of SEQ ID NO:14;
(ii) said first polypeptide comprises the amino acid sequence of SEQ ID NO:15 and said second polypeptide comprises the amino acid sequence of SEQ ID NO:16;
(iii) said first polypeptide comprises the amino acid sequence of SEQ ID NO:17 and said second polypeptide comprises the amino acid sequence of SEQ ID NO:18;
(iv) said first polypeptide comprises the amino acid sequence of SEQ ID NO:19 and said second polypeptide comprises the amino acid sequence of SEQ ID NO:20;
(v) said first polypeptide comprises the amino acid sequence of SEQ ID NO:21 and said second polypeptide comprises the amino acid sequence of SEQ ID NO:22;
(vi) said first polypeptide comprises the amino acid sequence of SEQ ID NO:23 and said second polypeptide comprises the amino acid sequence of SEQ ID NO:24;
(vii) said first polypeptide comprises the amino acid sequence of SEQ ID NO:25 and said second polypeptide comprises the amino acid sequence of SEQ ID NO:26;
(viii) said first polypeptide comprises the amino acid sequence of SEQ ID NO:27 and said second polypeptide comprises the amino acid sequence of SEQ ID NO:28;
(ix) said first polypeptide comprises the amino acid sequence of SEQ ID NO:29 and said second polypeptide comprises the amino acid sequence of SEQ ID NO:30;
(x) said first polypeptide comprises the amino acid sequence of SEQ ID NO:31 and said second polypeptide comprises the amino acid sequence of SEQ ID NO:32;
(xi) said first polypeptide comprises the amino acid sequence of SEQ ID NO:33 and said second polypeptide comprises the amino acid sequence of SEQ ID NO:34; or
(xii) said first polypeptide comprises the amino acid sequence of SEQ ID NO:35 and said second polypeptide comprises the amino acid sequence of SEQ ID NO:36.

Yet other aspects of the disclosure relate to a pharmaceutical composition comprising a compound described herein, such as a compound described above.

Other aspects of the disclosure relate to a method of treating an autoimmune or an inflammatory disease comprising administering a compound described herein, such as a compound described above, or a pharmaceutical composition comprising said compound to a subject.

Yet other aspects of the disclosure relate to a compound described herein, such as a compound described above, for use in medicine. In some embodiments, said use is the treatment of an autoimmune or an inflammatory disease.

Other aspects of the disclosure relate to a pharmaceutical composition comprising a compound described herein, such as a compound described above, for use in medicine. In some embodiments, said use is the treatment of an autoimmune or an inflammatory disease.

Yet other aspects of the disclosure relate to a use of a compound described herein, such as a compound described above, in the manufacture of a medicament for use in medicine. In some embodiments, said use is the treatment of an autoimmune or an inflammatory disease.

Other aspects of the disclosure relate to a use of a pharmaceutical composition described herein, such as a pharmaceutical composition described above, in the manufacture of a medicament for use in medicine. In some embodiments, said use is the treatment of an autoimmune or an inflammatory disease.

Yet other aspects of the disclosure relate to a nucleic acid comprising a nucleotide sequence encoding a polypeptide described herein, such as a polypeptide described above. Other aspects of the disclosure relate to a vector comprising said nucleic acid. In some embodiments, the vector comprises a promoter operably linked to said nucleic acid. Other aspects of the disclosure relate to a cell comprising said nucleic acid or said vector.

Other aspects of the disclosure relate to a method of producing a compound or polypeptide as described herein, such as a polypeptide described above, comprising obtaining a cell described herein, such a cell described above, and expressing a nucleic acid as described herein in said cell. In some embodiments, the method further comprises isolating and purifying said polypeptide or compound.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1A:
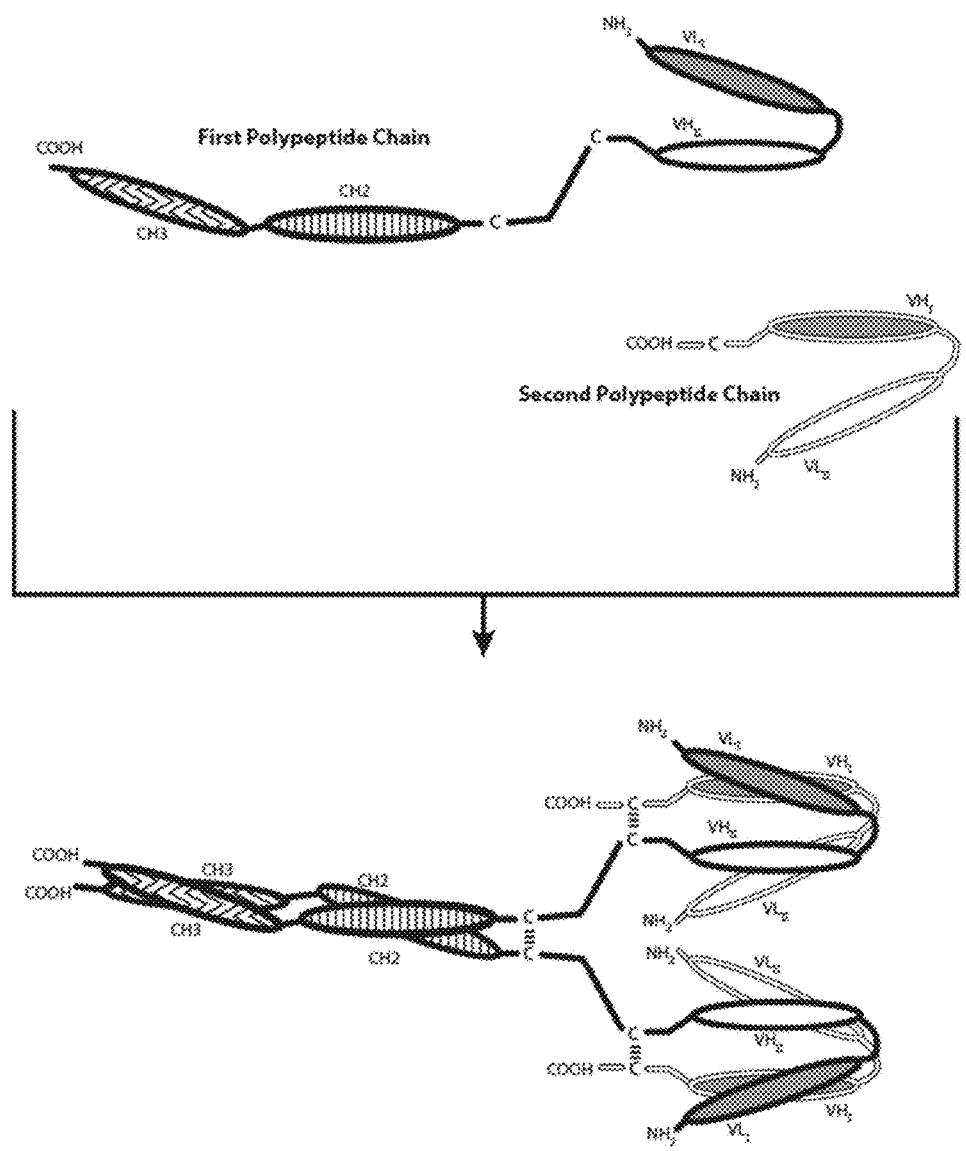
FIG. 1A is a diagram of an exemplary compound specific for TNF-alpha and IL23A. The first polypeptide chain contains CH3, CH2, $VH_2$ ($VH_{II}$) and $VL_1$ ($VL_I$) domains. The second polypeptide chain contains $VH_1$ ($VH_I$) and $VL_2$($VL_{II}$) domains. $VL_1$ and $VH_1$ are specific for a first target protein (either TNF-alpha or IL23A) and $VL_2$ and $VH_2$ are specific for a second target protein (either IL23A or TNF-alpha). The upper panel shows each polypeptide chain separately. The lower panel shows a tetravalent compound formed through association of the CH2 and CH3 domains of one first polypeptide with the CH2 and CH3 domains of another first polypeptide. The binding domains for the first and second target protein are formed through association of $VH_1$ and $VL_1$ and through association $VH_2$ and $VL_2$, respectively.

Described herein compounds that bind to both TNF-alpha (also referred to herein as TNF-α or TNFa) and IL23A (also referred to as IL23p19 or IL-23A). To date, there have been no approved compounds that target both TNF-alpha and IL23A. There are limited studies with simultaneous neutralization of two/more key inflammatory mediators using biotherapeutics approach. While these studies failed to show improvement in clinical outcomes that were measured for rheumatoid arthritis (RA), a bi-functional therapeutic targeting the same combination has not been described to date. In addition, such combinations may increase side effects, such as the risk of infection (see, e.g., Genovese, M. C., Cohen, S., Moreland, L., Lium, D., Robbins, S., et al. (2004). *Arth. Rheum.* 50, 1412-9; Genovese, M. C., Cohen, S., Moreland, L., Lium, D., Robbins, S., et al. (2004). *Arth. Rheum.* 50, 1412-9; and Weinblatt, M., Schiff, M., Goldman, A. Kremer, J., Luggen, M., et al. (2007). *Ann. Rheum. Dis.* 66, 228-34). Further, such bi-specific compounds have been difficult to design, due to issues related to solubility (e.g., aggregation) and stability (e.g., poor pharmacokinetics).

Surprisingly, the compounds described herein that bind to both TNF-alpha and IL23A have been found to have similar or improved properties compared to individual antibodies that target either IL23A or TNF-alpha. These compounds were also found to have suitable pharmacokinetics and were soluble at suitable ranges for dosing purposes. Further, in some embodiments, there are advantages of single administration over multiple individual dose administration from the perspective of side effects of the individual therapies, and lower dosage. In addition, in some embodiments, the CMC properties of the compounds showed that compounds had low aggregation. In one aspect, exemplary compounds showed particularly low aggregation. It was also shown that the linkers were optimized to improve stability and prevented cleavage and that the YTE mutation improved Fc Rn affinity. The compounds described herein are believed to have one or more advantageous properties, e.g., decreased side effects, increased ease and safety of administration, an increased half-life, increased binding affinity, or increased inhibitory activity, compared to standard antibody molecules, e.g., an IgG molecule or antigen-binding fragment (Fab).

Accordingly, aspects of the disclosure relate to compounds specific for both TNF-alpha and IL23A, as well as methods of use and production of such compounds.

Compounds

Aspects of the disclosure relate to a compound specific for both TNF-alpha and IL23A. An exemplary protein sequence for TNF-alpha and an exemplary protein sequence for IL23A are shown below.

>NP_000585.2 - TNF-alpha [Homo sapiens]
(SEQ ID NO: 144)
MSTESMIRDVLAEEALPKKTGGPQGSRRCLFLSLFSFLIVAGATTLFCL

LHFGVIGPQREEFPRDLSLISPLAQAVRSSSRTPSDKPVAHVVANPQAEG

QLQWLNRRANALLANGVELRDNQLVVPSEGLYLIYSQVLFKGQGCPSTHV

LLTHTISRIAVSYQTKVNLLSAIKSPCQRETPEGAEAKPWYEPIYLGGVF

QLEKGDRLSAEINRPDYLDFAESGQVYFGIIAL

>NP_057668.1 - IL23A [Homo sapiens]
(SEQ ID NO: 145)
MLGSRAVMLLLLLPWTAQGRAVPGGSSPAWTQCQQLSQKLCTLAWSAHPL

VGHMDLREEGDEETTNDVPHIQCGDGCDPQGLRDNSQFCLQRIHQGLIFY

EKLLGSDIFTGEPSLLPDSPVGQLHASLLGLSQLLQPEGHHWETQQIPSL

SPSQPWQRLLLRFKILRSLQAFVAVAARVFAHGAATLSP (amino acids 1-19 are a predicted signal sequence)

In some embodiments, the compound comprises a first polypeptide and a second polypeptide. In some embodiments, the first polypeptide comprises (i) a light chain variable domain of a first immunoglobulin (VL1) specific for a first target protein, (ii) a heavy chain variable domain of a second immunoglobulin (VH2) specific for a second target protein; and (iii) a hinge region, a heavy chain constant region 2 (CH2) and a heavy chain constant region 3 (CH3). In some embodiments, the first polypeptide further comprises a heavy chain constant region 1 (CH1). In some embodiments, the second polypeptide comprises: (i) a light chain variable domain of the second immunoglobulin (VL2) specific for the second target protein; (ii) a heavy chain variable domain of the first immunoglobulin (VH1) specific for the first target protein. In some embodiments, the first polypeptide further comprises a light chain constant region (CL).

It is to be understood that the variable domains and constant domains/regions of the first polypeptide can be in any order and that the variable domains and constant domains/regions (if any) of the second polypeptide can be in any order. Multiple exemplary configurations for the domains/regions on the first and second polypeptide from N-terminus to C-terminus are shown below.

Figure 1B:
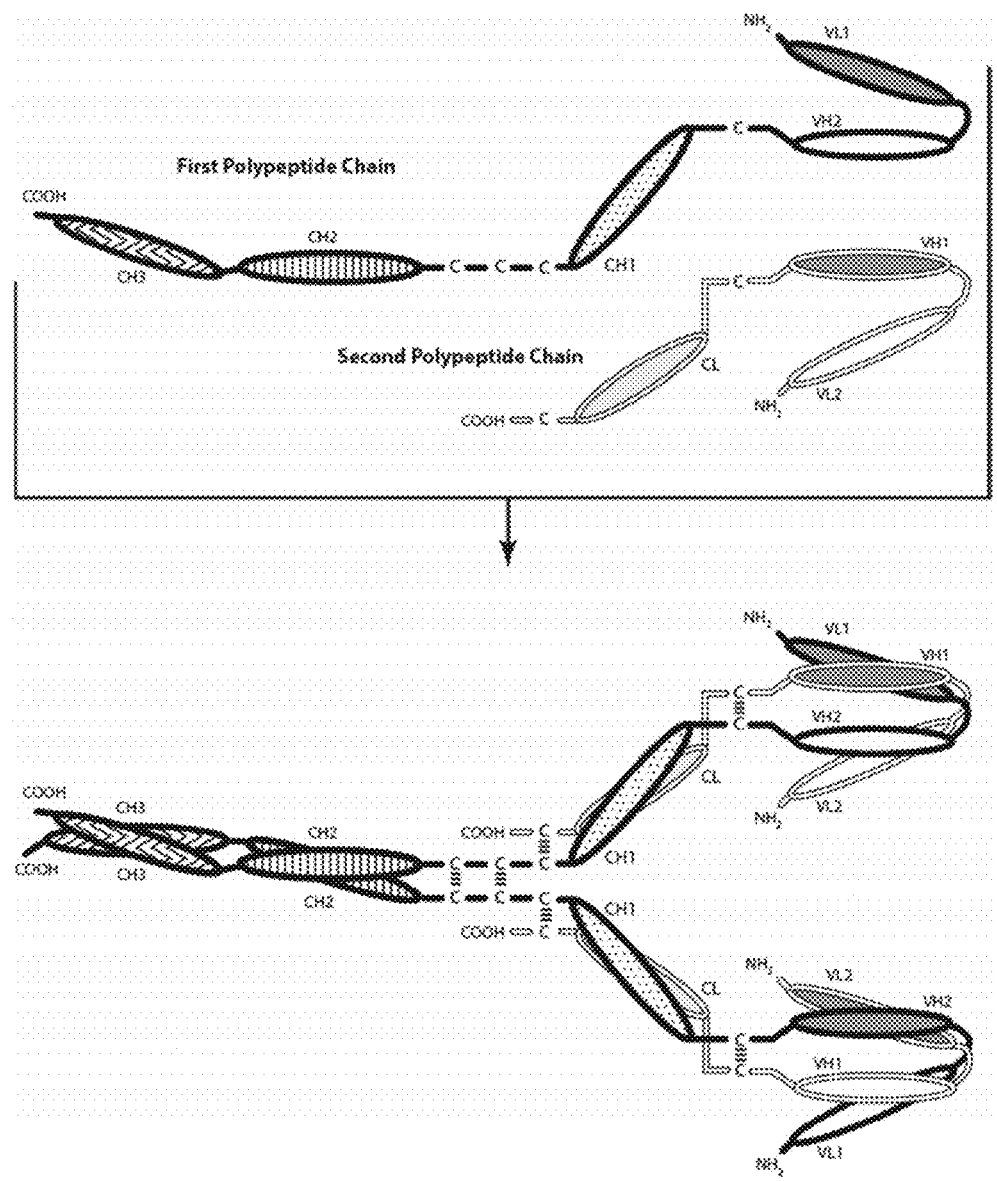
FIG. 1B is a diagram of another exemplary compound specific for TNF-alpha and IL23A. The first polypeptide chain contains CH3, CH2, CH1, $VH_2$ ($VH_{II}$) and $VL_1$ ($VL_I$) domains. The second polypeptide chain contains CL, $VH_1$ ($VH_I$) and $VL_2$($VL_{II}$) domains. $VL_1$ and $VH_1$ are specific for a first target protein (either TNF-alpha or IL23A) and $VL_2$ and $VH_2$ are specific for a second target protein (either IL23A or TNF-alpha). The upper panel shows each polypeptide chain separately. The lower panel shows a tetravalent compound formed through association of the CH2 and CH3 domains of one first polypeptide with the CH2 and CH3 domains of another first polypeptide. The binding domains for the first and second target protein are formed through association of $VH_1$ and $VL_1$ and through association $VH_2$ and $VL_2$, respectively. The compound is further associated through interactions between the CL and CH1 domains.

First polypeptide configuration 1: N-VL1-VH2-hinge-CH2-CH3-C
First polypeptide configuration 2: N-VH2-VL1-hinge-CH2-CH3-C
First polypeptide configuration 3: N-VL1-VH2-CH1-hinge-CH2-CH3-C
First polypeptide configuration 4: N-VH2-VL1-CH1-hinge-CH2-CH3-C
Second polypeptide configuration 1: N-VL2-VH1-C
Second polypeptide configuration 2: N-VH1-VL2-C
Second polypeptide configuration 3: N-VL2-VH1-CL-C
Second polypeptide configuration 4: N-VH1-VL2-CL-C Exemplary configurations of the compound are shown in FIGS. 1A and 1B. In some embodiments, the compound comprises the first polypeptide in configuration 1 and the second polypeptide in configuration 1. In some embodiments, the compound comprises the first polypeptide in configuration 3 and the second polypeptide in configuration 3.

In some embodiments, the variable regions of the first polypeptide and the second polypeptide associate with one another to form a binding site for the first target protein and a binding site for the second target protein. In some embodiments, the VL1 of the first polypeptide and the VH1 of the second polypeptide associate to form a binding site that binds the first target protein and the VL2 of the second polypeptide and the VH2 of the first polypeptide associate to form a binding site that binds the second target protein. In some embodiments, the first target protein is TNF-alpha and the second target protein is IL23A. In other embodiments, the first target protein is IL23A and the second target protein is TNF-alpha. It is to be understood that the terms "first" and "second" are not meant to imply a level of importance to either target protein.

Exemplary combinations of sequences for each of VL1, VH1, VL2, and VH2 are provided below in Table 1 and also in Table 2A in Example 1.

TABLE 1

Exemplary combinations of sequences for VL1, VH1, VL2, and VH2.

| Combination Number | VL1 sequence | VH1 sequence | VL2 sequence | VH2 sequence |
| --- | --- | --- | --- | --- |
| 1 | SEQ ID NO: 2 | SEQ ID NO: 1 | SEQ ID NO: 8 | SEQ ID NO: 7 |
| 2 | SEQ ID NO: 8 | SEQ ID NO: 7 | SEQ ID NO: 2 | SEQ ID NO: 1 |
| 3 | SEQ ID NO: 8 | SEQ ID NO: 7 | SEQ ID NO: 4 | SEQ ID NO: 3 |
| 4 | SEQ ID NO: 8 | SEQ ID NO: 7 | SEQ ID NO: 6 | SEQ ID NO: 5 |
| 5 | SEQ ID NO: 8 | SEQ ID NO: 7 | SEQ ID NO: 4 | SEQ ID NO: 5 |
| 6 | SEQ ID NO: 8 | SEQ ID NO: 7 | SEQ ID NO: 6 | SEQ ID NO: 3 |
| 7 | SEQ ID NO: 4 | SEQ ID NO: 3 | SEQ ID NO: 8 | SEQ ID NO: 7 |
| 8 | SEQ ID NO: 4 | SEQ ID NO: 5 | SEQ ID NO: 8 | SEQ ID NO: 7 |

TABLE 1-continued

Exemplary combinations of sequences for VL1, VH1, VL2, and VH2.

| Combination Number | VL1 sequence | VH1 sequence | VL2 sequence | VH2 sequence |
|---|---|---|---|---|
| 9 | SEQ ID NO: 6 | SEQ ID NO: 3 | SEQ ID NO: 8 | SEQ ID NO: 7 |
| 10 | SEQ ID NO: 6 | SEQ ID NO: 5 | SEQ ID NO: 8 | SEQ ID NO: 7 |

In some embodiments, the compound comprises a VL1 sequence comprising a first light chain CDR1, CDR2, and CDR3 and a VH1 sequence comprising a first heavy chain CDR1, CDR2, and CDR3, a VL2 sequence comprising a second light chain CDR1, CDR2 and CDR3, and a VH2 sequence comprising a second heavy chain CDR1, CDR2, and CDR3. In some embodiments, the CDRs are the CDRs of one or more VL1, VH1, VL2, and VH2 sequences provided in Table 1 or Table 2A. Exemplary light chain and heavy chain CDR sequences for the VL1, VH1, VL2, and VH2 sequences provided in Table 1 are shown below:

```
SEQ ID NO: 1 CDRs:
                                         (SEQ ID NO: 146)
DYAMH (CDR1), (SEQ ID NO: 147)
AITWNSGHIDYADSVEG (CDR2), (SEQ ID NO: 148)
VSYLSTASSLDY (CDR3)

SEQ ID NO: 2 CDRs:
                                         (SEQ ID NO: 149)
RASQGIRNYLA (CDR1), (SEQ ID NO: 150)
AASTLQS (CDR2), (SEQ ID NO: 151)
QRYNRAPYT (CDR3)

SEQ ID NO: 3 and SEQ ID NO: 5 CDRs:
                                         (SEQ ID NO: 152)
SYAMH (CDR1), (SEQ ID NO: 153)
FMSYDGSNKKYADSVKG (CDR2), (SEQ ID NO: 154)
NYYYYGMDV (CDR3)

SEQ ID NO: 4 and SEQ ID NO: 6 CDRs:
                                         (SEQ ID NO: 155)
RASQSVYSYLA (CDR1), (SEQ ID NO: 156)
DASNRAT (CDR2), (SEQ ID NO: 157)
QQRSNWPPFT (CDR3)

SEQ ID NO: 7 CDRs:
                                         (SEQ ID NO: 158)
DQTIH (CDR1), (SEQ ID NO: 159)
YIYPRDDSPKYNENFKG (CDR2), (SEQ ID NO: 160)
PDRSGYAWFIY (CDR3)

SEQ ID NO: 8 CDRs:
                                         (SEQ ID NO: 161)
KASRDVAIAVA (CDR1), (SEQ ID NO: 162)
WASTRHT (CDR2), (SEQ ID NO: 163)
HQYSSYPFT (CDR3)
```

In some embodiments, the compound comprises a VH1, VL1, VH2, and/or VL2 that comprises a sequence that is at least 80% (e.g., 85%, 90%, 95%, 96%, 97%, 98%, or 99%) identical to a sequence described in Table 1. The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the compound comprises a VH1, VL1, VH2, and/or VL2 that comprises a sequence comprising one or more (e.g., 1, 2, 3, 4, 5, 6, 7, 8, 9, 10 or more) mutations in a sequence described in Table 1. Such mutations can be conservative amino acid substitutions. As used herein, a "conservative amino acid substitution" refers to an amino acid substitution that does not alter the relative charge or size characteristics of the protein in which the amino acid substitution is made. Conservative substitutions of amino acids include, for example, substitutions made amongst amino acids within the following groups: (a) M, I, L, V; (b) F, Y, W; (c) K, R, H; (d) A, G; (e) S, T; (f) Q, N; and (g) E, D.

The amino acid sequences of the hinge region, CH2 and CH3 of the compound (and optionally the CH1 and CL, if the compound contains such regions) may be derived from any appropriate source, e.g., a constant region of an antibody such as an IgG1, IgG2, IgG3, or IgG4. Antibody heavy and light chain constant regions amino acid sequences are well known in the art, e.g., those provided in the IMGT database (www.imgt.org) or at www.vbase2.org/vbstat.php., both of which are incorporated by reference herein. In some embodiments, the amino acid sequences of the CH2 and CH3 are derived from an IgG1 or an IgG4 (e.g., SEQ ID NO: 39 or 37). In some embodiments, the CL comprises the amino acid sequence of a kappa CL or a lambda CL. In some embodiments, the hinge region comprises the amino acid sequence EPKSCDKTHTCPPCP (SEQ ID NO:40).

In some embodiments, the CH2 and/or CH3 of the compound (and optionally the CH1 and CL, if the compound contains such regions) may comprise one or more amino acid substitutions that differ from a wild type CH2 or CH3, e.g., one or more amino acid substitutions in a wild type IgG1 CH2 or CH3 or one or more amino acid substitutions in a wild type IgG4 CH2 or CH3 (SEQ ID NO: 39 provides an exemplary wild-type IgG1). Such substitutions are known in the art (see, e.g., U.S. Pat. Nos. 7,704,497, 7,083,784, 6,821,505, 8,323,962, 6,737,056, and 7,416,727).

In some embodiments, the CH2 comprises an amino acid substitution at 234, 235, 252, 254, and/or 256, numbered according to the EU index as in Kabat for a conventional antibody (Kabat et al. Sequences of Proteins of Immunological Interest, U.S. Department of Health and Human Services, 1991, which is incorporated by reference herein in its entirety). It is to be understood that all amino acid positions described herein refer to the numbering of the EU index as in Kabat for a conventional antibody. In some embodiments, the CH2 comprises an amino acid substitution at position 252, 254, and/or 256. In some embodiments, the amino acid at position 252 is tyrosine, phenylalanine, serine, tryptophan, or threonine. In some embodiments, the amino acid at position 254 is threonine. In some embodiments, the amino acid at position 254 is serine, arginine, glutamine, glutamic acid, or aspartic acid. In some embodiments, the CH2 comprises a tyrosine at position 252, a threonine at position 254 and a glutamic acid a position 256 (referred to herein as a YTE mutant). In some embodiments, the CH2 comprises an amino acid substitution at position 234 and/or 235. In some embodiments, the CH2 comprises an alanine at position 234 and an alanine at position 235, also referred to herein as KO mutant. In some embodiments, the CH2 comprises a tyrosine at position 252, a threonine at position 254, a glutamic acid a position 256, an alanine at position 234 and an alanine at position 235, also referred to herein as KO-YTE mutant.

In some embodiments, one or more linkers may be used to connect domains/regions together on the first and/or second polypeptide. For example, the first polypeptide may comprise a linker between the VL1 and VH2. If the first polypeptide comprises a CH1, the first polypeptide may comprise a linker between the VL1 or VH2 (depending on the configuration discussed above) and the CH1 (e.g., VL1-linker-CH1 or VH2-linker-CH1). In another example, the second polypeptide may comprise a linker between the VL2 and VH1. If the second polypeptide further comprises a CL, the second polypeptide may further comprise a linker between the VL2 or VH1 (depending on the configuration discussed above) and the CL (e.g., VL2-linker-CL or VH1-linker-CL). It is to be understood that any number of linkers may be used to connect any domain or region to any other another domain or region on the first polypeptide and/or that any number of linkers may be used to connect any domain or region to any other another domain or region on the second polypeptide.

Any suitable linker known in the art is contemplated for use herein. In some embodiments, the linker is a peptide linker. In some embodiments, the peptide linker comprises at least two amino acids, e.g., 2, 3, 4, 5, 6, 7, 8, 9, 10 or more amino acids. In some embodiments, the peptide linker is no more than 50, 40, 30, 25, 20, 19, 18, 17, 16, 15, 14, 13, 12, 11, 10, 9, 8, 7, 6, 5, 4, 3, or 2 amino acids in length. In some embodiments, the peptide linker is between 2 and 50, 2 and 40, 2 and 30, 2 and 20, 2 and 10, 2 and 9, 2 and 8, 2 and 7, or 2 and 6 amino acids in length. In some embodiments, the peptide linker comprises the amino acid sequence GGGSGGG (SEQ ID NO:9), LGGGSG (SEQ ID NO:10), FNRGES (SEQ ID NO:11), VEPKSS (SEQ ID NO:12), or a combination thereof. In some embodiments, the peptide linker may comprise multiple copies of a linker sequence, e.g., multiple copies of the sequence GGGSGGG (SEQ ID NO:9), LGGGSG (SEQ ID NO:10), FNRGES (SEQ ID NO:11), VEPKSS (SEQ ID NO:12), or a combination thereof.

In some embodiments, the compound comprises two first polypeptides and two second polypeptides. In some embodiments, the CH2 and CH3 of one of the first polypeptides associates with the CH2 and CH3 of the other of the first polypeptides to form a tetravalent molecule (e.g., the two first polypeptides dimerize through associations between their respective CH2 and CH3 domains to form a tetravalent molecule comprising two binding sites specific for the first target protein and two binding sites specific for the second target protein). If the first polypeptide further comprises a CH1 domain, the CH1 domain may also participate in formation of a tetravalent molecule (e.g., the two first polypeptides dimerize through associations between their respective CH1, CH2 and CH3 domains to form a tetravalent molecule comprising two binding sites for the first target protein and two binding sites for the second target protein). In some embodiments, the two first polypeptides are associated together via at least one disulfide bond.

Also contemplated herein are other compounds that compete for binding with a compound as described herein, e.g., a test compound that competes with a compound as described herein for binding to TNF-alpha and IL23A. In some embodiments, the test compound may have at least 80%, 85%, 90%, 95%, 96%, 97%, 98%, or 99% sequence identity with a compound as described herein. Competitive binding may be determined using any assay known in the art, e.g., equilibrium binding, ELISA, surface plasmon resonance, or spectroscopy.

In some embodiments, the compound described herein specifically binds to both TNF-alpha and IL23A. A compound that "specifically binds" to an antigen or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. A compound "specifically binds" to a target antigen or epitope if it binds with greater affinity, avidity, more readily, and/or with greater duration than it binds to other substances. For example, a compound that specifically (or preferentially) binds to an antigen (e.g., TNF-alpha or IL23A) or an antigenic epitope therein is a compound that binds this target antigen with greater affinity, avidity, more readily, and/or with greater duration than it binds to other antigens or other epitopes in the same antigen. It is also understood by reading this definition that, for example, a compound that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding. In some examples, a compound that "specifically binds" to a target antigen or an epitope thereof may not bind to other antigens or other epitopes in the same antigen.

In some embodiments, a compound as described herein has a suitable binding affinity for TNF-alpha and IL23 or antigenic epitopes thereof. As used herein, "binding affinity" refers to the apparent association constant or $K_A$. The $K_A$ is the reciprocal of the dissociation constant ($K_D$). The compound described herein may have a binding affinity ($K_D$) of at least $10^{-5}$, $10^{-6}$, $10^{-7}$, $10^{-8}$, $10^{-9}$, $10^{-10}$, $10^{-11}$, $10^{-12}$ M or lower for one or both of the target antigens or antigenic epitopes. An increased binding affinity corresponds to a decreased $K_D$. In some embodiments, the compound described herein has a binding affinity ($K_D$) of at least $10^{-11}$M or lower for one or both of the target antigens or antigenic epitopes. Higher affinity binding of a compound for a first antigen and a second antigen relative to a third antigen can be indicated by a higher $K_A$ (or a smaller numerical value $K_D$) for binding the first antigen and second antigen than the $K_A$ (or numerical value $K_D$) for binding the third antigen. In such cases, the compound has specificity for the first antigen and second antigen (e.g., a first protein in a first conformation or mimic thereof and a second protein in a first conformation or mimic thereof) relative to the third antigen (e.g., the same first or second protein in a second conformation or mimic thereof; or a third protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity (or binding specificity) can be determined by a variety of methods including, equilibrium binding, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

[Bound]=[*N*][Free]/(*Kd*+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the compound comprises a first polypeptide and a second polypeptide as defined in Table 2A. In some embodiments, the compound comprises:

(i) a first polypeptide comprises the amino acid sequence of SEQ ID NO:13 and a second polypeptide comprises the amino acid sequence of SEQ ID NO:14;
(ii) a first polypeptide comprises the amino acid sequence of SEQ ID NO:15 and a second polypeptide comprises the amino acid sequence of SEQ ID NO:16;
(iii) a first polypeptide comprises the amino acid sequence of SEQ ID NO:17 and a second polypeptide comprises the amino acid sequence of SEQ ID NO:18;
(iv) a first polypeptide comprises the amino acid sequence of SEQ ID NO:19 and a second polypeptide comprises the amino acid sequence of SEQ ID NO:20;
(v) a first polypeptide comprises the amino acid sequence of SEQ ID NO:21 and a second polypeptide comprises the amino acid sequence of SEQ ID NO:22;
(vi) a first polypeptide comprises the amino acid sequence of SEQ ID NO:23 and a second polypeptide comprises the amino acid sequence of SEQ ID NO:24;
(vii) a first polypeptide comprises the amino acid sequence of SEQ ID NO:25 and a second polypeptide comprises the amino acid sequence of SEQ ID NO:26;
(viii) a first polypeptide comprises the amino acid sequence of SEQ ID NO:27 and a second polypeptide comprises the amino acid sequence of SEQ ID NO:28;
(ix) a first polypeptide comprises the amino acid sequence of SEQ ID NO:29 and a second polypeptide comprises the amino acid sequence of SEQ ID NO:30;
(x) a first polypeptide comprises the amino acid sequence of SEQ ID NO:31 and a second polypeptide comprises the amino acid sequence of SEQ ID NO:32;
(xi) a first polypeptide comprises the amino acid sequence of SEQ ID NO:33 and a second polypeptide comprises the amino acid sequence of SEQ ID NO:34;
(xii) a first polypeptide comprises the amino acid sequence of SEQ ID NO:35 and a second polypeptide comprises the amino acid sequence of SEQ ID NO:36;
(xiii) a first polypeptide comprises the amino acid sequence of SEQ ID NO:44 and a second polypeptide comprises the amino acid sequence of SEQ ID NO:45;
(xiv) a first polypeptide comprises the amino acid sequence of SEQ ID NO:46 and a second polypeptide comprises the amino acid sequence of SEQ ID NO:47;
(xv) a first polypeptide comprises the amino acid sequence of SEQ ID NO:48 and a second polypeptide comprises the amino acid sequence of SEQ ID NO:49;
(xvi) a first polypeptide comprises the amino acid sequence of SEQ ID NO:50 and a second polypeptide comprises the amino acid sequence of SEQ ID NO:51;
(xvii) a first polypeptide comprises the amino acid sequence of SEQ ID NO:52 and a second polypeptide comprises the amino acid sequence of SEQ ID NO:53;
(xviii) a first polypeptide comprises the amino acid sequence of SEQ ID NO:54 and a second polypeptide comprises the amino acid sequence of SEQ ID NO:55;
(xix) a first polypeptide comprises the amino acid sequence of SEQ ID NO:56 and a second polypeptide comprises the amino acid sequence of SEQ ID NO:57;
(xx) a first polypeptide comprises the amino acid sequence of SEQ ID NO:58 and a second polypeptide comprises the amino acid sequence of SEQ ID NO:59;
(xxi) a first polypeptide comprises the amino acid sequence of SEQ ID NO:60 and a second polypeptide comprises the amino acid sequence of SEQ ID NO:61;
(xxii) a first polypeptide comprises the amino acid sequence of SEQ ID NO:62 and a second polypeptide comprises the amino acid sequence of SEQ ID NO:63;
(xxiii) a first polypeptide comprises the amino acid sequence of SEQ ID NO:64 and a second polypeptide comprises the amino acid sequence of SEQ ID NO:65;
(xxiv) a first polypeptide comprises the amino acid sequence of SEQ ID NO:66 and a second polypeptide comprises the amino acid sequence of SEQ ID NO:67;
(xxv) a first polypeptide comprises the amino acid sequence of SEQ ID NO:68 and a second polypeptide comprises the amino acid sequence of SEQ ID NO:69;
(xxvi) a first polypeptide comprises the amino acid sequence of SEQ ID NO:70 and a second polypeptide comprises the amino acid sequence of SEQ ID NO:71;
(xxvii) a first polypeptide comprises the amino acid sequence of SEQ ID NO:72 and a second polypeptide comprises the amino acid sequence of SEQ ID NO:73;
(xxviii) a first polypeptide comprises the amino acid sequence of SEQ ID NO:74 and a second polypeptide comprises the amino acid sequence of SEQ ID NO:75;
(xxix) a first polypeptide comprises the amino acid sequence of SEQ ID NO:76 and a second polypeptide comprises the amino acid sequence of SEQ ID NO:77;
(xxx) a first polypeptide comprises the amino acid sequence of SEQ ID NO:78 and a second polypeptide comprises the amino acid sequence of SEQ ID NO:79;
(xxxi) a first polypeptide comprises the amino acid sequence of SEQ ID NO:80 and a second polypeptide comprises the amino acid sequence of SEQ ID NO:81;

(xxxii) a first polypeptide comprises the amino acid sequence of SEQ ID NO:82 and a second polypeptide comprises the amino acid sequence of SEQ ID NO:83;
(xxxiii) a first polypeptide comprises the amino acid sequence of SEQ ID NO:84 and a second polypeptide comprises the amino acid sequence of SEQ ID NO:85;
(xxxiv) a first polypeptide comprises the amino acid sequence of SEQ ID NO:86 and a second polypeptide comprises the amino acid sequence of SEQ ID NO:87;
(xxxv) a first polypeptide comprises the amino acid sequence of SEQ ID NO:88 and a second polypeptide comprises the amino acid sequence of SEQ ID NO:89;
(xxxvi) a first polypeptide comprises the amino acid sequence of SEQ ID NO:90 and a second polypeptide comprises the amino acid sequence of SEQ ID NO:91;
(xxxvii) a first polypeptide comprises the amino acid sequence of SEQ ID NO:92 and a second polypeptide comprises the amino acid sequence of SEQ ID NO:93;
(xxxviii) a first polypeptide comprises the amino acid sequence of SEQ ID NO:94 and a second polypeptide comprises the amino acid sequence of SEQ ID NO:95;
(xxxix) a first polypeptide comprises the amino acid sequence of SEQ ID NO:96 and a second polypeptide comprises the amino acid sequence of SEQ ID NO:97;
(xl) a first polypeptide comprises the amino acid sequence of SEQ ID NO:98 and a second polypeptide comprises the amino acid sequence of SEQ ID NO:99;
(xli) a first polypeptide comprises the amino acid sequence of SEQ ID NO:100 and a second polypeptide comprises the amino acid sequence of SEQ ID NO:101;
(xlii) a first polypeptide comprises the amino acid sequence of SEQ ID NO:102 and a second polypeptide comprises the amino acid sequence of SEQ ID NO:103;
(xliii) a first polypeptide comprises the amino acid sequence of SEQ ID NO:104 and a second polypeptide comprises the amino acid sequence of SEQ ID NO:105;
(xliv) a first polypeptide comprises the amino acid sequence of SEQ ID NO:106 and a second polypeptide comprises the amino acid sequence of SEQ ID NO:107;
(xlv) a first polypeptide comprises the amino acid sequence of SEQ ID NO:108 and a second polypeptide comprises the amino acid sequence of SEQ ID NO:109;
(xlvi) a first polypeptide comprises the amino acid sequence of SEQ ID NO:110 and a second polypeptide comprises the amino acid sequence of SEQ ID NO:111;
(xlvii) a first polypeptide comprises the amino acid sequence of SEQ ID NO:112 and a second polypeptide comprises the amino acid sequence of SEQ ID NO:113;
(xlviii) a first polypeptide comprises the amino acid sequence of SEQ ID NO:114 and a second polypeptide comprises the amino acid sequence of SEQ ID NO:115;
(xlix) a first polypeptide comprises the amino acid sequence of SEQ ID NO:116 and a second polypeptide comprises the amino acid sequence of SEQ ID NO:117;
(l) a first polypeptide comprises the amino acid sequence of SEQ ID NO:118 and a second polypeptide comprises the amino acid sequence of SEQ ID NO:119;
(li) a first polypeptide comprises the amino acid sequence of SEQ ID NO:120 and a second polypeptide comprises the amino acid sequence of SEQ ID NO:121;
(lii) a first polypeptide comprises the amino acid sequence of SEQ ID NO:122 and a second polypeptide comprises the amino acid sequence of SEQ ID NO:123;
(liii) a first polypeptide comprises the amino acid sequence of SEQ ID NO:124 and a second polypeptide comprises the amino acid sequence of SEQ ID NO:125;
(liv) a first polypeptide comprises the amino acid sequence of SEQ ID NO:126 and a second polypeptide comprises the amino acid sequence of SEQ ID NO:127;
(lv) a first polypeptide comprises the amino acid sequence of SEQ ID NO:128 and a second polypeptide comprises the amino acid sequence of SEQ ID NO:129;
(lvi) a first polypeptide comprises the amino acid sequence of SEQ ID NO:130 and a second polypeptide comprises the amino acid sequence of SEQ ID NO:131;
(lvii) a first polypeptide comprises the amino acid sequence of SEQ ID NO:132 and a second polypeptide comprises the amino acid sequence of SEQ ID NO:133;
(lviii) a first polypeptide comprises the amino acid sequence of SEQ ID NO:134 and a second polypeptide comprises the amino acid sequence of SEQ ID NO:135;
(lix) a first polypeptide comprises the amino acid sequence of SEQ ID NO:136 and a second polypeptide comprises the amino acid sequence of SEQ ID NO:137;
(lx) a first polypeptide comprises the amino acid sequence of SEQ ID NO:138 and a second polypeptide comprises the amino acid sequence of SEQ ID NO:139;
(lxi) a first polypeptide comprises the amino acid sequence of SEQ ID NO:140 and a second polypeptide comprises the amino acid sequence of SEQ ID NO:141; or
(lxii) a first polypeptide comprises the amino acid sequence of SEQ ID NO:142 and a second polypeptide comprises the amino acid sequence of SEQ ID NO:143.

In some embodiments, the compound comprises:
(i) a first polypeptide comprises the amino acid sequence of SEQ ID NO:13 and a second polypeptide comprises the amino acid sequence of SEQ ID NO:14;
(ii) a first polypeptide comprises the amino acid sequence of SEQ ID NO:15 and a second polypeptide comprises the amino acid sequence of SEQ ID NO:16;
(iii) a first polypeptide comprises the amino acid sequence of SEQ ID NO:17 and a second polypeptide comprises the amino acid sequence of SEQ ID NO:18;
(iv) a first polypeptide comprises the amino acid sequence of SEQ ID NO:19 and a second polypeptide comprises the amino acid sequence of SEQ ID NO:20;
(v) a first polypeptide comprises the amino acid sequence of SEQ ID NO:21 and a second polypeptide comprises the amino acid sequence of SEQ ID NO:22;
(vi) a first polypeptide comprises the amino acid sequence of SEQ ID NO:23 and a second polypeptide comprises the amino acid sequence of SEQ ID NO:24;
(vii) a first polypeptide comprises the amino acid sequence of SEQ ID NO:25 and a second polypeptide comprises the amino acid sequence of SEQ ID NO:26;
(viii) a first polypeptide comprises the amino acid sequence of SEQ ID NO:27 and a second polypeptide comprises the amino acid sequence of SEQ ID NO:28;
(ix) a first polypeptide comprises the amino acid sequence of SEQ ID NO:29 and a second polypeptide comprises the amino acid sequence of SEQ ID NO:30;
(x) a first polypeptide comprises the amino acid sequence of SEQ ID NO:31 and a second polypeptide comprises the amino acid sequence of SEQ ID NO:32;
(xi) a first polypeptide comprises the amino acid sequence of SEQ ID NO:33 and a second polypeptide comprises the amino acid sequence of SEQ ID NO:34; or
(xii) a first polypeptide comprises the amino acid sequence of SEQ ID NO:35 and a second polypeptide comprises the amino acid sequence of SEQ ID NO:36.

Methods of producing compounds, nucleic acids, vectors, and cells

Aspects of the disclosure also include nucleic acids that encode compounds described herein or polypeptides described herein (e.g., first or second polypeptides described herein), which may be encoded together or separately. The polynucleotides encoding the compounds described herein or polypeptides described herein may be obtained, and the nucleotide sequence of the polynucleotides determined, by any method known in the art.

In some embodiments, the nucleic acid is comprised within a vector, such as an expression vector. In some embodiments, the vector comprises a promoter operably linked to the nucleic acid.

A variety of promoters can be used for expression of the compounds described herein or polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, E. coli lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the compounds described herein. In some embodiments, the expression of the compounds described herein is regulated by a constitutive, an inducible or a tissue-specific promoter.

The host cells used to express the compounds described herein or polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667).

A variety of host-expression vector systems may be utilized to express the compounds described herein or polypeptides described herein. Such host-expression systems represent vehicles by which the coding sequences of the compounds described herein or polypeptides described herein may be produced and subsequently purified, but also represent cells which may, when transformed or transfected with the appropriate nucleotide coding sequences, express the compounds described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the compounds described herein; yeast (e.g., *Saccharomyces pichia*) transformed with recombinant yeast expression vectors containing sequences encoding the compounds described herein; insect cell systems infected with recombinant virus expression vectors (e.g., baclovirus) containing the sequences encoding the compounds described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules compounds described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the compound being expressed. For example, when a large quantity of such a protein is to be produced, for the generation of pharmaceutical compositions of compounds described herein, vectors which direct the expression of high levels of fusion protein products that are readily purified may be desirable. Such vectors include, but are not limited, to the *E. coli* expression vector pUR278 (Rüther et al. (1983) "Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The lpp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-

5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the compounds described herein may be expressed as a single gene product (e.g., as a single polypeptide chain, i.e., as a polyprotein precursor), requiring proteolytic cleavage by native or recombinant cellular mechanisms to form separate polypeptides of the compounds described herein. The disclosure thus encompasses engineering a nucleic acid sequence to encode a polyprotein precursor molecule comprising the polypeptides of the compounds described herein, which includes coding sequences capable of directing post translational cleavage of said polyprotein precursor. Post-translational cleavage of the polyprotein precursor results in the polypeptides of the compounds described herein. The post translational cleavage of the precursor molecule comprising the polypeptides of the compounds described herein may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action). Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express compounds described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the compounds described herein. Such engineered cell lines may be particularly useful in screening and evaluation of compounds that interact directly or indirectly with the compounds described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk-, hgprt- or aprt- cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of compounds described herein or polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a compound described herein is amplifiable, increase in the level of inhibitor present in culture of host cell will increase the number of copies of the marker gene. Since the amplified region is associated with the nucleotide sequence of a compound described herein or a polypeptide described herein, production of the polypeptide will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors, the first vector encoding the first polypeptide of a compound described herein and the second vector encoding the second polypeptide of a compound described herein. The two vectors may contain identical selectable markers which enable equal expression of both polypeptides. Alternatively, a single vector may be used which encodes both polypeptides. The coding sequences for the polypeptides of compounds described herein may comprise cDNA or genomic DNA.

Once a compound described herein or polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the compound comprises an Fc domain (or portion thereof)), and sizing column chromatography), centrifugation, differential solubility, or by any other standard technique for the purification of polypeptides or antibodies.

Other aspects of the disclosure relate to a cell comprising a nucleic acid described herein or a vector described herein. The cell may be a prokaryotic or eukaryotic cell. In some embodiments, the cell in a mammalian cell. Exemplary cell types are described herein.

Yet other aspects of the disclosure relate to a method of producing a compound described herein or a polypeptide described herein (e.g., a first polypeptide or a second polypeptide), the method comprising obtaining a cell described herein and expressing nucleic acid described herein in said cell. In some embodiments, the method further comprises isolating and purifying a compound described herein or a polypeptide described herein.

Methods of treatment and compositions for use in medicine

Other aspects of the disclosure relate to methods of treatment and compositions for use in medicine. Non-limiting examples of compounds for use in such methods and composition are those that comprise:

(i) a first polypeptide comprises the amino acid sequence of SEQ ID NO:13 and a second polypeptide comprises the amino acid sequence of SEQ ID NO:14;

(ii) a first polypeptide comprises the amino acid sequence of SEQ ID NO:15 and a second polypeptide comprises the amino acid sequence of SEQ ID NO:16;

(iii) a first polypeptide comprises the amino acid sequence of SEQ ID NO:17 and a second polypeptide comprises the amino acid sequence of SEQ ID NO:18;

(iv) a first polypeptide comprises the amino acid sequence of SEQ ID NO:19 and a second polypeptide comprises the amino acid sequence of SEQ ID NO:20;

(v) a first polypeptide comprises the amino acid sequence of SEQ ID NO:21 and a second polypeptide comprises the amino acid sequence of SEQ ID NO:22;

(vi) a first polypeptide comprises the amino acid sequence of SEQ ID NO:23 and a second polypeptide comprises the amino acid sequence of SEQ ID NO:24;

(vii) a first polypeptide comprises the amino acid sequence of SEQ ID NO:25 and a second polypeptide comprises the amino acid sequence of SEQ ID NO:26;

(viii) a first polypeptide comprises the amino acid sequence of SEQ ID NO:27 and a second polypeptide comprises the amino acid sequence of SEQ ID NO:28;

(ix) a first polypeptide comprises the amino acid sequence of SEQ ID NO:29 and a second polypeptide comprises the amino acid sequence of SEQ ID NO:30;

(x) a first polypeptide comprises the amino acid sequence of SEQ ID NO:31 and a second polypeptide comprises the amino acid sequence of SEQ ID NO:32;

(xi) a first polypeptide comprises the amino acid sequence of SEQ ID NO:33 and a second polypeptide comprises the amino acid sequence of SEQ ID NO:34; or (xii) a first polypeptide comprises the amino acid sequence of SEQ ID NO:35 and a second polypeptide comprises the amino acid sequence of SEQ ID NO:36.

In some embodiments, the method of treatment or the use is a method of treating an autoimmune or an inflammatory disease or use in such a method. In some embodiments, the method comprises administering a compound described herein or a pharmaceutical composition comprising said compound to a subject, e.g., a subject having or at risk for having an autoimmune or an inflammatory disease.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human subject having, at risk for, or suspected of having a disease. A subject having a disease can be identified by routine medical examination, e.g., a physical examination, a laboratory test, an organ functional test, a CT scan, or an ultrasound. A subject suspected of having any of such a disease might show one or more symptoms of the disease. Signs and symptoms for diseases, e.g., autoimmune and inflammatory diseases, are well known to those of ordinary skill in the art. A subject at risk for the disease can be a subject having one or more of the risk factors for that disease.

Non-limiting examples of autoimmune diseases include rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, psoriatic arthritis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis.

Non-limiting examples of inflammatory diseases include including rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyasitis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis. In some embodiments, the autoimmune or inflammatory disease is Crohn's disease, ankylosing spondylitis, or psoriatic arthritis.

To practice a method disclosed herein, an effective amount of a compound or pharmaceutical composition described herein can be administered to a subject (e.g., a human) in need of the treatment. Various delivery systems are known and can be used to administer the compounds of the invention. Methods of administration include, but are not limited to, intradermal, intramuscular, intraperitoneal, intravenous, subcutaneous, intranasal, epidural, and oral routes. The compounds of the invention can be administered, for example by infusion, bolus or injection, and can be administered together with other biologically active agents such as anti-inflammatory agents. Administration can be systemic or local. In preferred embodiments, the administration is by subcutaneous injection. Formulations for such injections may be prepared in, for example, prefilled syringes that may be administered once every other week.

"An effective amount" as used herein refers to the amount of each compound required to confer therapeutic effect on the subject, either alone or in combination with one or more other compounds. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, compounds that are compatible with the human immune system, such as compounds comprising regions from humanized antibodies or fully human antibodies, may be used to prolong half-life of the compound and to prevent the compound being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a compound may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the compound used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the compound (such as the half-life of the compound, and other considerations well known in the art).

For the purpose of the present disclosure, the appropriate dosage of a compound as described herein will depend on the specific compound (or compositions thereof) employed, the formulation and route of administration, the type and severity of the disease, whether the compound is administered for preventive or therapeutic purposes, previous therapy, the subject's clinical history and response to the antagonist, and the discretion of the attending physician. Typically the clinician will administer a compound until a dosage is reached that achieves the desired result. Administration of one or more compounds can be continuous or intermittent, depending, for example, upon the recipient's physiological condition, whether the purpose of the administration is therapeutic or prophylactic, and other factors known to skilled practitioners. The administration of a compound may be essentially continuous over a preselected period of time or may be in a series of spaced dose, e.g., either before, during, or after developing a disease.

As used herein, the term "treating" refers to the application or administration of a compound or composition including the compound to a subject, who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

In some embodiments, the compound described herein is administered to a subject in need of the treatment at an amount sufficient to inhibit the activity of one or both of TNF-alpha or IL23A by at least 20% (e.g., 30%, 40%, 50%, 60%, 70%, 80%, 90% or greater) in vivo or in vitro. Methods for determining the inhibitory capability of a compound are known in the art. Exemplary TNF-alpha and IL23A inhibition assays are provided in the Examples.

Conventional methods, known to those of ordinary skill in the art of medicine, can be used to administer the compound or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.
Pharmaceutical compositions Yet other aspects of the disclosure relate to pharmaceutical compositions comprising a compound described herein. A composition comprising a compound of the invention (e.g., compounds specific for both TNF-alpha and IL23A) can be administered to a subject having or at risk of having an autoimmune or an inflammatory disease. The invention further provides for the use of a compound of the invention in the manufacture of a medicament for treatment of an autoimmune or an inflammatory disease. The compounds can be administered either alone or in combination with other compositions in the prevention or treatment of an autoimmune or an inflammatory disease. Non-limiting examples of compounds of the invention for use in such pharmaceutical compositions are those that comprise:

(i) a first polypeptide comprises the amino acid sequence of SEQ ID NO:13 and a second polypeptide comprises the amino acid sequence of SEQ ID NO:14;
(ii) a first polypeptide comprises the amino acid sequence of SEQ ID NO:15 and a second polypeptide comprises the amino acid sequence of SEQ ID NO:16;
(iii) a first polypeptide comprises the amino acid sequence of SEQ ID NO:17 and a second polypeptide comprises the amino acid sequence of SEQ ID NO:18;
(iv) a first polypeptide comprises the amino acid sequence of SEQ ID NO:19 and a second polypeptide comprises the amino acid sequence of SEQ ID NO:20;
(v) a first polypeptide comprises the amino acid sequence of SEQ ID NO:21 and a second polypeptide comprises the amino acid sequence of SEQ ID NO:22;
(vi) a first polypeptide comprises the amino acid sequence of SEQ ID NO:23 and a second polypeptide comprises the amino acid sequence of SEQ ID NO:24;
(vii) a first polypeptide comprises the amino acid sequence of SEQ ID NO:25 and a second polypeptide comprises the amino acid sequence of SEQ ID NO:26;
(viii) a first polypeptide comprises the amino acid sequence of SEQ ID NO:27 and a second polypeptide comprises the amino acid sequence of SEQ ID NO:28;
(ix) a first polypeptide comprises the amino acid sequence of SEQ ID NO:29 and a second polypeptide comprises the amino acid sequence of SEQ ID NO:30;
(x) a first polypeptide comprises the amino acid sequence of SEQ ID NO:31 and a second polypeptide comprises the amino acid sequence of SEQ ID NO:32;
(xi) a first polypeptide comprises the amino acid sequence of SEQ ID NO:33 and a second polypeptide comprises the amino acid sequence of SEQ ID NO:34; or
(xii) a first polypeptide comprises the amino acid sequence of SEQ ID NO:35 and a second polypeptide comprises the amino acid sequence of SEQ ID NO:36.

As used herein, the term "pharmaceutical composition" refers to the formulation of a compound described herein in combination with a pharmaceutically acceptable carrier. The pharmaceutical composition can further comprise additional agents (e.g. for specific delivery, increasing half-life, or other therapeutic compounds).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, a compound of the invention in a composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the compound of the invention does not absorb are used.

In other embodiments, the compounds of the invention are delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

Compounds of the invention can be administered as pharmaceutical compositions comprising a therapeutically effective amount of a binding agent and one or more pharmaceutically compatible ingredients.

In typical embodiments, the pharmaceutical composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Compounds can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethyl-sulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical compositions of this disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

In some embodiments, a compound described herein may be conjugated to a therapeutic moiety, e.g., an anti-inflammatory agent. Techniques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158.

Further, the pharmaceutical composition can be provided as a pharmaceutical kit comprising (a) a container containing a compound of the invention in lyophilized form and (b) a second container containing a pharmaceutically acceptable diluent (e.g., sterile water) for injection. The pharmaceutically acceptable diluent can be used for reconstitution or dilution of the lyophilized compound of the invention.

Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is a compound of the invention. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Construction of exemplary compounds targeting IL23A and TNF-alpha

Table 2A below provides exemplary compounds that bind to both IL23A and TNF-alpha that were utilized in the Examples below. These compounds were produced by recombinant methods known in the art (see, e.g., PCT Publications WO 2006/113665, WO 2008/157379, and WO 2010/080538, all of which are incorporated herein by reference). Briefly, plasmids encoding the first and second polypeptide for each compound were transfected together into CHO-S cells using FreeStyle MAX Reagent (CHO). The cells were cultured for 13-14 days and the compounds produced by the cells were purified using Protein-A chromatography. The compounds were further purified using a size exclusion chromatography.

TABLE 2A

Exemplary IL23A and TNF-alpha binding compounds

| Compound ID | Large Chain vL | Large Chain vH | Small Chain vL | Small Chain vH | Linker types | Isotype | SEQ ID NO: (1st/2nd) |
|---|---|---|---|---|---|---|---|
| Compound A | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | GS | IgG1KO-YTE | 13/14 |
| Compound B | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | VF | IgG1KO-YTE | 15/16 |
| Compound C | IL23A(1) VL (SEQ ID NO: 8) | TNFa(1) VH (SEQ ID NO: 1) | TNFa(1) VL (SEQ ID NO: 2) | IL23A(1) VH (SEQ ID NO: 7) | GS | IgG1KO-YTE | 17/18 |
| Compound D | IL23A(1) VL (SEQ ID NO: 8) | TNFa(1) VH (SEQ ID NO: 1) | TNFa(1) VL (SEQ ID NO: 2) | IL23A(1) VH (SEQ ID NO: 7) | VF | IgG1KO-YTE | 19/20 |
| Compound E | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | GS | IgG1KO-YTE | 21/22 |
| Compound F | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | VF | IgG1KO-YTE | 23/24 |
| Compound G | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG1KO-YTE | 25/26 |
| Compound H | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | VF | IgG1KO-YTE | 27/28 |
| Compound I | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | GS | IgG1KO-YTE | 29/30 |
| Compound J | IL23A(1) VL (SEQ | TNFa(3) VH (SEQ | TNFa(3) VL (SEQ | IL23A(1) VH | GS | IgG1KO-YTE | 31/32 |

TABLE 2A-continued

Exemplary IL23A and TNF-alpha binding compounds

| Compound ID | Large Chain vL | Large Chain vH | Small Chain vL | Small Chain vH | Linker types | Isotype | SEQ ID NO: (1st/2nd) |
|---|---|---|---|---|---|---|---|
| | ID NO: 8) | ID NO: 5) | ID NO: 6) | (SEQ ID NO: 7) | | | |
| Compound K | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | VF | IgG1KO-YTE | 33/34 |
| Compound L | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | VF | IgG1KO-YTE | 35/36 |
| Compound M | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | GS | IgG1KO | 44/45 |
| Compound N | IL23A(1) VL (SEQ ID NO: 8) | TNFa(1) VH (SEQ ID NO: 1) | TNFa(1) VL (SEQ ID NO: 2) | IL23A(1) VH (SEQ ID NO: 7) | VF | IgG1KO | 46/47 |
| Compound O | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | GS | IgG1KO | 48/49 |
| Compound P | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | VF | IgG1KO | 50/51 |
| Compound Q | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG4Pro | 52/53 |
| Compound R | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG4Pro-YTE | 54/55 |
| Compound S | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG4Pro | 56/57 |
| Compound T | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG4Pro-YTE | 58/59 |
| Compound U | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | VF | IgG1KO | 60/61 |
| Compound V | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | VF | IgG1WT | 62/63 |
| Compound W | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | VF | IgG4Pro | 64/65 |
| Compound X | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | VF | IgG4Pro-YTE | 66/67 |
| Compound Y | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | GS | IgG1WT | 68/69 |
| Compound Z | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | GS | IgG4Pro | 70/71 |
| Compound AA | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | GS | IgG4Pro-YTE | 72/73 |
| Compound AB | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | VF | IgG1WT | 74/75 |

TABLE 2A-continued

Exemplary IL23A and TNF-alpha binding compounds

| Compound ID | Large Chain vL | Large Chain vH | Small Chain vL | Small Chain vH | Linker types | Isotype | SEQ ID NO: (1st/2nd) |
|---|---|---|---|---|---|---|---|
| Compound AC | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | VF | IgG4Pro | 76/77 |
| Compound AD | IL23A(1) VL (SEQ ID NO: 8) | TNFa(2) VH (SEQ ID NO: 3) | TNFa(2) VL (SEQ ID NO: 4) | IL23A(1) VH (SEQ ID NO: 7) | VF | IgG4Pro-YTE | 78/79 |
| Compound AE | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | GS | IgG1KO | 80/81 |
| Compound AF | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | GS | IgG1WT | 82/83 |
| Compound AG | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | GS | IgG4Pro | 84/85 |
| Compound AH | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | GS | IgG4Pro-YTE | 86/87 |
| Compound AI | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | VF | IgG1KO | 88/89 |
| Compound AJ | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | VF | IgG1WT | 90/91 |
| Compound AK | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | VF | IgG4Pro | 92/93 |
| Compound AL | TNFa(3) VL (SEQ ID NO: 6) | IL23A(1) VH (SEQ ID NO: 7) | IL23A(1) VL (SEQ ID NO: 8) | TNFa(3) VH (SEQ ID NO: 5) | VF | IgG4Pro-YTE | 94/95 |
| Compound AM | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | GS | IgG1KO | 96/97 |
| Compound AN | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | GS | IgG1WT | 98/99 |
| Compound AO | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | GS | IgG4Pro | 100/101 |
| Compound AP | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | GS | IgG4Pro-YTE | 102/103 |
| Compound AQ | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | VF | IgG1KO | 104/105 |
| Compound AR | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | VF | IgG1WT | 106/107 |
| Compound AS | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | VF | IgG4Pro | 108/109 |

TABLE 2A-continued

Exemplary IL23A and TNF-alpha binding compounds

| Compound ID | Large Chain vL | Large Chain vH | Small Chain vL | Small Chain vH | Linker types | Isotype | SEQ ID NO: (1st/2nd) |
|---|---|---|---|---|---|---|---|
| Compound AT | IL23A(1) VL (SEQ ID NO: 8) | TNFa(3) VH (SEQ ID NO: 5) | TNFa(3) VL (SEQ ID NO: 6) | IL23A(1) VH (SEQ ID NO: 7) | VF | IgG4Pro-YTE | 110/111 |
| Compound AU | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG1KO | 112/113 |
| Compound AV | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | GS | IgG1WT | 114/115 |
| Compound AW | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | GS | IgG4Pro | 116/117 |
| Compound AX | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | GS | IgG4Pro-YTE | 118/119 |
| Compound AY | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | VF | IgG1KO | 120/121 |
| Compound AZ | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | VF | IgG1WT | 122/123 |
| Compound BA | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | VF | IgG4Pro | 124/125 |
| Compound BB | TNFa(1) VL (SEQ ID NO: 2) | IL23A(1) VH (SEQ ID NO: 7) | IL23A(1) VL (SEQ ID NO: 8) | TNFa(1) VH (SEQ ID NO: 1) | VF | IgG4Pro-YTE | 126/127 |
| Compound BC | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | GS | IgG1KO | 128/129 |
| Compound BD | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | GS | IgG1WT | 130/131 |
| Compound BE | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | GS | IgG4Pro | 132/133 |
| Compound BF | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | GS | IgG4Pro-YTE | 134/135 |
| Compound BG | TNFa(2) VL (SEQ ID NO: 4) | IL23A(1) VH (SEQ ID NO: 7) | IL23A(1) VL (SEQ ID NO: 8) | TNFa(2) VH (SEQ ID NO: 3) | GS | IgG1WT | 136/137 |
| Compound BH | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | VF | IgG1WT | 138/139 |
| Compound BI | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | VF | IgG4Pro | 140/141 |

TABLE 2A-continued

Exemplary IL23A and TNF-alpha binding compounds

| Compound ID | Large Chain vL | Large Chain vH | Small Chain vL | Small Chain vH | Linker types | Isotype | SEQ ID NO: (1st/2nd) |
|---|---|---|---|---|---|---|---|
| Compound BJ | IL23A(1) VL (SEQ ID NO: 8) | TNFa(1) VH (SEQ ID NO: 1) | TNFa(1) VL (SEQ ID NO: 2) | IL23A(1) VH (SEQ ID NO:7) | VF | IgG4Pro-YTE | 142/143 |

TNFa = TNF-alpha,
VL = variable domain light chain,
VH = variable domain heavy chain,
GS = GGGSGGGG (SEQ ID NO: 9), LGGGSG (SEQ ID NO: 10), or both,
VF = FNRGES (SEQ ID NO: 11), VEPKSS (SEQ ID NO: 12), or both,
IgG1WT = IgG1 wild type;
IgG1KO-YTE = IgG1 with a M252Y/S254T/T256E triple mutation in the Fc region and also comprising L234A/L235A mutations,
IgG4Pro-YTE = IgG4 with a M252Y/S254T/T256E triple mutation in the Fc region and also comprising S241P mutation,
IgG1KO = truncated Fc region comprising L234A/L235A mutations,
IgG4Pro = comprising S241P mutation.
$1^{st}$ = first polypeptide,
$2^{nd}$ = second polypeptide.
The numbering of mutations is Kabat numbering for a conventional antibody starting with the antibody convention at CH1.

The below control antibodies were also used for comparison purposes. The controls were monoclonal antibodies that targeted either TNFa or IL23.

TABLE 2B

| Control compounds | VH sequence | VL sequence |
|---|---|---|
| Control antibody 1 (TNFa monoclonal antibody) | TNFa(1) VH (SEQ ID NO: 1) | TNFa(1) VL (SEQ ID NO: 2) |
| Control antibody 2 (TNFa monoclonal antibody) | TNFa(2) VH (SEQ ID NO: 3) | TNFa(2) VL (SEQ ID NO: 4) |
| Control Antibody 3 (IL23 monoclonal antibody) | IL23A(1) VH (SEQ ID NO: 7) | IL23A(1) VL (SEQ ID NO: 8) |

Example 2

Surface Plasmon Resonance (SPR) affinity of exemplary compounds

Test compounds were analyzed by SPR to determine affinity for TNF-alpha and IL23A.

Materials and Methods

SPR experiments were performed on a ProteOn XPR36 instrument (Bio Rad). A GLM chip was preconditioned with sequential injections of 60 sec of 0.5% SDS, 50 mM NaOH, and 100 mM HCl at a flow rate of 30 μl/min both vertical and horizontal directions. The preconditioned GLM chip was then activated by an injection of EDC (76.7 mg/ml) and sulfo-NHS (21.7 mg/ml) mixture with ratio of 1:1 in 6 horizontal channels. Goat-anti-human IgG (GAHA) Fc gamma (Invitrogen) at a concentration of 30 μg/ml in 10 mM, pH 5.0 sodium acetate buffer was immobilized to 8,000 resonance units on the activated GLM chip in 6 horizontal channels. The chip was finally deactivated with 1 M ethanolamine HCl in 6 horizontal channels. The prepared GAHA chip was rotated to vertical direction to capture test compounds, over 5 vertical channels and the last channel was used as a column reference. The captured chip was then rotated again to the horizontal direction for binding. Linked human IL-23 (Boehringer Ingelheim Pharmaceuticals, Inc) with five concentrations, 10.0 nM, 5.00 nM, 2.50 nM, 1.25 nM and 0.625 nM, were injected horizontally over the test compound surfaces for 10 minutes at a flow rate of 40 μl/min in the following running buffer (Bio Rad): phosphate buffer saline (pH 7.4), 0.005% Tween 20. The dissociation was allowed for 2 hour. The GAHA surface was regenerated using short pulse injection (18 seconds) of 0.85% phosphoric acid (Bio Rad) at a flow rate of 100 μl/min both horizontal and vertical directions after 10 min association and 2 hr dissociation. The regenerated GAHA was ready for another binding cycle. Binding of compounds to human TNF-alpha or cynomologus TNF-alpha was done in similar way.

Results

The results in Table 3 show that both compounds tested were able to bind TNF-alpha and IL23 with a dissociation constant (KD) in the picomolar range.

TABLE 3

| Compound ID | KD to human TNF-alpha (pM) | KD to cynomologus TNF-alpha (pM) | KD to human IL23 (pM) |
|---|---|---|---|
| Compound A | 2.14 | 7.71 | 4.28 ± 2.03 |
| Compound E | 4.11 ± 0.68 | 37.1 ± 16.2 | 7.00 ± 6.92 |

Example 3

Flow Cytometry Assessment of Binding to Membrane Bound TNF-Alpha

Test compounds were assessed for their ability to dose dependently bind to cell lines transfected to express membrane bound TNF-alpha.

Material and Methods

All reagents were prepared in flow cytometry staining buffer (BioLegend). Membrane expressed TNF-alpha transfected cell lines (Jurkat and CHO) and parental cell lines were harvested from tissue culture vessels, washed, counted and resuspended to 1×10^6 cells/ml in flow cytometry staining buffer. One hundred microliters of the cell suspension was added to 96 well microtiter plates and placed on ice. Titrations of test compounds were prepared and 50 uL was added to the cells. After sixty minute incubation on ice, the cell+test compounds were washed and 50 uL of a secondary antibody (Jackson ImmunoResearch) was added. The samples were incubated in the dark, at 4 C, for 60 minutes, followed by washes. After a final wash the cells were resuspended in 60 uL of fixative (BD Bioscience). Median fluorescence was determined for each sample in a flow cytometer and plotted versus the concentration of the test sample. $E_{C50}$ values were calculated using the 4 Parameter Logistic enabled by the Excel add-in XLfit (Activity Base software, ID Business Solutions, Ltd.). The $EC_{50}$ values shown below are Geomeans calculated across multiple experiments for each test sample and are shown in Table 4.

Results

The results shown in Table 4 below demonstrate that the compounds tested bound to membrane bound TNF-alpha in a dose dependent manner.

TABLE 4

EC50 values for membrane bound TNF-alpha.

| Compound ID | mTNF-Jurkat Cell Binding $EC_{50}$ pM (Geomean) | mTNF-CHO Cell Binding $EC_{50}$ pM (Geomean) |
| --- | --- | --- |
| Compound M | 650 | 950 |
| Compound A | 910 | 890 |
| Compound O | 270 | 770 |
| Compound E | 200 | 450 |
| Control antibody 1 (TNFa) | 310 | 400 |
| Control antibody 2 (TNFa) | 230 | 310 |

Example 4

In Vitro L929 Cytotoxicity Assay

The compounds were tested for their ability to inhibit TNF-alpha induced cytotoxicity.

Methods and Materials

This protocol used the PrestoBlue™0 Cell Viability Reagent to determine cytotoxicity of recombinant human TNF-alpha. A more detailed protocol for the PrestoBlue Cell Viability Protocol can be downloaded from the Invitrogen website (Invitrogen.com). L929 cells were grown and harvested. $1.5 \times 10^4$ cells were transferred to each well of a 96-well plate for incubated overnight at 37° C. Serial dilutions of compounds were prepared starting at 5 nM in complete assay medium containing 10 μg/ml of actinomycin D and 1000 pg/ml of rhTNF-alpha. The positive controls contained 20 ng/ml rhTNF-alpha and 1 μg/ml actinomycin D. The negative control contained no TNF-alpha. 10 μL of the dilutions was added to corresponding wells and incubated overnight at 37° C. in a 5% CO2. PrestoBlue™ reagent was added to wells and the plate was incubated for 2 hour at 37° C. in a 5% CO2. The relative fluorescence unit of each well was measured using a Victor™×2 plate reader (excitation: 560 nm, emission: 590 nm). The fluorescent units (Y-axis) versus concentration of test compound (X-axis) were plotted and the $IC_{50}$ and $IC_{90}$ values of test compounds were calculated by using Graphpad software.

Results

The results in Table 5 show that the tested compounds were able to inhibit TNF-alpha induced cytotoxicity in a dose-dependent manner.

TABLE 5

| Compound ID | $IC_{50}$ $IC_{90}$ | L929 TNF Cytotox pM Geomean |
| --- | --- | --- |
| Compound M | $IC_{50}$ | 19 |
| Compound M | $IC_{90}$ | 55 |
| Compound A | $IC_{50}$ | 20 |
| Compound A | $IC_{90}$ | 67 |
| Compound N | $IC_{50}$ | 34 |
| Compound N | $IC_{90}$ | |
| Compound D | $IC_{50}$ | |
| Compound D | $IC_{90}$ | |
| Compound O | $IC_{50}$ | 4.2 |
| Compound O | $IC_{90}$ | 16 |
| Compound E | $IC_{50}$ | 4.1 |
| Compound E | $IC_{90}$ | 17 |
| Compound P | $IC_{50}$ | 3.4 |
| Compound P | $IC_{90}$ | 14 |
| Compound F | $IC_{50}$ | 2.5 |
| Compound F | $IC_{90}$ | 10 |
| Control antibody 1 (TNFa) | $IC_{50}$ | 62 |
| Control antibody 1 (TNFa) | $IC_{90}$ | 230 |
| Control antibody 2 (TNFa) | $IC_{50}$ | 20 |
| Control antibody 2 (TNFa) | $IC_{90}$ | 95 |

Example 5

Inhibition of TNF-alpha dependent IL-8 Release in HeLa Cells

Anti-TNF test samples were assessed for their ability to inhibit the TNF dependent release of IL8 from the human cell line, HeLa. The samples were tested against a high and low concentration of recombinant human TNF-alpha and a single (high) concentration of recombinant cynomolgus TNF-alpha.

Materials and Methods

Briefly, HeLa cells (ATCC) were harvested, washed, counted and resuspended to 4×10^5 cells/ml in a standard complete media of (v/v) 10% Fetal Bovine Serum with 1% Penicillin &Streptomycin (CM). One hundred microliters of the HeLa cell suspension was added to 96 well microtiter plates. Recombinant human TNF-alpha (R&D Systems) at two concentrations (147 nM or 4.4 nM) as well as generated recombinant cynomolgus TNF-alpha (Boehringer Ingelheim Pharmaceuticals, Inc.) (147 nM) were pre-incubated for 30 minutes at 37 C with CM alone or with titrations of test samples. After the pre-incubation of test sample+TNF-alpha, 100 ul of the mixture(s) was added to the cells and the test plates were incubated at 37 C with 5% $CO_2$-humidified air for 20 hours. Control samples received either CM (unstimulated controls) or recombinant TNF-alpha diluted in CM (stimulated controls). After the incubation, supernatants were assayed for IL8 in an ELISA kit (MesoScale Discovery) following the manufacturer's instructions. Interpolated IL8 pg/ml values were determined for each sample and converted to percent of control (POC). The POC was plotted versus concentration of the test sample and $IC_{50}$ and $IC_{90}$ values were calculated using a 4 Parameter Logistic Model enabled by the Excel add-in XLfit (Activity Base software, ID Business Solutions, Ltd.).

The test compounds were analyzed with respect to the $IC_{50}/IC_{90}$ as described above, and Geomeans were calculated across multiple experiments for each test sample and shown in Table 6.

Results

The results in Tables 6 show that the $IC_{50}$ and $IC_{90}$ Geomean values for the tested compounds were similar to the $IC_{50}$ and $IC_{90}$ Geomean values for Control Antibody 1 and Control antibody 2. The data demonstrates that the test compounds dose dependently inhibited the TNF-alpha induced IL-8 secretion with either human (at two concentrations tested) or cyno recombinant TNF-alpha.

TABLE 6

| Compound ID | $IC_{50}$ $IC_{90}$ | HeLa IL8 Lo-Hu-TNF pM Geomean | HeLa IL8 Hi-Hu-TNF pM Geomean | HeLa IL8 Cyno-TNF pM Geomean |
|---|---|---|---|---|
| Compound M | $IC_{50}$ | 7.9 | 260 | 150 |
| Compound M | $IC_{90}$ | 48 | 420 | 270 |
| Compound A | $IC_{50}$ | 8 | 280 | 120 |
| Compound A | $IC_{90}$ | 41 | 460 | 260 |
| Compound N | $IC_{50}$ | 9.2 | 350 | 170 |
| Compound N | $IC_{90}$ | 54 | 570 | 330 |
| Compound D | $IC_{50}$ | 11 | 380 | 190 |
| Compound D | $IC_{90}$ | 63 | 590 | 390 |
| Compound O | $IC_{50}$ | 9.9 | 430 | 300 |
| Compound O | $IC_{90}$ | 43 | 760 | 970 |
| Compound E | $IC_{50}$ | 9.2 | 320 | 180 |
| Compound E | $IC_{90}$ | 35 | 530 | 600 |
| Compound P | $IC_{50}$ | 9.2 | 410 | 210 |
| Compound P | $IC_{90}$ | 36 | 810 | 810 |
| Compound F | $IC_{50}$ | 7.9 | 350 | 190 |
| Compound F | $IC_{90}$ | 39 | 660 | 740 |
| Control antibody 1 (TNFa) | $IC_{50}$ | 34 | 330 | 170 |
| Control antibody 1 (TNFa) | $IC_{90}$ | 140 | 490 | 330 |
| Control antibody 2 (TNFa) | $IC_{50}$ | 11 | 290 | 280 |
| Control antibody 2 (TNFa) | $IC_{90}$ | 55 | 520 | 1200 |

Example 6

Inhibition of TNF-alpha dependent IL8 in whole blood

TNF is a potent inducer of IL8 release from human cells. Compounds were tested for their ability to inhibit TNF-alpha induced IL-8 release in whole blood samples.

Methods and Materials

Briefly 120 uL of heparinized human whole blood was added to each well in a 96 well microtiter plate. Assay reagents were prepared in a standard T cell media (TCM). Titrations of test samples were prepared at 10× concentrations and pre-incubated with a 10× concentration of human recombinant TNF (100 ng/ml, R&D Systems) for 1 hour at 37 C. After this pre-incubation, 30 ul of the cytokine/test compound mixture was added to the whole blood along with 30 uL of appropriate controls in TCM and incubated at 37 C with 5% $CO_2$-humidified air for 48 hours. Control samples received either TCM (unstimulated controls) or recombinant human TNF-alpha diluted in TCM (stimulated controls). After the incubation, supernatants were assayed for IL8 in an ELISA kit (MesoScale Discovery) following manufacturer's instructions. Interpolated IL8 pg/ml values were determined for each sample and converted to percent of control (POC). The POC was plotted versus concentration of the test sample and $IC_{50}$ and $IC_{90}$ values were calculated using a 4 Parameter Logistic Model enabled by the Excel add-in XLfit (Activity Base software, ID Business Solutions, Ltd.).

The test compounds were analyzed with respect to the $IC_{50}/IC_{90}$ as described above, and Geomeans were calculated across multiple experiments for each test sample and shown in Table 7.

Results

The results in Table 7 show that the $IC_{50}$ and $IC_{90}$ Geomean values for the tested compounds were similar to the $IC_{50}$ and $IC_{90}$ Geomean values for Control antibody 1 and control antibody 2. The data demonstrates that the test compounds dose dependently inhibited the TNF-alpha induced IL8 release in human whole blood.

TABLE 7

| Compound ID | $IC_{50}$ $IC_{90}$ | TNF-IL8 Whole Blood pM Geomean |
|---|---|---|
| Compound M | $IC_{50}$ | 380 |
| Compound M | $IC_{90}$ | 790 |
| Compound A | $IC_{50}$ | 360 |
| Compound A | $IC_{90}$ | 490 |
| Compound N | $IC_{50}$ | 270 |
| Compound N | $IC_{90}$ | 520 |
| Compound D | $IC_{50}$ | 560 |
| Compound D | $IC_{90}$ | 1100 |
| Compound O | $IC_{50}$ | 320 |
| Compound O | $IC_{90}$ | 470 |
| Compound E | $IC_{50}$ | 340 |
| Compound E | $IC_{90}$ | 610 |
| Compound P | $IC_{50}$ | 290 |
| Compound P | $IC_{90}$ | 420 |
| Compound F | $IC_{50}$ | 310 |
| Compound F | $IC_{90}$ | 450 |
| Control antibody 1 (TNFa) | $IC_{50}$ | 320 |
| Control antibody 1 (TNFa) | $IC_{90}$ | 490 |
| Control antibody 2 (TNFa) | $IC_{50}$ | 330 |
| Control antibody 2 (TNFa) | $IC_{90}$ | 600 |

Example 7

NF-kappaB and STAT3 phosphorylation assays

IL23 engagement with its heterodimeric receptor complex (IL12Rβ1-IL23R) results in the downstream phosphorylation of Signal transducer and activator of transcription 3 (STAT3). TNF engagement with its receptors (TNFR1/TNFR2) results in the downstream phosphorylation of nuclear factor of kappa light polypeptide gene enhancer in B-cells (NF-κB). Compounds were assessed for their ability to inhibit TNF-dependent phosphorylation of NF-κB in Jurkat cells, and IL23-dependent phosphorylation of STAT3 in DB cells.

Methods and Materials:

Briefly, cultures of Jurkat cells (ATCC) and DB cells (ATCC) growing in log phase were harvested, washed, counted and resuspended to 2×10^7 cells/mL in a standard complete media (CM; RPMI1640 with (v/v) 10% FCS and 1× Penicillin-Streptomycin (Invitrogen)). Titrations of test samples were prepared at 4× concentrations and pre-incubated with a mixture of 4× human recombinant IL23 (Boehringer Ingelheim Pharmaceuticals, Inc.) and recombinant human TNF (R&D Systems) for 1 hour at 37 C. After the pre-incubation of the test reagent+cytokine mixture, 100 μL of the mixture was added to wells containing 100 μL of cells in duplicate. Controls were setup as follows: 100 μL of the diluted TNF/IL23+100 μL combined cells (stimulated control), or 100 μL of CM+100 μL combined cells (unstimulated control). The assay plates were incubated for exactly 10 minutes at 37° C. with 5% $CO_2$-humidified air. After the incubation, cell lysates were prepared and p-NF-κB and p-STAT3 was assessed following the manufacturer's instructions (MesoScale Discovery). p-NF-κB and p-STAT-3 raw values were determined for each sample and converted to percent of control (POC). The POC was plotted (Y-axis) versus concentration of the test agent (X-axis). $IC_{50}$ and $IC_{90}$ values were calculated using the 4 Parameter Logistic Model enabled by the Excel add-in XLfit (Activity Base software, ID Business Solutions, Ltd.).

The test compounds were analyzed with respect to the $IC_{50}/IC_{90}$ as described above, and Geomeans were calculated across multiple experiments for each test sample and shown in Table 10. Note: this assay provides confidence that that the dual molecule is capable of neutralizing both downstream signaling events. The assay time point is optimal for the p-NF-κB signal only and therefore the calculated $IC_{50}/IC_{90}$ does not reflect the overall potencies in a quantitative manner.

Results

The results in Table 8 show that the test compounds were able to inhibit both TNF-alpha induced NF-kB phosphorylation as well as IL23 induced phosphorylation of STAT3 in DB cells.

TABLE 8

| Compound ID | $IC_{50}$ $IC_{90}$ | Dual Phospho Jurkat-pNf-Kb pM Geomean* | Dual Phospho DB-pSTAT3 pM Geomean* |
|---|---|---|---|
| Compound M | $IC_{50}$ | 290 | 190 |
| Compound M | $IC_{90}$ | 680 | 580 |
| Compound A | $IC_{50}$ | 300 | 200 |
| Compound A | $IC_{90}$ | 480 | 500 |
| Compound N | $IC_{50}$ | 300 | 210 |
| Compound N | $IC_{90}$ | 620 | 760 |
| Compound D | $IC_{50}$ | 270 | 170 |
| Compound D | $IC_{90}$ | 810 | 560 |
| Compound O | $IC_{50}$ | 210 | 210 |
| Compound O | $IC_{90}$ | 740 | 580 |
| Compound E | $IC_{50}$ | 260 | 230 |
| Compound E | $IC_{90}$ | 340 | 770 |
| Compound P | $IC_{50}$ | 290 | 340 |
| Compound P | $IC_{90}$ | 340 | 630 |
| Compound F | $IC_{50}$ | 280 | 360 |
| Compound F | $IC_{90}$ | 760 | 980 |
| Control antibody 1 (TNFa) | $IC_{50}$ | 360 | NA |
| Control antibody 1 (TNFa) | $IC_{90}$ | 660 | NA |
| Control antibody 2 (TNFa) | $IC_{50}$ | 260 | NA |
| Control antibody 2 (TNFa) | $IC_{90}$ | 420 | NA |
| Control antibody 3(IL23A) | $IC_{50}$ | NA | 89 |
| Control antibody 3(IL23A) | $IC_{90}$ | NA | 230 |

*Results are semi-quantitative and optimized more to the TNF readout. NA; No Activity Example 8

Inhibition of IL23 induced STAT3 phosphorylation in DB cells

IL23 engagement with its heterodimeric receptor complex (IL12Rβ1-IL23R) results in the downstream phosphorylation of Signal transducer and activator of transcription 3 (STAT3). Anti-IL23 test samples were assessed for their ability to inhibit the IL23 dependent phosphorylation in the human DB cell line.

Materials and Methods:

Briefly 100 uL of the human DB cell line (ATCC) grown in log phase was added to each well in a 96 well microtiter plate at a concentration of 1×10^7 cells/ml. Assay reagents were prepared in a complete media (CM; RPMI1640 with (v/v) 10% Fetal Calf Serum and 1× Penicillin-Streptomycin (Invitrogen)). Titrations of test samples were prepared at 4× concentrations and pre-incubated with a 4× concentration of human recombinant IL23 (Boehringer Ingelheim Pharmaceuticals, Inc.) for 1 hour at 37 C. After this pre-incubation, 100 ul of the cytokine/test sample mixture was added to the 100 uL of DB cells and incubated at 37 C with 5% $CO_2$-humidified air for 30 minutes. Control samples received either CM (unstimulated controls) or recombinant human IL23 diluted in CM (stimulated controls). After the incubation, cell lysates were prepared and pSTAT3 was assessed following the manufacturer's instructions (MesoScale Discovery). Raw pSTAT3 values were determined for each sample and converted to percent of control (POC). The POC was plotted versus concentration of the test sample and $IC_{50}$ and $IC_{90}$ values were calculated using a 4 Parameter Logistic Model enabled by the Excel add-in XLfit (Activity Base software, ID Business Solutions, Ltd.). The test compounds were analyzed with respect to the $IC_{50}/IC_{90}$ as described above, and Geomeans were calculated across multiple experiments for each test sample and shown in Table 9.

Results

The results in Table 9 show that the $IC_{50}$ and $IC_{90}$ Geomean values for the tested compounds were similar to the $IC_{50}$ and $IC_{90}$ Geomean values for an anti-IL23Ap19 control antibody. The data demonstrates that the test compounds dose dependently inhibited the IL23 induced phosphorylation of STAT3 in DB cells.

TABLE 9

| Compound ID | $IC_{50}$ $IC_{90}$ | hIL23 pSTAT3 DB assay pM Geomean |
|---|---|---|
| Compound M | $IC_{50}$ | 190 |
| Compound M | $IC_{90}$ | 530 |
| Compound A | $IC_{50}$ | 210 |
| Compound A | $IC_{90}$ | 420 |
| Compound N | $IC_{50}$ | 240 |
| Compound N | $IC_{90}$ | 510 |
| Compound D | $IC_{50}$ | 280 |
| Compound D | $IC_{90}$ | 560 |
| Compound O | $IC_{50}$ | 300 |
| Compound O | $IC_{90}$ | 720 |
| Compound E | $IC_{50}$ | 300 |
| Compound E | $IC_{90}$ | 700 |
| Compound P | $IC_{50}$ | 300 |
| Compound P | $IC_{90}$ | 620 |
| Compound F | $IC_{50}$ | 260 |
| Compound F | $IC_{90}$ | 600 |
| Control antibody 3(IL23A) | $IC_{50}$ | 160 |
| Control antibody 3(IL23A) | $IC_{90}$ | 310 |

Example 9

Human IL-23 Dependent Mouse Splenocyte Assay (MSA)

A mouse splenocyte based assay was used to assess the ability of anti-human IL23 test samples to inhibit the induction of mouse IL17 by human recombinant IL23 and recombinant cynomolgus IL23 in mouse splenocyte cultures.
Materials and Methods:

Briefly, mononuclear cells from mouse spleens (female C57BL/6 less than 13 weeks of age; JAX) were isolated washed, counted and resuspended to 4×10^6 cells/ml in a standard T cell media (TCM). One hundred microliters of the mIL2/splenocyte suspension was added to 96 well microtiter plates. Recombinant human IL23 (Boehringer Ingelheim Pharmaceuticals, Inc.) or recombinant cynomolgus IL23 (Boehringer Ingelheim Pharmaceuticals, Inc.) was diluted in TCM and pre-incubated for 2 hours at 37 C with TCM alone or with titrations of test samples. After the pre-incubation of test sample+IL23, 100 ul of the mixture was added to the cells and the test plates were incubated at 37 C with 5% $CO_2$-humidified air for 48 hr. Control samples received either TCM (unstimulated controls) or recombinant human IL23 diluted in TCM (stimulated controls) After the incubation, mouse IL17 levels were determined from the supernatant using the Quantikine® Mouse IL-17 Immunoassay according to the manufacturer's instructions (R&D Systems). Interpolated mIL17 pg/ml values were determined for each sample and converted to percent of control (POC). The POC was plotted versus concentration of the test sample and $IC_{50}$ and $IC_{90}$ values were calculated using a 4 Parameter Logistic Model enabled by the Excel add-in XLfit (Activity Base software, ID Business Solutions, Ltd.). The anti-IL23 test samples were analyzed with respect to the $IC_{50}/IC_{90}$ as described above and Geomeans were calculated across multiple experiments for each test sample and shown in Table 10.
Results The results in Table 10 show that the tested compounds were able to inhibit both human and cynomolgus-IL23 induced mouse splenocyte release of IL17.

TABLE 10

| Compound ID | $IC_{50}$ $IC_{90}$ | huIL23 MSA pM Geomean | CynoIL23 MSA pM Geomean |
|---|---|---|---|
| Compound M | $IC_{50}$ | 140 | 120 |
| Compound M | $IC_{90}$ | 1600 | 890 |
| Compound A | $IC_{50}$ | 180 | 120 |
| Compound A | $IC_{90}$ | 1700 | 730 |
| Compound N | $IC_{50}$ | 230 | 140 |
| Compound N | $IC_{90}$ | 2000 | 940 |
| Compound D | $IC_{50}$ | 190 | 160 |
| Compound D | $IC_{90}$ | 2200 | 1100 |
| Compound O | $IC_{50}$ | 210 | 120 |
| Compound O | $IC_{90}$ | 2200 | 800 |
| Compound E | $IC_{50}$ | 200 | 77 |
| Compound E | $IC_{90}$ | 1700 | 1200 |
| Compound P | $IC_{50}$ | 200 | 97 |
| Compound P | $IC_{90}$ | 1400 | 1500 |
| Compound F | $IC_{50}$ | 170 | 69 |
| Compound F | $IC_{90}$ | 2300 | 1500 |
| Control antibody 3(IL23A) | $IC_{50}$ | 53 | 17 |
| Control antibody 3(IL23A) | $IC_{90}$ | 350 | 240 |

Example 10

Inhibition of IL23 induced phosphorylation of STAT3

IL23 engagement with its heterodimeric receptor complex (IL12Rβ1-IL23R) results in the downstream phosphorylation of Signal transducer and activator of transcription 3 (STAT3). Compounds were tested for the ability to inhibit IL23 induced STAT3 activation in DB stable transfected cells
Materials and Methods The cells were stimulated with a final concentration of 15 ng/ml of IL23 protein. This dose was estimated to be the EC60 according to previous experiments, while allowing for inhibition with the tested compound. Cells were plated, compound dosed, and IL-23 added (in that order) and incubated overnight. If the compound inhibited cell stimulation, STAT3 was downregulated, leading to less luciferase activity.
Results The results in Table 11 show that the tested compounds were able to inhibit IL23 induced phosphorylation of STAT3.

TABLE 11

| Compound ID | $IC_{50}$ $IC_{90}$ | IL23A pSTAT3 (MG) pM Geomean |
|---|---|---|
| Compound M | $IC_{50}$ | 120 |
| Compound M | $IC_{90}$ | 300 |
| Compound A | $IC_{50}$ | 130 |
| Compound A | $IC_{90}$ | 1100 |
| Compound O | $IC_{50}$ | 160 |
| Compound O | $IC_{90}$ | 650 |
| Compound E | $IC_{50}$ | 140 |
| Compound E | $IC_{90}$ | 830 |
| Compound P | $IC_{50}$ | 69 |
| Compound P | $IC_{90}$ | 480 |
| Compound F | $IC_{50}$ | 90 |
| Compound F | $IC_{90}$ | 650 |
| Control antibody 3(IL23A) | $IC_{50}$ | 35 |
| Control antibody 3(IL23A) | $IC_{90}$ | 140 |

Example 11

Further IL23-A Stat3 assays

Further experiments were run similarly to Example 8 to test for inhibition of IL23 induced activation of STAT3.
Methods and Materials DB-STAT3Luc10 Clone 10 suspension cells were grown in RPMI1640+10% FBS. 20,000 cells were added per well of 96 well plates at 80 ul/well of cell suspension. 10 ul of one of the serially diluted test compounds was added to each well. 15 ng/mL of recombinant human IL-23 was added to each well, with certain wells contained only test compounds and no IL-23, for comparison. The plates were incubated overnight at 37° C./5% CO2. Luciferase activity was assayed using Steady-Glo (Promega and One-Glo (Promega and the results were read on Envision Reader.
Results The $IC_{50}$ and $IC_{90}$ for the tested compounds are shown in Table 12 and Table 13. These tables show that the compounds inhibited IL-23-dependent STAT3 activation in a dose dependent manner.

TABLE 12

| Compound ID | $IC_{50}$ (pM) | $IC_{90}$ (pM) |
|---|---|---|
| Compound N | 235.2 | 873.7 |
| Control antibody 3(IL23A) | 96.5 | 192.6 |
| Compound D | 185.6 | 871.6 |

TABLE 12-continued

| Compound ID | IC$_{50}$ (pM) | IC$_{90}$ (pM) |
| --- | --- | --- |
| Compound E | 211.9 | 965.1 |
| Control antibody 3(IL23A) | 104.3 | 198.8 |
| Compound G | 220.2 | 1151.0 |
| Compound C | 162.7 | 620.4 |
| Control antibody 3(IL23A) | 80.3 | 181.3 |

TABLE 13

| | First test | | Second test | | GEOMEAN | |
| --- | --- | --- | --- | --- | --- | --- |
| Compound ID | IC$_{50}$ (pM) | IC$_{90}$ (pM) | IC$_{50}$ (pM) | IC$_{90}$ (pM) | IC50 (pM) | IC90 (pM) |
| Control antibody 3 (IL23A) | | | 96.5 | 192.6 | 93.1 | 190.8 |
| | | | 104.3 | 198.8 | | |
| | | | 80.3 | 181.3 | | |
| Compound N | 178.6 | 856.4 | 235.2 | 873.7 | 205.0 | 865.0 |
| Compound D | 178.1 | 657.2 | 185.6 | 871.6 | 181.8 | 756.8 |
| Compound E | 170.2 | 764.9 | 211.9 | 965.1 | 189.9 | 859.2 |
| Compound G | 187.1 | 600.5 | 220.2 | 1151.0 | 203.0 | 831.4 |
| Compound C | 134.9 | 352.6 | 162.7 | 620.4 | 148.1 | 467.7 |

Example 12

Inhibition of Mouse IL17A and IL22 release induced by Human recombinant IL23

Test compounds were assessed for their ability to inhibit human IL23 induced cytokine release in C57/Bl6 mice. IL17A and IL22 secretion are measured after intradermal injection of IL23
Materials And Methods Briefly, C57BL/6 female mice (7-10 weeks old, Charles River) were randomly divided into 8 groups, 8 animals/group and given a 100 µl intraperiotoneal injection of either citrate buffer (20 mM NaCitrate, 115 mM NaCl, pH 6.0) or test compounds at equivalent molar dose of 1.3, 0.4 and 0.13 mg/kg vs. 1, 3 and 0.1 mg/kg respectively.

Figure 4:
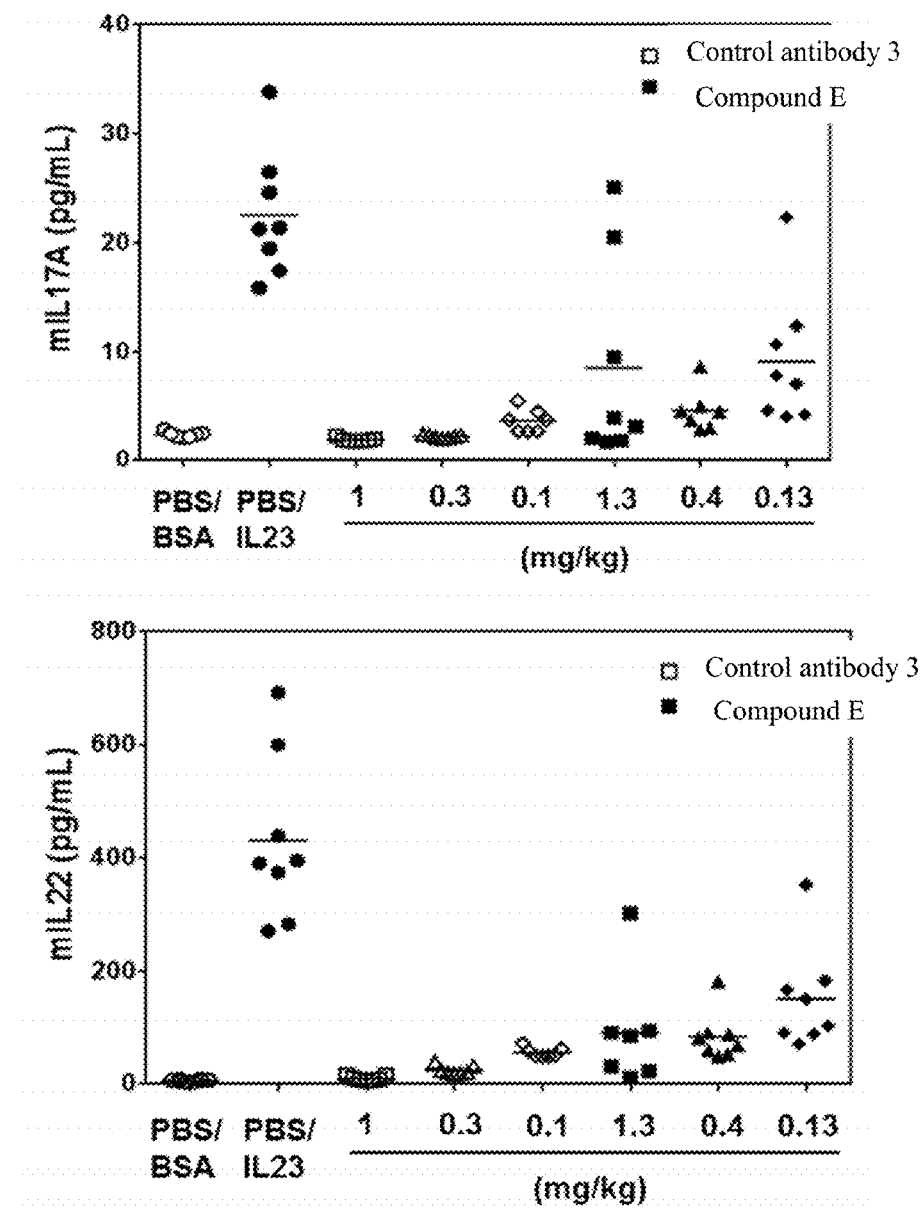
FIG. 4 is a series of graphs and a table showing that compound E maintained functional potency vs. IL23 in vivo. Mice were dosed equimolar with either control antibody 3 (IL23A monoclonal antibody) or compound E and challenged with human IL23 twice to induce ear inflammation. Twenty four hours after the final injection, ears were collected and analyzed for mouse IL17A and mouse IL22 as a measure of functional blockade of IL23. Compound E maintained functional potency in vivo vs. control antibody 3 (IL23A monoclonal antibody) based on terminal exposure and level of efficacy. Control antibody 3: open squares, triangles and diamonds. Compound E: full squares, triangles and diamonds. MW: molecular weight.

One hour after test compound dosing mice were anesthetized via isoflurane (Butler Schein) and given a 20 µl intradermal injection of either 0.1% BSA (Sigma) control or 15 µg/ml (0.3 µg) rhIL23 (generated in-house) diluted in saline (Invitrogen) to both ears. Intradermal challenges were repeated daily for 2 consecutive days. Twenty-four hours after the second challenge the mice were sacrificed via cervical dislocation and each ear was removed. Ear tissue was homogenized in 1 ml of homogenization buffer (HBSS (Gibco); 0.4% Triton X-100 (Sigma); 1× SigmaFast Protease Inhibitor (Sigma)) using a MP Biomedicals Fast-Prep 24 homogenizer. Homogenized samples are centrifuged at 4 C for 10 min and supernatant collected. Supernatants were assayed for the presence of mouse IL17A and IL22, using the Quantikine® Mouse IL-17 and mouse IL-22 Immunoassays according to the manufacturer's instructions (R&D Systems). Interpolated cytokine pg/ml values were determined for each sample. The mean pg/ml levels for each treatment group were determined and significance compared to control calculated using the One-way ANOVA followed by Dunnett's multiple comparisons test. Results are shown in FIG. 4.
Results The results in FIG. 4 show that treatment with a single intraperitoneal dose of test compound was able to significantly inhibit the release of mouse IL17 and IL22 in the skin induced by two daily consecutive intra dermal injections of recombinant human IL23.

Example 13

Inhibition of Exogenous Human TNF-alpha Dependent Cytokine Release in C57/Bl6 Mice Test compounds were assessed for their ability to inhibit human TNF induced cytokine release in C57/Bl6 mice after exogenous exposure to human TNF. Serum KC and IL-6 secretion are measured following intraperitoneal administration of human TNF.
Materials and Methods Briefly, C57BL/6 female mice (8-9 weeks old, Jackson Labs) were randomly divided into 8 groups, 8 animals/group and given a 200 µl intraperiotoneal injection of either phosphate buffered saline (Sigma) or test compound at equivalent molar dose of 13.3, 4 and 1.3 mg/kg vs. 10, 3 and 1 mg/kg respectively.

Figure 5:
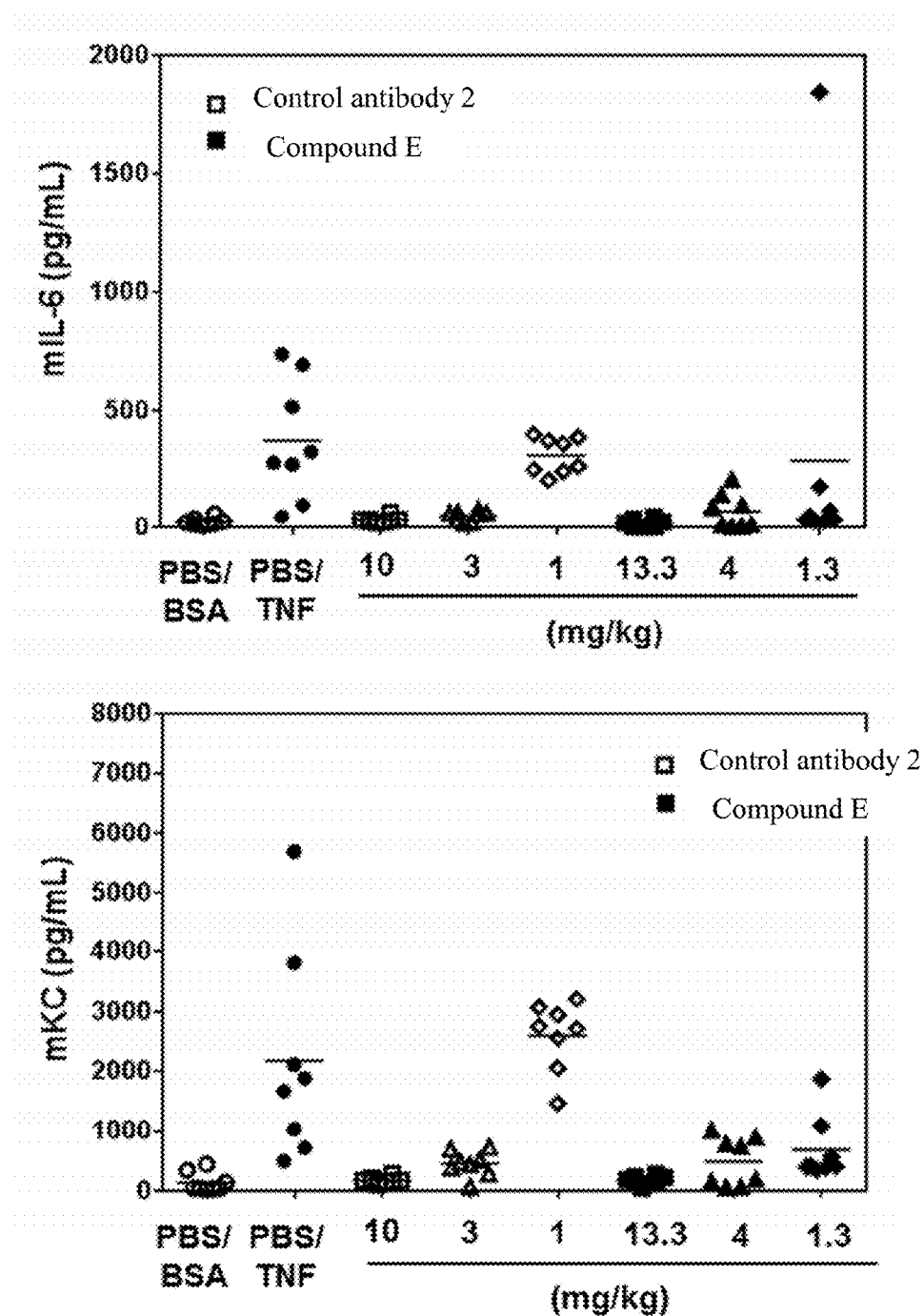
FIG. 5 is a series of graphs and a table showing that Compound E maintained functional potency vs. TNF in vivo. Mice were dosed equimolar with either control antibody 2 (TNFa monoclonal antibody) or compound E and challenged with human TNF. Two hours after the challenge, whole blood was collected and serum analyzed for mouse KC and mouse IL-6 as a measure of functional blockade of TNF. Compound E maintained functional potency in vivo vs. anti-TNF based on terminal exposure and level of efficacy. Control antibody 3: open squares, triangles and diamonds. Compound E: full squares, triangles and diamonds. MW: molecular weight.

Two hour after test compound dosing mice were anesthetized via isoflurane (Butler Schein) and given a 200 µl intraperitoneal injection of either 0.1% BSA control or 15 µg/ml (3 µg) rhTNF (R&D Systems) diluted in saline (Sigma). Two hours after the TNF challenge the mice were anesthetized via isoflurane, whole blood was collected and mice were then sacrificed via cervical dislocation. Whole blood was centrifuged at 12,000 rpm for 10 minutes and plasma collected. Plasma was assayed for the presence of mouse KC and IL-6, using the MultiPlex® Mouse KC and mouse IL-6 Immunoassays according to the manufacturer's instructions (MSD). Interpolated cytokine pg/ml values were determined for each sample. The mean pg/ml levels for each treatment group were determined and significance compared to control calculated using the One-way ANOVA followed by Dunnett's multiple comparisons test. Results are shown in Figure X.
Results The results in FIG. 5 show that treatment with a single intraperitoneal dose of test compound was able to significantly inhibit the release of mouse KC and IL-6 in serum by intraperitoneal injection of recombinant human TNF.

Example 14

Pharmacokinetics of compounds in cynomolgus monkeys

Materials and Methods

Single intravenous (IV) dose PK studies for two pairs of compounds (Compound M and Compound A; and Compound O and Compound E) were conducted in male cynomolgus monkeys (N=3 per group) naïve to biologics, and conducted according to the guidelines of Institutional Animal Care and Use Committee. IV doses were administered at 1 mg/kg as 10 min IV infusion. Serum samples were collected at pre-dose, 1, 4, 8 hr on the day of dosing, and 1, 2, 3, 4, 5, 7, 10, 14, 21, 28, 35, and 42 (1008 hr) days post dosing for Compound M and Compound A; and only up to Day 14 for Compound O and Compound E. Serum concentrations of the dosed molecules were measured by a ligand binding assay (ELISA).

Calibration standard curve and quality control (QC) samples were prepared in 100% serum for each analyte. Each standard curve consisted of seven non-zero points starting at 10240 ng/mL then serially diluted 3×. A blank sample (matrix without analyte) was also included. Four QC samples at low, medium, and high ranges were prepared starting at 2560 ng/mL then serially diluted four-fold. The standard curve and QC samples were stored frozen until sample analysis at which time they were diluted 20 times to mimic study samples. The standard curve and QC samples were included in duplicate during each analytical run. The lower and upper limits of quantification were defined as the lowest and highest standard curve points to reproducible have a back-calculated concentration that does not exceed 25 percent (%) of the nominal concentration. The acceptance criterion for the standard curve points and QC samples was 25 percent (%) of the nominal concentration.

Nunc ELISA plates were coated with 1 µL of monkey adsorbed goat anti-human IgG (Southern Biotech) as the capture reagent and incubated overnight at 2-8° C. After washing and blocking the plates with the wash buffer (0.05% (v/v) Tween 20 in phosphate buffered saline (PBS)) and blocking buffer (5% bovine serum albumin (BSA) in PBS), standard, QC, and unknown samples, diluted 1:20, 1:400 and 1:8000 with 5% monkey serum (monkey serum from Innovative Research) were added to the plate wells and incubated for 1 hour at room temperature. The plate wells were washed with the washing buffer and added with monkey adsorbed biotinylated goat anti-human IgG (Southern Biotech) as the secondary reagent and incubated at room temperature for 1 hour. The plates were washed 3 times and added with 100 µL of 1 µg/mL peroxidase-conjugated streptavidin for 15 min at room temperature, followed by further 3 times washing and the addition of 100 µL of 3,3',5,5'-Tetramethylbenzidine (TMB, BioFX) substrate for 3-4 min at room temperature. The reaction was stopped by adding 100 µL of stop solution (BioFX) and the absorbance was measured using Molecular Devices plate reader with SoftmaxPro software, version 5.4.1.

Results

Single IV dose PK studies for two pairs of test compounds (Compound M and Compound A; and Compound O and Compound E) were conducted in male cynomolgus monkeys (N=3 per group) naïve to biologics. The test compounds were dosed at 1 mg/kg as 10 min IV infusion. Serum samples were collected at pre-dose, 1, 4, 8 hr on the day of dosing, and 1, 2, 3, 4, 5, 7, 10, 14, 21, 28, 35, and 42 (1008 hr) days post dosing for Compound M and Compound A; and only up to Day 14 for Compound O and Compound E. Serum concentrations of the dosed molecules were measured by a ligand binding assay (ELISA).

Serum concentrations (mean and SD) for each of the molecules are summarized in Table 14.

TABLE 14

Serum concentrations (mean ± SD, N = 3) for the test compounds in cynomolgus monkey

| Time (day) | Compound M | | Compound A | | Compound O | | Compound E | |
|---|---|---|---|---|---|---|---|---|
| | Mean (nM) | SD (nM) | Mean (nM) | SD (nM) | Mean (nM) | SD (nM) | Mean (nM) | SD (nM) |
| 0 | 0 | 0 | 0 | 0 | 0 | 0 | 0 | 0 |
| 0.042 | 89.62 | 26.41 | 115.60 | 15.44 | 96.69 | 23.15 | 107.57 | 10.43 |
| 0.167 | 75.30 | 17.97 | 108.03 | 22.92 | 92.29 | 19.75 | 102.36 | 4.81 |
| 0.333 | 69.71 | 9.19 | 89.15 | 16.32 | 65.27 | 11.53 | 86.45 | 10.65 |
| 1 | 54.49 | 13.94 | 63.68 | 6.69 | 30.10 | 12.41 | 52.87 | 8.85 |
| 2 | 35.17 | 8.93 | 49.95 | 6.04 | 7.44 | 3.22 | 32.51 | 6.30 |
| 3 | 18.58 | 6.66 | 43.51 | 6.64 | 4.14 | 0.70 | 24.65 | 6.49 |
| 4 | 13.86 | 5.61 | 40.02 | 8.50 | 2.76 | 0.25 | 19.02 | 4.84 |

TABLE 14-continued

Serum concentrations (mean ± SD, N = 3) for the test compounds in cynomolgus monkey

| Time (day) | Compound M | | Compound A | | Compound O | | Compound E | |
|---|---|---|---|---|---|---|---|---|
| | Mean (nM) | SD (nM) | Mean (nM) | SD (nM) | Mean (nM) | SD (nM) | Mean (nM) | SD (nM) |
| 5 | 9.55 | 3.40 | 43.69 | 19.63 | 1.96 | 0.09 | 13.98 | 3.84 |
| 7 | 3.76 | 1.31 | 27.84 | 3.29 | 1.08 | 0.21 | 8.49 | 3.38 |
| 10 | BQL | BQL | BQL | BQL | BQL | BQL | 0.3797 | NA |
| 14 | BQL | BQL | BQL | BQL | BQL | BQL | BQL | BQL |
| 21 | BQL | BQL | BQL | BQL | | | | |
| 28 | BQL | BQL | BQL | BQL | | | | |
| 35 | BQL | BQL | BQL | BQL | | | | |
| 42 | BQL | BQL | BQL | BQL | | | | |

BQL: below quantitation limit
NC: not calculated, N = 1

Figure 2:
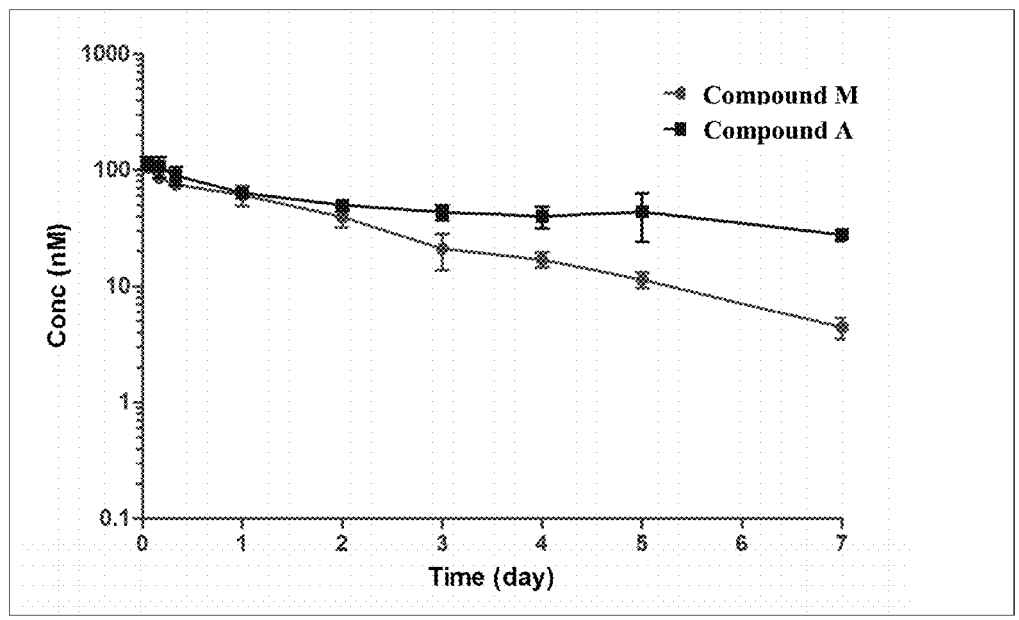
FIG. 2 is a graph showing the serum concentrations of Compound M and its YTE mutant Compound A in male cynomolgus monkey (mean±SD; N=3) after 1 mg/kg IV 10 minute infusion.
Figure 3:
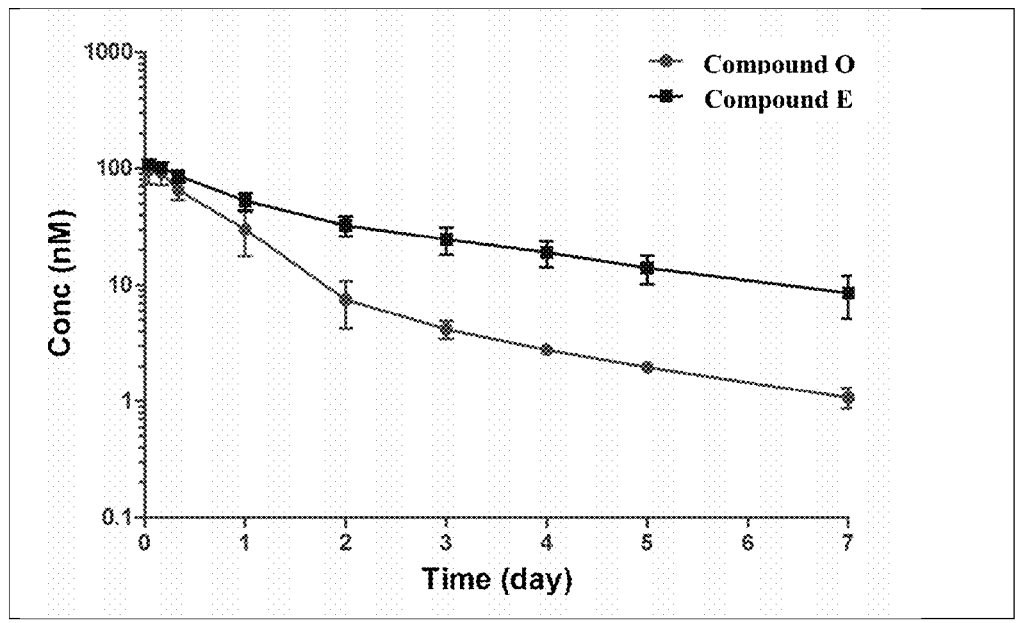
FIG. 3 is a graph show serum concentrations of Compound O and its corresponding YTE mutant Compound E in male cynomolgus monkey (mean±SD; N=3) after 1 mg/kg IV 10 minute infusion.

Pharmacokinetic (PK) parameters of these test compounds were calculated using the software Phoenix Win-Nonlin 6.1 (Certara, MD, USA) using non-compartmental approach for IV infusion dose. Serum samples that showed precipitous drop in the concentrations at any time point after dosing and all subsequent samples in that particular animal were excluded from the PK parameter estimation. Additional analysis showed that this sudden drop in the concentrations after the first few days was due to the development of anti-compound antibodies for a humanized biologic molecule in monkey. Only the first seven day data from individual animals were included in the PK analysis. Concentration-time plots are shown in FIGS. 2 and 3 for the two pairs of test compounds. Key PK parameters (mean±SD) for the two pairs of test compounds are summarized in Table 15.

TABLE 15

Key PK parameters (mean ± SD; N = 3) of the two test compound pairs in cynomolgus monkey after 1 mg/kg IV 10 min infusion dose

| Compound ID | AUC (nM · day) | CL (mL/day/kg) | Vss (mL/kg) | T½ (day) | MRT (day) |
|---|---|---|---|---|---|
| Compound M | 186 ± 48.3 | 28.2 ± 7.8 | 62.4 ± 13.7 | 1.6 ± 0.04 | 2.2 ± 0.1 |
| Compound A | 592 ± 68.3 | 8.5 ± 1.1 | 71.5 ± 8.9 | 6.2 ± 0.5 | 8.4 ± 1.0 |
| Compound O | 98.0 ± 14.7 | 51.8 ± 7.8 | 76.1 ± 30.3 | 2.3 ± 0.8 | 1.4 ± 0.4 |
| Compound E | 244 ± 54.6 | 21.2 ± 4.5 | 65.0 ± 3.9 | 2.5 ± 0.3 | 3.1 ± 0.5 |

Compound A, the test compound with YTE mutation showed a 3.3-fold reduction in clearance (CL) and a 3.9-fold increase in terminal half-life (T½) compared to the corresponding test compound not containing YTE mutation (Compound M). Compound E, the test compound with YTE mutation showed a 2.4-fold reduction in CL compared to the corresponding test compound not containing YTE mutation (Compound O).

Example 15

Predicting human PK and human dose of exemplary compound

Predicting Human PK:

Human PK prediction of Compound E was done by allometric scaling from the PK parameters obtained in cynomolgus monkey using a factor of 2-fold reduction in clearance in humans compared to monkey while maintaining same volume of distribution. Thus, predicted clearance in humans is 12.1 mL/day/kg with a terminal half-life of 7.4 days.

Predicting Human Dose:

Human dose prediction was done based on extensive exposure-efficacy data available from clinical trials of golimumab in diverse patient populations. Golimumab (Simponi®) is approved to treat rheumatoid arthritis (RA), ankylosing spondylitis (AS), and psoriatic arthritis (PsA) patients with 50 mg monthly subcutaneous (SC) doses, and ulcerative colitis (UC) patients with 100 mg monthly SC doses. Simponi® achieves a Ctrough of approximately 3.2 nM in RA patients (50 mg monthly SC doses) and 9.7 nM (100 mg monthly SC doses) in UC patients (Simponi® BLA, 2009; Sandborn, 2013). These are used as benchmarks for therapeutic Ctroughs for AS and CD, respectively. Ctrough levels at the clinically approved doses of Stelara are about 6 nM. Based on the observation of a 3-fold higher potency of Compound Ecompared to ustekinumab (Stelara®) Ctrough values of ~2 nM are needed for Compound Eto cover IL23. As the Ctrough concentration for covering TNF is greater than that for covering IL23, the 9.7 nM Ctrough for Simponi® was used for dose projections.

Compartmental modeling of PK data in the cynomolgus monkey (2-compartment model) followed by Monte-Carlo simulations using a 2-fold reduction scaling of CL, 73% bioavailability, and simultaneously varying clearance and distributional rate constants with a nominal 30% CV and log-normal distribution shows that 54 mg (90% confidence intervals 31-90 mg) SC doses administered every 2 weeks will maintain a Ctrough of 9.7 nM.

Example 16

Purification of Compounds

Methods

Compounds were purified using Mab Select SuRe as an affinity purification step. High salt washes are avoided in order to prevent aggregation. Elution was performed using Sodium Acetate buffer pH 3.5. Following Mab Select SuRE purification the sample was neutralized and applied to a Hydroxyapatite Type I resin and eluted using various concentrations of phosphate buffer. Monomer peak elutes ~140 mM NaPhosphate 100 mM NaCl pH 7.0 and aggregate peak eluted at ~200 mM NaPhosphate 100 mM NaCl pH 7.0. Following hydroxyapatite, the sample was consistently >95% monomer.

Sedimentation velocity (SV) experiment via Analytical ultracentrifugation (AUC) was used to provide information on sample purity and aggregation states. Samples were centrifuged in an optima XL-I (Beckman Coulter, Fullerton, Calif.) at 20° C. using an An60Ti four-hole rotor running at 40,000 rpm. The sedimentation process was monitored by ultraviolet absorbance at 280 nm, using corresponding dilution buffer as reference buffer. The variation in the concentration distribution in the ultracentrifuge cell with time was collected using XL-I operating software and was analyzed using the continuous c(S) distribution model in the SEDFIT software (version 14.1) to give the distribution of sedimentation coefficient. Monomer percentage was calculated based on the integrated peak area.

Results

The results of purification of the compounds are shown in Table 16. The data show that the compounds have high purity and homogeneity indicating good stability.

TABLE 16

| Parameter | Compound A | Compound E |
| --- | --- | --- |
| Percent monomer (sedimentation velocity) | 99.4 | 99.0 |

Example 17

Mass Spectrometry Profile of compounds

Methods

Native Sample

This procedure yielded the intact mass of the compound or protein. 2 ul of sample was injected onto an Agilent PoroShell 300SB-C8 column, 5 um, (75×1.0 mm). The column temperature was 80° C. and flow rate was 50 ul/min. The compound or protein was eluted off the column with a gradient from 20% B at 0 minutes to 85% B at 10 minutes. Mobile phase A was Water/Acetonitrile/Formic Acid (99/1/0.1) and Mobile phase B was Acetonitrile/Water/Formic Acid (95/5/0.1). The effluent was directed to an Agilent 6210 TOF mass spectrometer, which was scanned from mass 600 to mass 3200. The raw data was deconvoluted with the program MassHunter.

Reduced Sample

This procedure yielded the mass of the protein or the light chain and the mass of the heavy chain. 2 ul of 50 mM TCEP was added to 10 ul of sample and 10 ul of 8M Guanidine and incubated for 15 minutes at 37° C. 2 ul of this sample was injected as above, with the following differences: the column temperature was 60° C. and the mass range was 600-2000.

Deglycosylated Sample

This procedure yielded the deglycosylated mass of the protein or the light chain and the heavy chain. 10 ul of sample, 10 ul of 200 mM $NH_4HCO_3$, 2 ul 50 mM TCEP, and 1 ul (1:10) PNGase F (or 1 uL QA deglycosylation mix if O-linked glycosylations were present) were incubated for 3 hours at 37° C. The incubation was increased to overnight for heavily glycosylated samples. Then, 25 ul 8M Guanidine and 4 ul of 50 mM TCEP were added and incubated for 15 minutes at 37° C. This sample was injected as above for reduced sample.

Protein Peptide Mapping by Mass Spectrometry 25 ul of sample was added to 25 ul of 8M urea in 400 mM ammonium bicarbonate. 5 ul of 50 mM TCEP was then added and the sample was incubated for 15 minutes at 60° C. After cooling the sample to room temperature, 5 ul of 150 mM iodoacetamide was added and the sample was incubated at room temperature for 15 minutes. After adding 40 ul of water, 5 ul of trypsin in 1 mM HCl was added to give a final enzyme: substrate ratio of 1:50. The sample was incubated at 37° C. overnight. 5 ul was then injected onto a Thermo Hypurity C18 column, 100×1.0 mm. Flow rate was 80 ul/min. The protein was eluted off the column with a gradient from 0% B at 0 minutes to 40% B at 33 minutes. Mobile phase A was Water/Acetonitrile/Formic Acid (99/1/0.1) and Mobile phase B was Acetonitrile/Water/Formic Acid (95/5/0.1). The effluent was directed to a Thermo Orbitrap Velos mass spectrometer. The first scan event was in the FT, and scans from mass 300 to mass 2000 with a resolution of 30,000. The second through the seventh scan events were in the IT (ion trap) and fragmented the 6 most intense ions from the first scan event. Peptides containing glycosylation were profiled by manual extraction and percentages calculated based on peak heights.

Results

The results are shown in Table 17. The data indicate the intended amino acid sequence and structure has been expressed and recovered without unexpected heterogeneity. The glycosylation pattern is typical of a conventional antibody expressed in CHO cells and does not show any atypical structures.

TABLE 17

| Parameter | Compound A | Compound E |
| --- | --- | --- |
| Mass Spectrometry: Intact Molecular Weight Profile | Intact/Matches Sequence | Intact/Matches Sequence |
| Mass Spectrometry: Glycosylation Profile | Not Determined | Similar to CHO expressed IgG |

Example 18

Thermal Stability of compounds

Methods

Thermal unfolding and aggregation of 2 mg/ml solutions of the compounds in phosphate buffer were monitored from 20° C. to 110° C. at a scan rate of 60° C./hr via an automated capillary DSC (MicroCal, LLC, Boston). Two scans with the corresponding buffer were performed to establish instrument thermal history and to obtain the instrument baseline for each sample, with the average of these scans subtracted from the subsequent protein thermogram to obtain the apparent heat capacity. Normalized scans were then analyzed with Origin 7.0. Pre-transition baselines were subtracted from each resulting heat capacity thermogram, to give the resulting excess heat capacity (Cp,ex) as a function of temperature. Reported values of transition temperatures (Tm) represent positions of peak maxima determined by visual inspection of the experimental thermograms.

Results

The results are shown in Table 18. The data show that the compounds are stable and would predict the ability to have a long shelf-life.

TABLE 18

| Parameter | Compound A | Compound E |
| --- | --- | --- |
| Thermal Stability (° C.) | 57.9, 72.1, 82.9 | 67.6, 83.1 |

Example 19

Solubility of compounds

Methods

The compound samples were concentrated gradually to a concentration as high as possible without precipitation observed using Amicon Ultra centrifugal filter with cut-off molecular weight of 50,000 Dalton (Millipore, Billerica). The concentrated protein solutions were then analyzed in SV experiment via AUC to provide information on sample purity and aggregation states (refer to Example 16 regarding purification for method details).

Results

The results are shown in Table 19. The data show that the compounds are soluble and stable retaining a high percentage of monomer without formulation or added excipients.

TABLE 19

| Parameter | Compound A | Compound E |
| --- | --- | --- |
| Solubility (Concentration) | 48 mg/ml | 51 mg/ml |
| Percent Monomer | 98.6 | 97.0 |

Example 20

Valence of compounds

Methods

The valence measurement for the compound samples in 50 mM KCl and 10 mM sodium acetate buffer at pH 5.0 was performed on a Beckman Coulter (Fullerton, Calif.) ProteomeLab PA800™ apparatus equipped with an ultraviolet (UV) absorbance detector, with a working wavelength of 214 nm. The system was maintained at 20° C. and an eCap amine capillary with an inner diameter of 50 µm (Beckman Coulter, part #477431) was used. The capillary was rinsed with 100 mM NaOH, amine regeneration solution (Beckman Coulter, part #477433) and running buffer before each sample injection. Migration times for the samples were measured at voltages of 10 kV, 14 kV, and 18 kV. Dimethylformamide (DMF) (0.005%) (Pierce) was used as an electroosmotic flow (EOF) marker. Data were acquired using 32 Karat™ software (v7.0). Diffusion coefficient was determined from SV experiment via AUC.

Results

The valence data (see Table 20) indicate colloidal stability of the compounds in solution, i.e. net interaction of protein and protein in solution. The compounds with valence greater than 15 have strong net repulsive interaction and high potential to be formulated at high concentration.

TABLE 20

| Parameter | Compound A | Compound E |
| --- | --- | --- |
| Valence, pH 5.0 | 20.9 | 24.4 |

Example 21

Predicted in Silico Immunogenicity

Methods

Immunogenicity of protein therapeutics was predicted in silico by utilizing a computational tool, EpiMatrix that was developed by EpiVax, Inc. (Providence, R.I.). EpiMatrix incorporates the prediction of T-helper epitope as well as the T-regitope, of which the former is to provoke an immune response while the latter is inhibitory. Briefly, the protein sequence was first parsed into overlapping 9-mer peptide frames that has been proven the core of class II HLA binding. The binding potential of 9-mer peptides to each of eight common class II HLA alleles are evaluated based on experimental data or computational prediction. A score is generated to reflect the binding potential of the 9-mer peptide to each HLA allele and normalization is performed to make it possible to compare any 9-mer across multiple HLA alleles and enable immunogenicity prediction on a global scale. In the end the program generates an overall 'immunogenicity score', tReg Adjusted Epx Score, that together with other immunogenicity determinants helps to make an informed decision of the likelihood that the compounds will provoke an immune response in vivo.

Results

The results are shown in Table 21. The overall immunogenicity scores for these compounds are low and predict that these compounds are not likely to illicit a strong immune response in vivo.

TABLE 21

| Parameter | Compound A | Compound E |
|---|---|---|
| EpiVax | −37.7, −35.6 | −31.1, −46.8 |

Normalization of allele-specific scores

Example 22

Whole Blood Stability of Compounds

Methods

A whole blood interference assay was developed on an Octet RED96 to detect the effects of non-specific binding or off-target binding for compounds in the presence of whole blood (WB). The compound solutions in whole blood and 1× kinetic running buffer (1×kb) were incubated at a temperature of 37° C. for 48 hours. Kinetic measurements for the incubated compound samples were performed with an Octet RED96 equipped with streptavidin (SA) biosensor tips (ForteBio, Menlo Park, Calif.) at 27° C. The ratio of the on-rates/binding signals in buffer and whole blood were reported. A ratio <2 was considered to show no interference.

Results

The results are shown in Table 22.

TABLE 22

| Parameter | Compound A | Compound E |
|---|---|---|
| Ration of binding signal in whole blood/kinetic buffer to hu TNFa | 1.5 | 1.4 |
| Ratio of binding signal in whole blood/kinetic buffer | 1.8 | 1.3 |

Example 23

Summary of tested parameters

A summary of the parameter data for certain compounds is shown in Table 23 below.

TABLE 23

| Parameter | Compound A | Compound E |
|---|---|---|
| Percent Monomer after two-step purification process | 99.4% | 99% |
| Mass Spectrometry Profile | Intact | Intact |
| pI as determined by IEF (heterogeneity) | ~8.8 | ~8.8 |
| Thermal Stability (differential scanning calorimetry) | 57.9, 72.1, 82.9 | 67.6, 83.1 |
| Solubility | 48 mg/ml | 51 mg/ml |
| Valence at pH 5.0 | 20.9 | 24.4 |
| Predicted Immunogenicity (EpiVax Score) | −37.69, −35.57 | −31.1, −46.8 |
| Whole Blood Stability (human WB, 48 hrs at 37 C.); maintenance of binding to IL23 and TNFa | Maintained | Maintained |

Sequences

| SEQ ID NO | Sequence |
|---|---|
| 1 | EVQLVESGGGLVQPGRSLRLSCAASGFTFDDYAMHWVRQAPGK GLEWVSAITWNSGHIDYADSVEGRFTISRDNAKNSLYLQMNSL RAEDTAVYYCAKVSYLSTASSLDYWGQGTLVTVSS |
| 2 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIK |
| 3 | QVQLVESGGGVVQPGRSLRLSCAASGFIFSSYAMHWVRQAPGN GLEWVAFMSYDGSNKKYADSVKGRFTISRDNSKNTLYLQMNSL RAEDTAVYYCARDRGIAAGGNYYYYGMDVWGQGTTVTVSS |
| 4 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIK |
| 5 | QVQLVESGGGVVQPGRSLRLSCAASGFIFSSYAMHWVRQAPGD GLEWVAFMSYDGSNKKYADSVKGRFTISRDNSKNTLYLQMNSL RAEDTAVYYCARDRGIAAGGNYYYYGMDVWGQGTTVTVSS |
| 6 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIK |
| 7 | QVQLVQSGAEVKKPGSSVKVSCKASGYTFTDQTIHWMRQAPGQ GLEWIGYIYPRDDSPKYNENFKGKVTITADKSTSTAYMELSSL RSEDTAVYYCAIPDRSGYAWFIYWGQGTLVTVSS |
| 8 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIK |
| 9 | GGGSGGG |
| 10 | LGGGSG |
| 11 | FNRGES |
| 12 | VEPKSS |
| 13 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGASTKGPSVFPLAPSSKS TSGGTAALGCLVKDYFPEPVTVSWNSGALTSGVHTFPAVLQSS GLYSLSSVVTVPSSSLGTQTYICNVNHKPSNTKVDKRVEPKSC DKTHTCPPCPAPEAAGGPSVFLFPPKPKDTLYITREPEVTCVV VDVSHEDPEVKFNWYVDGVEVHNAKTKPREEQYNSTYRVVSVL TVLHQDWLNGKEYKCKVSNKALPAPIEKTISKAKGQPREPQVY TLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPGK |
| 14 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 15 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSFNRGESASTKGPSVFPLAPSSKS TSGGTAALGCLVKDYFPEPVTVSWNSGALTSGVHTFPAVLQSS GLYSLSSVVTVPSSSLGTQTYICNVNHKPSNTKVDKRVEPKSC DKTHTCPPCPAPEAAGGPSVFLFPPKPKDTLYITREPEVTCVV |

| SEQ ID NO | Sequence |
|---|---|
|  | VDVSHEDPEVKFNWYVDGVEVHNAKTKPREEQYNSTYRVVSVL TVLHQDWLNGKEYKCKVSNKALPAPIEKTISKAKGQPREPQVY TLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPGK |
| 16 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 17 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLYITREPEVTCV VVDVSHEDPEVKFNWYVDGVEVHNAKTKPREEQYNSTYRVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 18 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVLVQSGAEVKK GSSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 19 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLYITREPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 20 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVLVQSGAEVKK GSSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSVEPKSSRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 21 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYGMDVWGQGTTVTVSSLGGGSGASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLYITREP |
| 22 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 23 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYGMDVWGQGTTVTVSSFNRGESASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLYITREP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 24 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 25 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLYITREPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 26 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 27 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLYITREPEVTCV |

| SEQ ID NO | Sequence |
|---|---|
|  | VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 28 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 29 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLYITREPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 30 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 31 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLYITREP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 32 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 33 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLYITREPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| 34 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 35 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLYITREP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 36 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 37 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTKPR EEQFNSTYRVVSVLTVLHQDWLNGKEYKCKVSNKGLPSSIEKT ISKAKGQPREPQVYTLPPSQEEMTKNQVSLTCLVKGFYPSDIA VEWESNGQPENNYKTTPPVLDSDGSFFLYSRLTVDKSRWQEGN VFSCSVMHEALHNHYTQKSLSLSLG |
| 38 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLYITREPEVTCVVVDVSQEDPEVQFNWYVDGVEVHNAKTKPR EEQFNSTYRVVSVLTVLHQDWLNGKEYKCKVSNKGLPSSIEKT ISKAKGQPREPQVYTLPPSQEEMTKNQVSLTCLVKGFYPSDIA VEWESNGQPENNYKTTPPVLDSDGSFFLYSRLTVDKSRWQEGN VFSCSVMHEALHNHYTQKSLSLSLG |
| 39 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKVEPKSCDKTHTCPPCPAPELLGGPSVFLFPPK PKDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRWQ QGNVFSCSVMHEALHNHYTQKSLSLSPG |
| 40 | EPKSCDKTHTCPPCP |
| 41 | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |

| SEQ ID NO | Sequence |
|---|---|
| 42 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPEAAGGPSVFLFPPK PKDTLYITREPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRWQ QGNVFSCSVMHEALHNHYTQKSLSLSPGK |
| 43 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPEAAGGPSVFLFPPK PKDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRWQ QGNVFSCSVMHEALHNHYTQKSLSLSPG |
| 44 | DIQMTQSPSSLSASVGDRVTITCRASQGIRNYLAWYQQKPGKA PKLLIYAASTLQGVPSRFSGSGSGTDFTLTISSLQPEDVATY YCQRYNRAPYTFGQGTKVEIKGGGSGGGGVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSASTKGPSVFPLAPSSKS TSGGTAALGCLVKDYFPEPVTVSWNSGALTSGVHTFPAVLQSS GLYSLSSVVTVPSSSLGTQTYICNVNHKPSNTKVDKRVEPKSC DKTHTCPPCPAPEAAGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVY TLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPG |
| 45 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTIDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 46 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 47 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSVEPKSSRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 48 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSASTKGPSVFPL |
| | APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 49 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 50 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 51 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 52 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSLTV LHQDWLNGKEYKCKVSNKGLPSSIEKTISKAKGQPREPQVYTL PPSQLEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 53 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 54 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSASTKGPSVFPLAPCSR |

| SEQ ID NO | Sequence |
|---|---|
|  | STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLYITREPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQLEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 55 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 56 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQLEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 57 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 58 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLYITREPEVTCVVVD VSQEDPEVQFNWYVDGVEVHNAKTKPREEQFNSTYRVVSVLTV LHQDWLNGKEYKCKVPSNKGLPSSIEKTISKAKGQPREPQVYTL PPSQLEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 59 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 60 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 61 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 62 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 63 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 64 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 65 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 66 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPCSR |

| SEQ ID NO | Sequence |
|---|---|
| | STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLYITREPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 67 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 68 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQ REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 69 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 70 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQLEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 71 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 72 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL |
| | APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLYITREPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQLEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 73 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 74 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQ REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 75 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 76 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 77 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 78 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL |

| SEQ ID NO | Sequence |
|---|---|
| | APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLPPKPKDTLYITREPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 79 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 80 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 81 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 82 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 83 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 84 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 85 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 86 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLPPKPKDTLYITREPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 87 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 88 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 89 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 90 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPSSK |

| SEQ ID NO | Sequence |
|---|---|
| | STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTTPPVLDSDGSFFLYSKLTVDKSRWQQGNVFSCSVMHEALHN HYTQKSLSLSPG |
| 91 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 92 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 93 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 94 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSFNRGESASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLYITREPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 95 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSVEPKSSRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 96 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL |

| SEQ ID NO | Sequence |
|---|---|
| | APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 97 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 98 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 99 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 100 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQLEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 101 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 102 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSLGGGSGASTKGPSVFPL |

| SEQ ID NO | Sequence |
|---|---|
| | APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLYITREPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQLEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 103 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 104 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPEAAGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 105 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 106 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKR VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPG |
| 107 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 108 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL |

| SEQ ID NO | Sequence |
|---|---|
| | APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQLEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 109 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 110 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGDGLEWVAFMSYDGSN KKYADSVKGRFTISRDNSKNTLYLQMNSLRAEDTAVYYCARDR GIAAGGNYYYYGMDVWGQGTTVTVSSFNRGESASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLYITREPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| 111 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 112 | EIVLTQSPATLSLSPGERATLSCRASQSVYSYLAWYQQKPGQA PRLLIYDASNRATGIPARFSGSGSGTDFTLTISSLEPEDFAVY YCQQRSNWPPFTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 113 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 114 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGASTKGPSVFPLAPSSKS |

| SEQ ID NO | Sequence |
|---|---|
| | TSGGTAALGCLVKDYFPEPVTVSWNSGALTSGVHTFPAVLQSS GLYSLSSVVTVPSSSLGTQTYICNVNHKPSNTKVDKRVEPKSC DKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVY TLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPG |
| 115 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 116 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGASTKGPSVFPLAPCSRS TSESTAALGCLVKDYFPEPVTVSWNSGALTSGVHTFPAVLQSS GLYSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVLTVL HQDWLNGKEYKCKVSNKGLPSSIEKTISKAKGQPREPQVYTLP PSQLEMTKNQVSLTCLVKGFYPSDIAVEWESNGQPENNYKTTP PVLDSDGSFFLYSRLTVDKSRWQEGNVFSCSVMHEALHNHYTQ KSLSLSLG |
| 117 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 118 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGASTKGPSVFPLAPCSRS TSESTAALGCLVKDYFPEPVTVSWNSGALTSGVHTFPAVLQSS GLYSLSSVVTVPSSSLGTKTYTCNVDHKPSNTKVDKRVESKYG PPCPPCPAPEFLGGPSVFLFPPKPKDTLYITREPEVTCVVVDV SQEDPEVQFNWYVDGVEVHNAKTKPREEQFNSTYRVVSVLTVL HQDWLNGKEYKCKVSNKGLPSSIEKTISKAKGQPREPQVYTLP PSQLEMTKNQVSLTCLVKGFYPSDIAVEWESNGQPENNYKTTP PVLDSDGSFFLYSRLTVDKSRWQEGNVFSCSVMHEALHNHYTQ KSLSLSLG |
| 119 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 120 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSFNRGESASTKGPSVFPLAPSSKS |

| SEQ ID NO | Sequence |
|---|---|
| | TSGGTAALGCLVKDYFPEPVTVSWNSGALTSGVHTFPAVLQSS GLYSLSSVVTVPSSSLGTQTYICNVNHKPSNTKVDKRVEPKSC DKTHTCPPCPAPEAAGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVY TLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPG |
| 121 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 122 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSFNRGESASTKGPSVFPLAPSSKS TSGGTAALGCLVKDYFPEPVTVSWNSGALTSGVHTFPAVLQSS GLYSLSSVVTVPSSSLGTQTYICNVNHKPSNTKVDKRVEPKSC DKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVY TLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPG |
| 123 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 124 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSFNRGESASTKGPSVFPLAPCSRS TSESTAALGCLVKDYFPEPVTVSWNSGALTSGVHTFPAVLQSS GLYSLSSVVTVPSSSLGTKTYTCNVDHKPSNTKVDKRVESKYG PPCPPCPAPEFLGGPSVFLFPPKPKDTLMISRTPEVTCVVVDV SQEDPEVQFNWYVDGVEVHNAKTKPREEQFNSTYRVVSVLTVL HQDWLNGKEYKCKVSNKGLPSSIEKTISKAKGQPREPQVYTLP PSQEEMTKNQVSLTCLVKGFYPSDIAVEWESNGQPENNYKTTP PVLDSDGSFFLYSRLTVDKSRWQEGNVFSCSVMHEALHNHYTQ KSLSLSLG |
| 125 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSVEPKSSRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 126 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSFNRGESASTKGPSVFPLAPCSRS |

| SEQ ID NO | Sequence |
|---|---|
|  | TSESTAALGCLVKDYFPEPVTVSWNSGALTSGVHTFPAVLQSS GLYSLSSVVTVPSSSLGTKTYTCNVDHKPSNTKVDKRVESKYG PPCPPCPAPEFLGGPSVFLFPPKPKDTLYITREPEVTCVVVDV SQEDPEVQFNWYVDGVEVHNAKTKPREEQFNSTYRVVSVLTVL HQDWLNGKEYKCKVSNKGLPSSIEKTISKAKGQPREPQVYTLP PSQEEMTKNQVSLTCLVKGFYPSDIAVEWESNGQPENNYKTTP PVLDSDGSFFLYSRLTVDKSRWQEGNVFSCSVMHEALHNHYTQ KSLSLSLG |
| 127 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSVEPKSSRTVAAPSVFIFPPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| 128 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPEAAGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 129 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 130 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 131 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 132 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGASTKGPSVFPLAPCSR |
| SEQ ID NO | Sequence |
|---|---|
|  | STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 133 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 134 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSLGGGSGASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLYITREPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 135 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSLGGGSGRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 136 | EIVLTQSPATLSLSPGERATLSCRASQSVSYLAWYQQKPGQA PRLLIYDASNRATGIPARFSGSGSGTDFTLTISSLEPEDFAVY YCQQRSNWPPPTFGPGTKVDIKGGGSGGGGQVQLVQSGAEVKK PGSSVKVSCKASGYTFTDQTIHWMRQAPGQGLEWIGYIYPRDD SPKYNENFKGKVTITADKSTSTAYMELSSLRSEDTAVYYCAIP DRSGYAWFIYWGQGTLVTVSSLGGGSGASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 137 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGQVQLVESGGGVVQP GRSLRLSCAASGFIFSSYAMHWVRQAPGNGLEWVAFMSYDGSN KKYADSVKGRFTISRDNSKNTLYLQMNSLRAEDTAVYYCARDR GIAAGGNYYYYGMDVWGQGTTVTVSSLGGGSGRTVAAPSVFIF PPSDEQLKSGTASVVCLLNNFYPREAKVQWKVDNALQSGNSQE SVTEQDSKDSTYSLSSTLTLSKADYEKHKVYACEVTHQGLSSP VTKSFNRGEC |
| 138 | DIQMTQSPSSLSASVGDRVTITCKASRDVAIAVAWYQQKPGKV PKLLIYWASTRHTGVPSRFSGSGSRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSFNRGESASTKGPSVFPLAPSSK |

| SEQ ID NO | Sequence |
|---|---|
| | STSGGTAALGCLVKDYFPEPVTVSWNSGALTSGVHTFPAVLQS SGLYSLSSVVTVPSSSLGTQTYICNVNHKPSNTKVDKRVEPKS CDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPG |
| 139 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSVEPKSSRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 140 | DIQMTQSPSSLSASVGDRVTITCKASRDVAIAVAWYQQKPGKV PKLLIYWASTRHTGVPSRFSGSGSGRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSFNRGESASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 141 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSVEPKSSRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 142 | DIQMTQSPSSLSASVGDRVTITCKASRDVAIAVAWYQQKPGKV PKLLIYWASTRHTGVPSRFSGSGSGRTDFTLTISSLQPEDVADY FCHQYSSYPFTFGSGTKLEIKGGGSGGGGEVQLVESGGGLVQP GRSLRLSCAASGFTFDDYAMHWVRQAPGKGLEWVSAITWNSGH IDYADSVEGRFTISRDNAKNSLYLQMNSLRAEDTAVYYCAKVS YLSTASSLDYWGQGTLVTVSSFNRGESASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLYITREPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLG |
| 143 | DIQMTQSPSSLSASVGDRVTITCRASQGIRNYLAWYQQKPGKA PKLLIYAASTLQSGVPSRFSGSGSGTDFTLTISSLQPEDVATY YCQRYNRAPYTFGQGTKVEIKGGGSGGGGQVQLVQSGAEVKKP GSSVKVSCKASGYTFTDQTIHWMRQAPGQGLEWIGYIYPRDDS PKYNENFKGKVTITADKSTSTAYMELSSLRSEDTAVYYCAIPD RSGYAWFIYWGQGTLVTVSSVEPKSSRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| 144 | MSTESMIRDVELAEEALPKKTGGPQGSRRCLFLSLFSFLIVAG ATTLFCLLHFGVIGPQREEFPRDLSLISPLAQAVRSSSRTPSD KPVAHVVANPQAEGQLQWLNRRANALLANGVELRDNQLVVPSE GLYLIYSQVLFKGQGCPSTHVLLTHTISRIAVSYQTKVNLLSA IKSPCQRETPEGAEAKPWYEPIYLGGVFQLEKGDRLSAEINRP DYLDFAESGQVYFGIIAL |
| 145 | MLGSRAVMLLLLLPWTAQGRAVPGGSSPAWTQCQQLSQKLCTL AWSAHPLVGHMDLREEGDEETTNDVPHIQCGDGCDPQGLRDNS QFCLQRIHQGLIFYEKLLGSDIFTGEPSLLPDSPVGQLHASLL GLSQLLQPEGHHWETQQIPSLSPSQPWQRLLLRFKILRSLQAF VAVAARVFAHGAATLSP |
| 146 | DYAMH |
| 147 | AITWNSGHIDYADSVEG |
| 148 | VSYLSTASSLDY |
| 149 | RASQGIRNYLA |
| 150 | AASTLQS |
| 151 | QRYNRAPYT |
| 152 | SYAMH |
| 153 | FMSYDGSNKKYADSVKG |
| 154 | NYYYYGMDV |
| 155 | RASQSVYSYLA |
| 156 | DASNRAT |
| 157 | QQRSNWPPFT |
| 158 | DQTIH |
| 159 | YIYPRDDSPKYNENFKG |
| 160 | PDRSGYAWFIY |
| 161 | KASRDVAIAVA |
| 162 | WASTRHT |
| 163 | HQYSSYPFT |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A compound comprising a first polypeptide and a second polypeptide, wherein:
   (A) said first polypeptide comprises:
      (i) a light chain variable domain of a first immunoglobulin (VL1) specific for a first target protein;
      (ii) a heavy chain variable domain of a second immunoglobulin (VH2) specific for a second target protein; and
      (iii) a hinge region, a heavy chain constant region 2 (CH2) and a heavy chain constant region 3 (CH3); and
   (B) said second polypeptide comprises:
      (i) a light chain variable domain of the second immunoglobulin (VL2) specific for said second target protein;
      (ii) a heavy chain variable domain of the first immunoglobulin (VH1) specific for said first target protein;
   C), in said first and second polypeptides of (A) and (B):
      (i) said VL1 and VH1 associate to form a binding site that binds said first target protein;
      (ii) said VL2 and VH2 associate to form a binding site that binds said second target protein;
      (iii) said heavy chain constant region 2 (CH2) comprises a tyrosine at position 252, a threonine at position 254 and a glutamic acid a position 256, numbered according to the EU index as in Kabat for the CH2 of a conventional IgG antibody; and
      (iv) said first target protein is TNF-alpha and said second target protein is IL-23A or said first target protein is IL-23A and said second target protein is TNF-alpha,
   and (D), in said first and second polypeptides of (A), (B) and (C):
      (i) said VL1 comprises the amino acid sequence of SEQ ID NO:2, said VH1 comprises the amino acid sequence of SEQ ID NO:1, said VL2 comprises the amino acid sequence of SEQ ID NO:8 and said VH2 comprises the amino acid sequence of SEQ ID NO:7; or
      (ii) said VL1 comprises the amino acid sequence of SEQ ID NO:4 or 6, said VH1 comprises the amino acid sequence of SEQ ID NO:3 or 5, said VL2 comprises the amino acid sequence of SEQ ID NO:8 and said VH2 comprises the amino acid sequence of SEQ ID NO:7; or
      (iii) said VL1 comprises the amino acid sequence of SEQ ID NO:8, said VH1 comprises the amino acid sequence of SEQ ID NO:7, said VL2 comprises the amino acid sequence of SEQ ID NO:2 and said VH2 comprises the amino acid sequence of SEQ ID NO:1; or
      (iv) said VL1 comprises the amino acid sequence of SEQ ID NO:8, said VH1 comprises the amino acid sequence of SEQ ID NO:7, said VL2 comprises the amino acid sequence of SEQ ID NO:4 or 6 and said VH2 comprises the amino acid sequence of SEQ ID NO:3 or 5.

2. The compound according to claim 1, wherein in (D)(ii) said VL1 comprises the amino acid sequence of SEQ ID NO:4, said VH1 comprises the amino acid sequence of SEQ ID NO:3, said VL2 comprises the amino acid sequence of SEQ ID NO:8 and said VH2 comprises the amino acid sequence of SEQ ID NO:7.

3. The compound according to claim 1, wherein in (D)(ii) said VL1 comprises the amino acid sequence of SEQ ID NO:6, said VH1 comprises the amino acid sequence of SEQ ID NO:5, said VL2 comprises the amino acid sequence of SEQ ID NO:8 and said VH2 comprises the amino acid sequence of SEQ ID NO:7.

4. The compound according to claim 1, wherein in (D)(iv) said VL2 comprises the amino acid sequence of SEQ ID NO:4, said VH2 comprises the amino acid sequence of SEQ ID NO:3, said VL1 comprises the amino acid sequence of SEQ ID NO:8 and said VH1 comprises the amino acid sequence of SEQ ID NO:7.

5. The compound according to claim 1, wherein in (D)(iv) said VL2 comprises the amino acid sequence of SEQ ID NO:6, said VH2 comprises the amino acid sequence of SEQ ID NO:5, said VL1 comprises the amino acid sequence of SEQ ID NO:8 and said VH1 comprises the amino acid sequence of SEQ ID NO:7.

6. The compound according to claim 1, wherein said first polypeptide further comprises a first linker between said VL1 and said VH2 and said second polypeptide further comprises a second linker between said VL2 and said VH1.

7. The compound according to claim 6, wherein said first linker or said second linker comprises the amino acid sequence of GGGSGGG (SEQ ID NO:9).

8. The compound according to claim 6, wherein said first linker and said second linker comprise the amino acid sequence of GGGSGGG (SEQ ID NO:9).

9. The compound according to claim 1, wherein said first polypeptide further comprises a heavy chain constant region 1 domain (CH1) and said second polypeptide further comprises a light chain constant region domain (CL), wherein said CL and said CH1 are associated together via a disulfide bond to form a C1 domain.

10. The compound according to claim 9, wherein said first polypeptide further comprises a third linker between said VH2 and said CH1 and said second polypeptide further comprises a fourth linker between said VH1 and said CL.

11. The compound according to claim 10, wherein said third linker comprises the amino acid sequence of FNRGES (SEQ ID NO:11).

12. The compound according to claim 10, wherein said fourth linker comprises the amino acid sequence of VEPKSS (SEQ ID NO:12).

13. The compound according to claim 10, wherein said third linker comprises the amino acid sequence of FNRGES (SEQ ID NO:11) and said fourth linker comprises the amino acid sequence of VEPKSS (SEQ ID NO:12).

14. The compound according to claim 10, wherein said third linker or said fourth linker comprises the amino acid sequence of LGGGSG (SEQ ID NO:10).

15. The compound according to claim 10, wherein said third linker and said fourth linker comprise the amino acid sequence of LGGGSG (SEQ ID NO:10).

16. The compound according to claim 1, wherein said heavy chain constant region 2 (CH2) of (C)(iii) comprises an alanine at positions 234 and an alanine at position 235, numbered according to the EU index as in Kabat for the CH2 of a conventional IgG antibody.

17. The compound according to claim 1, wherein the amino acid sequence of said hinge region, said heavy chain constant region 2 (CH2) or said heavy chain constant region 3 (CH3) is derived from a IgG1 or from a IgG4.

18. The compound according to claim 1, wherein said hinge region comprises the amino acid sequence of EPKSCDKTHTCPPCP (SEQ ID NO:40).

19. The compound according to claim 1, wherein said compound comprises two said first polypeptides and two said second polypeptides, wherein said two first polypeptides are associated together via at least one disulfide bond.

20. The compound according to claim 1, wherein:
(i) said first polypeptide comprises the amino acid sequence of SEQ ID NO:13 and said second polypeptide comprises the amino acid sequence of SEQ ID NO:14;
(ii) said first polypeptide comprises the amino acid sequence of SEQ ID NO:15 and said second polypeptide comprises the amino acid sequence of SEQ ID NO:16;
(iii) said first polypeptide comprises the amino acid sequence of SEQ ID NO:17 and said second polypeptide comprises the amino acid sequence of SEQ ID NO:18;
(iv) said first polypeptide comprises the amino acid sequence of SEQ ID NO:19 and said second polypeptide comprises the amino acid sequence of SEQ ID NO:20;
(v) said first polypeptide comprises the amino acid sequence of SEQ ID NO:21 and said second polypeptide comprises the amino acid sequence of SEQ ID NO:22;
(vi) said first polypeptide comprises the amino acid sequence of SEQ ID NO:23 and said second polypeptide comprises the amino acid sequence of SEQ ID NO:24;
(vii) said first polypeptide comprises the amino acid sequence of SEQ ID NO:25 and said second polypeptide comprises the amino acid sequence of SEQ ID NO:26;
(viii) said first polypeptide comprises the amino acid sequence of SEQ ID NO:27 and said second polypeptide comprises the amino acid sequence of SEQ ID NO:28;
(ix) said first polypeptide comprises the amino acid sequence of SEQ ID NO:29 and said second polypeptide comprises the amino acid sequence of SEQ ID NO:30;
(x) said first polypeptide comprises the amino acid sequence of SEQ ID NO:31 and said second polypeptide comprises the amino acid sequence of SEQ ID NO:32;
(xi) said first polypeptide comprises the amino acid sequence of SEQ ID NO:33 and said second polypeptide comprises the amino acid sequence of SEQ ID NO:34; or
(xii) said first polypeptide comprises the amino acid sequence of SEQ ID NO:35 and said second polypeptide comprises the amino acid sequence of SEQ ID NO:36.

21. The compound according to claim 20, wherein said compound comprises two said first polypeptides and two said second polypeptides, wherein said two first polypeptides are associated together via at least one disulfide bond and wherein each of said first polypeptide is associated to one said second polypeptide via at least one disulfide bond.

22. The compound according to claim 20, wherein said compound comprises two said first polypeptides and two said second polypeptides, wherein each of said first polypeptides comprises a CH1, a CH2 and a CH3 and each of said second polypeptides comprises a CL and wherein the CH2 and CH3 of one of the first polypeptides associates with the CH2 and CH3 of the other of the first polypeptides and the CH1 of each said first polypeptides associates with the CL of one said second polypeptides to form a tetravalent molecule.

23. A composition comprising a compound according to claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 10,059,763 B2 | Page 1 of 1 |
| APPLICATION NO. | : 14/844338 | |
| DATED | : August 28, 2018 | |
| INVENTOR(S) | : Barrett et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 52 days.

Signed and Sealed this
Twenty-third Day of April, 2019

Andrei Iancu
*Director of the United States Patent and Trademark Office*

SEQUENCE LISTING

<160> NUMBER OF SEQ ID NOS: 163

<210> SEQ ID NO 1
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 3
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 4
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 5
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asp Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95

Ala Arg Asp Arg Gly Ile Ala Ala Gly Gly Asn Tyr Tyr Tyr Gly
            100                 105                 110

Met Asp Val Trp Gly Gln Gly Thr Thr Val Thr Val Ser Ser
            115                 120                 125

<210> SEQ ID NO 6
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 7
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Lys Tyr Asn Glu Asn Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:

<223> OTHER INFORMATION: Synthetic Polypeptide

<400> SEQUENCE: 8

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys
            100                 105
```

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

```
Gly Gly Gly Ser Gly Gly Gly
1               5
```

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

```
Leu Gly Gly Gly Ser Gly
1               5
```

<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

```
Phe Asn Arg Gly Glu Ser
1               5
```

<210> SEQ ID NO 12
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 12

```
Val Glu Pro Lys Ser Ser
1               5
```

<210> SEQ ID NO 13

<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
            340                 345                 350

Cys Pro Ala Pro Glu Ala Ala Gly Gly Pro Ser Val Phe Leu Phe Pro
        355                 360                 365

Pro Lys Pro Lys Asp Thr Leu Tyr Ile Thr Arg Glu Pro Glu Val Thr
    370                 375                 380
```

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
        405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 14
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
            195                 200                 205

Tyr Tyr Cys Ala Lys Val Ser Tyr Leu Ser Thr Ala Ser Ser Leu Asp
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
            275                 280                 285

Leu Gln Ser Gly Asn Ser Gln Glu Ser Val Thr Glu Gln Asp Ser Lys
            290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
            325                 330                 335

Ser Ser Pro Val Thr Lys Ser Phe Asn Arg Gly Glu Cys
            340                 345

<210> SEQ ID NO 15
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

```
Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Phe Asn Arg Gly Glu
225                 230                 235                 240

Ser Ala Ser Thr Lys Gly Pro Ser Val Phe Pro Leu Ala Pro Ser Ser
            245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
            275                 280                 285

Ser Gly Val His Thr Phe Pro Ala Val Leu Gln Ser Ser Gly Leu Tyr
            290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
            325                 330                 335

Lys Arg Val Glu Pro Lys Ser Cys Asp Lys Thr His Thr Cys Pro Pro
            340                 345                 350

Cys Pro Ala Pro Glu Ala Ala Gly Gly Pro Ser Val Phe Leu Phe Pro
            355                 360                 365

Pro Lys Pro Lys Asp Thr Leu Tyr Ile Thr Arg Glu Pro Glu Val Thr
            370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
            405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
            435                 440                 445

Asn Lys Ala Leu Pro Ala Pro Ile Glu Lys Thr Ile Ser Lys Ala Lys
            450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
            565                 570

<210> SEQ ID NO 16
<211> LENGTH: 349
<212> TYPE: PRT
<213> ORGANISM: Artificial Sequence
<220> FEATURE:
```

<223> OTHER INFORMATION: Synthetic Polypeptide

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Leu Val Gln
            115                 120                 125

Pro Gly Arg Ser Leu Arg Leu Ser Cys Ala Ala Ser Gly Phe Thr Phe
130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 17
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                      55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Ser Gly
                100                 105                 110

Gly Gly Gly Glu Val Gln Leu Val Glu Ser Gly Gly Leu Val Gln
            115                 120                 125

Pro Gly Arg Ser Leu Arg Leu Ser Cys Ala Ala Ser Gly Phe Thr Phe
        130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
            245                 250                 255

Ser Lys Ser Thr Ser Gly Gly Thr Ala Ala Leu Gly Cys Leu Val Lys
        260                 265                 270

Asp Tyr Phe Pro Glu Pro Val Thr Val Ser Trp Asn Ser Gly Ala Leu
    275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
            325                 330                 335

Asp Lys Arg Val Glu Pro Lys Ser Cys Asp Lys Thr His Thr Cys Pro
        340                 345                 350

Pro Cys Pro Ala Pro Glu Ala Ala Gly Gly Pro Ser Val Phe Leu Phe
    355                 360                 365

Pro Pro Lys Pro Lys Asp Thr Leu Tyr Ile Thr Arg Glu Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
            405                 410                 415
```

```
Arg Glu Glu Gln Tyr Asn Ser Thr Tyr Arg Val Val Ser Val Leu Thr
                420                 425                 430

Val Leu His Gln Asp Trp Leu Asn Gly Lys Glu Tyr Lys Cys Lys Val
            435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 18
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205
```

```
Tyr Tyr Cys Ala Ile Pro Asp Arg Ser Gly Tyr Ala Trp Phe Ile Tyr
    210                 215                 220
Trp Gly Gln Gly Thr Leu Val Thr Val Ser Ser Leu Gly Gly Gly Ser
225                 230                 235                 240
Gly Arg Thr Val Ala Ala Pro Ser Val Phe Ile Phe Pro Pro Ser Asp
                245                 250                 255
Glu Gln Leu Lys Ser Gly Thr Ala Ser Val Val Cys Leu Leu Asn Asn
                260                 265                 270
Phe Tyr Pro Arg Glu Ala Lys Val Gln Trp Lys Val Asp Asn Ala Leu
            275                 280                 285
Gln Ser Gly Asn Ser Gln Glu Ser Val Thr Glu Gln Asp Ser Lys Asp
        290                 295                 300
Ser Thr Tyr Ser Leu Ser Ser Thr Leu Thr Leu Ser Lys Ala Asp Tyr
305                 310                 315                 320
Glu Lys His Lys Val Tyr Ala Cys Glu Val Thr His Gln Gly Leu Ser
                325                 330                 335
Ser Pro Val Thr Lys Ser Phe Asn Arg Gly Glu Cys
                340                 345

<210> SEQ ID NO 19
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 19

Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Gly Ser Gly
            100                 105                 110
Gly Gly Gly Glu Val Gln Leu Val Glu Ser Gly Gly Gly Leu Val Gln
        115                 120                 125
Pro Gly Arg Ser Leu Arg Leu Ser Cys Ala Ala Ser Gly Phe Thr Phe
    130                 135                 140
Asp Asp Tyr Ala Met His Trp Val Arg Gln Ala Pro Gly Lys Gly Leu
145                 150                 155                 160
Glu Trp Val Ser Ala Ile Thr Trp Asn Ser Gly His Ile Asp Tyr Ala
                165                 170                 175
Asp Ser Val Glu Gly Arg Phe Thr Ile Ser Arg Asp Asn Ala Lys Asn
            180                 185                 190
Ser Leu Tyr Leu Gln Met Asn Ser Leu Arg Ala Glu Asp Thr Ala Val
        195                 200                 205
Tyr Tyr Cys Ala Lys Val Ser Tyr Leu Ser Thr Ala Ser Ser Leu Asp
    210                 215                 220
```

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
            245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Tyr Ile Thr Arg Glu Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 20
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Val Glu Pro Lys Ser
225                 230                 235                 240

Ser Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 21
<211> LENGTH: 577
<212> TYPE: PRT
<213> ORGANISM: Artificial Sequence
<220> FEATURE:
<223> OTHER INFORMATION: Synthetic Polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

```
Val Ala Trp Tyr Gln Gln Lys Pro Gly Lys Val Pro Lys Leu Leu Ile
             35                  40                  45

Tyr Trp Ala Ser Thr Arg His Thr Gly Val Pro Ser Arg Phe Ser Gly
 50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                 85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
            115                 120                 125

Pro Gly Arg Ser Leu Arg Leu Ser Cys Ala Ala Ser Gly Phe Ile Phe
        130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Tyr Ile Thr
370                 375                 380

Arg Glu Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
```

```
            450                 455                 460
Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
                500                 505                 510

Ser Asn Gly Gln Pro Glu Asn Asn Tyr Lys Thr Thr Pro Pro Val Leu
                515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 22
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
                100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
                180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240
```

Ser Gly Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
            275                 280                 285

Leu Gln Ser Gly Asn Ser Gln Glu Ser Val Thr Glu Gln Asp Ser Lys
            290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
            325                 330                 335

Ser Ser Pro Val Thr Lys Ser Phe Asn Arg Gly Glu Cys
            340                 345

<210> SEQ ID NO 23
<211> LENGTH: 577
<212> TYPE: PRT
<213> ORGANISM: Artificial Sequence
<220> FEATURE:
<223> OTHER INFORMATION: Synthetic Polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                245                 250                 255

```
Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Tyr Ile Thr
    370                 375                 380

Arg Glu Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 24
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30
```

Leu Ala Trp Tyr Gln Gln Lys Pro Gly Gln Ala Pro Arg Leu Leu Ile
           35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 25
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

-continued

```
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Pro
                 85                  90                  95
Phe Thr Phe Gly Pro Gly Thr Lys Val Asp Ile Lys Gly Gly Gly Ser
            100                 105                 110
Gly Gly Gly Gly Gln Val Gln Leu Val Gln Ser Gly Ala Glu Val Lys
        115                 120                 125
Lys Pro Gly Ser Ser Val Lys Val Ser Cys Lys Ala Ser Gly Tyr Thr
130                 135                 140
Phe Thr Asp Gln Thr Ile His Trp Met Arg Gln Ala Pro Gly Gln Gly
145                 150                 155                 160
Leu Glu Trp Ile Gly Tyr Ile Tyr Pro Arg Asp Asp Ser Pro Lys Tyr
                165                 170                 175
Asn Glu Asn Phe Lys Gly Lys Val Thr Ile Thr Ala Asp Lys Ser Thr
            180                 185                 190
Ser Thr Ala Tyr Met Glu Leu Ser Ser Leu Arg Ser Glu Asp Thr Ala
        195                 200                 205
Val Tyr Tyr Cys Ala Ile Pro Asp Arg Ser Gly Tyr Ala Trp Phe Ile
210                 215                 220
Tyr Trp Gly Gln Gly Thr Leu Val Thr Val Ser Ser Leu Gly Gly Gly
225                 230                 235                 240
Ser Gly Ala Ser Thr Lys Gly Pro Ser Val Phe Pro Leu Ala Pro Ser
                245                 250                 255
Ser Lys Ser Thr Ser Gly Gly Thr Ala Ala Leu Gly Cys Leu Val Lys
            260                 265                 270
Asp Tyr Phe Pro Glu Pro Val Thr Val Ser Trp Asn Ser Gly Ala Leu
        275                 280                 285
Thr Ser Gly Val His Thr Phe Pro Ala Val Leu Gln Ser Ser Gly Leu
290                 295                 300
Tyr Ser Leu Ser Ser Val Val Thr Val Pro Ser Ser Ser Leu Gly Thr
305                 310                 315                 320
Gln Thr Tyr Ile Cys Asn Val Asn His Lys Pro Ser Asn Thr Lys Val
                325                 330                 335
Asp Lys Arg Val Glu Pro Lys Ser Cys Asp Lys Thr His Thr Cys Pro
            340                 345                 350
Pro Cys Pro Ala Pro Glu Ala Ala Gly Gly Pro Ser Val Phe Leu Phe
        355                 360                 365
Pro Pro Lys Pro Lys Asp Thr Leu Tyr Ile Thr Arg Glu Pro Glu Val
370                 375                 380
Thr Cys Val Val Val Asp Val Ser His Glu Asp Pro Glu Val Lys Phe
385                 390                 395                 400
Asn Trp Tyr Val Asp Gly Val Glu Val His Asn Ala Lys Thr Lys Pro
                405                 410                 415
Arg Glu Glu Gln Tyr Asn Ser Thr Tyr Arg Val Val Ser Val Leu Thr
            420                 425                 430
Val Leu His Gln Asp Trp Leu Asn Gly Lys Glu Tyr Lys Cys Lys Val
        435                 440                 445
Ser Asn Lys Ala Leu Pro Ala Pro Ile Glu Lys Thr Ile Ser Lys Ala
450                 455                 460
Lys Gly Gln Pro Arg Glu Pro Gln Val Tyr Thr Leu Pro Pro Ser Arg
```

```
                465                 470                 475                 480
Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
                515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 26
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
        130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
                180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Asn Tyr Tyr
        210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
```

```
                    260                 265                 270
Val Cys Leu Leu Asn Asn Phe Tyr Pro Arg Glu Ala Lys Val Gln Trp
                275                 280                 285
Lys Val Asp Asn Ala Leu Gln Ser Gly Asn Ser Gln Glu Ser Val Thr
            290                 295                 300
Glu Gln Asp Ser Lys Asp Ser Thr Tyr Ser Leu Ser Ser Thr Leu Thr
305                 310                 315                 320
Leu Ser Lys Ala Asp Tyr Glu Lys His Lys Val Tyr Ala Cys Glu Val
                325                 330                 335
Thr His Gln Gly Leu Ser Ser Pro Val Thr Lys Ser Phe Asn Arg Gly
                340                 345                 350
Glu Cys

<210> SEQ ID NO 27
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 27

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Tyr Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Phe Thr Phe Gly Pro Gly Thr Lys Val Asp Ile Lys Gly Gly Gly Ser
            100                 105                 110
Gly Gly Gly Gly Gln Val Gln Leu Val Gln Ser Gly Ala Glu Val Lys
        115                 120                 125
Lys Pro Gly Ser Ser Val Lys Val Ser Cys Lys Ala Ser Gly Tyr Thr
    130                 135                 140
Phe Thr Asp Gln Thr Ile His Trp Met Arg Gln Ala Pro Gly Gln Gly
145                 150                 155                 160
Leu Glu Trp Ile Gly Tyr Ile Tyr Pro Arg Asp Asp Ser Pro Lys Tyr
                165                 170                 175
Asn Glu Asn Phe Lys Gly Lys Val Thr Ile Thr Ala Asp Lys Ser Thr
            180                 185                 190
Ser Thr Ala Tyr Met Glu Leu Ser Ser Leu Arg Ser Glu Asp Thr Ala
        195                 200                 205
Val Tyr Tyr Cys Ala Ile Pro Asp Arg Ser Gly Tyr Ala Trp Phe Ile
    210                 215                 220
Tyr Trp Gly Gln Gly Thr Leu Val Thr Val Ser Ser Phe Asn Arg Gly
225                 230                 235                 240
Glu Ser Ala Ser Thr Lys Gly Pro Ser Val Phe Pro Leu Ala Pro Ser
                245                 250                 255
Ser Lys Ser Thr Ser Gly Gly Thr Ala Ala Leu Gly Cys Leu Val Lys
            260                 265                 270
```

```
Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
        290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
            325                 330                 335

Asp Lys Arg Val Glu Pro Lys Ser Cys Asp Lys Thr His Thr Cys Pro
        340                 345                 350

Pro Cys Pro Ala Pro Glu Ala Ala Gly Gly Pro Ser Val Phe Leu Phe
            355                 360                 365

Pro Pro Lys Pro Lys Asp Thr Leu Tyr Ile Thr Arg Glu Pro Glu Val
        370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
            405                 410                 415

Arg Glu Glu Gln Tyr Asn Ser Thr Tyr Arg Val Val Ser Val Leu Thr
        420                 425                 430

Val Leu His Gln Asp Trp Leu Asn Gly Lys Glu Tyr Lys Cys Lys Val
            435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
            485                 490                 495

Phe Tyr Pro Ser Asp Ile Ala Val Glu Trp Glu Ser Asn Gly Gln Pro
        500                 505                 510

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
            565                 570

<210> SEQ ID NO 28
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60
```

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Tyr Pro Phe
            85                  90                  95

Thr Phe Gly Ser Gly Thr Lys Leu Glu Ile Lys Gly Gly Ser Gly
            100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 29
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Tyr Ile Thr Arg Glu Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
```

```
                        485                 490                 495
Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
                515                 520                 525

Phe Phe Leu Tyr Ser Lys Leu Thr Val Asp Lys Ser Arg Trp Gln Gln
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 30
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
```

```
            275                 280                 285
Lys Val Asp Asn Ala Leu Gln Ser Gly Asn Ser Gln Glu Ser Val Thr
290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 31
<211> LENGTH: 577
<212> TYPE: PRT
<213> ORGANISM: Artificial Sequence
<220> FEATURE:
<223> OTHER INFORMATION: Synthetic Polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Val Glu Ser Gly Gly Gly Val Val Gln
            115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285
```

```
Asn Ser Gly Ala Leu Thr Ser Gly Val His Thr Phe Pro Ala Val Leu
            290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Tyr Ile Thr
    370                 375                 380

Arg Glu Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 32
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys Gly Gly Gly Ser
        100                 105                 110

Gly Gly Gly Gly Gln Val Gln Leu Val Gln Ser Gly Ala Glu Val Lys
    115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 33
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

-continued

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Tyr Ile Thr Arg Glu Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro

-continued

```
                500                 505                 510
Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 34
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
```

```
                290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
                340                 345                 350

Glu Cys

<210> SEQ ID NO 35
<211> LENGTH: 577
<212> TYPE: PRT
<213> ORGANISM: Artificial Sequence
<220> FEATURE:
<223> OTHER INFORMATION: Synthetic Polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Val Glu Ser Gly Gly Gly Val Val Gln
            115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
                180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                245                 250                 255

Pro Leu Ala Pro Ser Ser Lys Ser Thr Ser Gly Gly Thr Ala Ala Leu
                260                 265                 270

Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
    290                 295                 300
```

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Tyr Ile Thr
    370                 375                 380

Arg Glu Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 36
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys Gly Gly Gly Ser
        100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 37
<211> LENGTH: 326
<212> TYPE: PRT
<213> ORGANISM: Artificial Sequence
<220> FEATURE:
<223> OTHER INFORMATION: Synthetic Polypeptide

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 38
<211> LENGTH: 326
<212> TYPE: PRT
<213> ORGANISM: Artificial Sequence
<220> FEATURE:
<223> OTHER INFORMATION: Synthetic Polypeptide

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125
```

```
Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 39
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 40
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 40

Glu Pro Lys Ser Cys Asp Lys Thr His Thr Cys Pro Pro Cys Pro
1               5                   10                  15

<210> SEQ ID NO 41
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 42

<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 43

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

| Ser | Thr | Ser | Gly | Gly | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Leu | Gly | Thr | Gln | Thr |
|---|---|---|---|---|---|---|---|---|---|---|---|---|---|---|
| 65 | | | | | 70 | | | | | 75 | | | | 80 |

| Tyr | Ile | Cys | Asn | Val | Asn | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Arg | Val | Glu | Pro | Lys | Ser | Cys | Asp | Lys | Thr | His | Thr | Cys | Pro | Pro | Cys |
|---|---|---|---|---|---|---|---|---|---|---|---|---|---|---|---|
| | | | 100 | | | | | 105 | | | | | 110 | | |

| Pro | Ala | Pro | Glu | Ala | Ala | Gly | Gly | Pro | Ser | Val | Phe | Leu | Phe | Pro | Pro |
|---|---|---|---|---|---|---|---|---|---|---|---|---|---|---|---|
| | | 115 | | | | | 120 | | | | | 125 | | | |

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| 130 | | | | | 135 | | | | | 140 | | | | | |

| Val | Val | Val | Asp | Val | Ser | His | Glu | Asp | Pro | Glu | Val | Lys | Phe | Asn | Trp |
|---|---|---|---|---|---|---|---|---|---|---|---|---|---|---|---|
| 145 | | | | | 150 | | | | | 155 | | | | | 160 |

| Tyr | Val | Asp | Gly | Val | Glu | Val | His | Asn | Ala | Lys | Thr | Lys | Pro | Arg | Glu |
|---|---|---|---|---|---|---|---|---|---|---|---|---|---|---|---|
| | | | 165 | | | | | 170 | | | | | 175 | | |

| Glu | Gln | Tyr | Asn | Ser | Thr | Tyr | Arg | Val | Val | Ser | Val | Leu | Thr | Val | Leu |
|---|---|---|---|---|---|---|---|---|---|---|---|---|---|---|---|
| | | | 180 | | | | | 185 | | | | | 190 | | |

| His | Gln | Asp | Trp | Leu | Asn | Gly | Lys | Glu | Tyr | Lys | Cys | Lys | Val | Ser | Asn |
|---|---|---|---|---|---|---|---|---|---|---|---|---|---|---|---|
| | | 195 | | | | | 200 | | | | | 205 | | | |

| Lys | Ala | Leu | Pro | Ala | Pro | Ile | Glu | Lys | Thr | Ile | Ser | Lys | Ala | Lys | Gly |
|---|---|---|---|---|---|---|---|---|---|---|---|---|---|---|---|
| | 210 | | | | | 215 | | | | | 220 | | | | |

| Gln | Pro | Arg | Glu | Pro | Gln | Val | Tyr | Thr | Leu | Pro | Pro | Ser | Arg | Glu | Glu |
|---|---|---|---|---|---|---|---|---|---|---|---|---|---|---|---|
| 225 | | | | | 230 | | | | | 235 | | | | | 240 |

| Met | Thr | Lys | Asn | Gln | Val | Ser | Leu | Thr | Cys | Leu | Val | Lys | Gly | Phe | Tyr |
|---|---|---|---|---|---|---|---|---|---|---|---|---|---|---|---|
| | | | | 245 | | | | | 250 | | | | | 255 | |

| Pro | Ser | Asp | Ile | Ala | Val | Glu | Trp | Glu | Ser | Asn | Gly | Gln | Pro | Glu | Asn |
|---|---|---|---|---|---|---|---|---|---|---|---|---|---|---|---|
| | | | 260 | | | | | 265 | | | | | 270 | | |

| Asn | Tyr | Lys | Thr | Thr | Pro | Pro | Val | Leu | Asp | Ser | Asp | Gly | Ser | Phe | Phe |
|---|---|---|---|---|---|---|---|---|---|---|---|---|---|---|---|
| | | | 275 | | | | | 280 | | | | | 285 | | |

| Leu | Tyr | Ser | Lys | Leu | Thr | Val | Asp | Lys | Ser | Arg | Trp | Gln | Gln | Gly | Asn |
|---|---|---|---|---|---|---|---|---|---|---|---|---|---|---|---|
| | 290 | | | | | 295 | | | | | 300 | | | | |

| Val | Phe | Ser | Cys | Ser | Val | Met | His | Glu | Ala | Leu | His | Asn | His | Tyr | Thr |
|---|---|---|---|---|---|---|---|---|---|---|---|---|---|---|---|
| 305 | | | | | 310 | | | | | 315 | | | | | 320 |

| Gln | Lys | Ser | Leu | Ser | Leu | Ser | Pro | Gly |
|---|---|---|---|---|---|---|---|---|
| | | | | 325 | | | | |

<210> SEQ ID NO 44
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 44

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Arg | Asn | Tyr |
|---|---|---|---|---|---|---|---|---|---|---|---|---|---|---|---|

```
            20                  25                  30
Leu Ala Trp Tyr Gln Gln Lys Pro Gly Lys Ala Pro Lys Leu Leu Ile
            35                  40                  45
Tyr Ala Ala Ser Thr Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Arg Tyr Asn Arg Ala Pro Tyr
                85                  90                  95
Thr Phe Gly Gln Gly Thr Lys Val Glu Ile Lys Gly Gly Ser Gly
            100                 105                 110
Gly Gly Gly Gln Val Gln Leu Val Gln Ser Gly Ala Glu Val Lys Lys
            115                 120                 125
Pro Gly Ser Ser Val Lys Val Ser Cys Lys Ala Ser Gly Tyr Thr Phe
            130                 135                 140
Thr Asp Gln Thr Ile His Trp Met Arg Gln Ala Pro Gly Gln Gly Leu
145                 150                 155                 160
Glu Trp Ile Gly Tyr Ile Tyr Pro Arg Asp Asp Ser Pro Lys Tyr Asn
                165                 170                 175
Glu Asn Phe Lys Gly Lys Val Thr Ile Thr Ala Asp Lys Ser Thr Ser
                180                 185                 190
Thr Ala Tyr Met Glu Leu Ser Ser Leu Arg Ser Glu Asp Thr Ala Val
            195                 200                 205
Tyr Tyr Cys Ala Ile Pro Asp Arg Ser Gly Tyr Ala Trp Phe Ile Tyr
            210                 215                 220
Trp Gly Gln Gly Thr Leu Val Thr Val Ser Ser Leu Gly Gly Gly Ser
225                 230                 235                 240
Gly Ala Ser Thr Lys Gly Pro Ser Val Phe Pro Leu Ala Pro Ser Ser
                245                 250                 255
Lys Ser Thr Ser Gly Gly Thr Ala Ala Leu Gly Cys Leu Val Lys Asp
                260                 265                 270
Tyr Phe Pro Glu Pro Val Thr Val Ser Trp Asn Ser Gly Ala Leu Thr
            275                 280                 285
Ser Gly Val His Thr Phe Pro Ala Val Leu Gln Ser Ser Gly Leu Tyr
            290                 295                 300
Ser Leu Ser Ser Val Val Thr Val Pro Ser Ser Ser Leu Gly Thr Gln
305                 310                 315                 320
Thr Tyr Ile Cys Asn Val Asn His Lys Pro Ser Asn Thr Lys Val Asp
                325                 330                 335
Lys Arg Val Glu Pro Lys Ser Cys Asp Lys Thr His Thr Cys Pro Pro
            340                 345                 350
Cys Pro Ala Pro Glu Ala Ala Gly Gly Pro Ser Val Phe Leu Phe Pro
            355                 360                 365
Pro Lys Pro Lys Asp Thr Leu Met Ile Ser Arg Thr Pro Glu Val Thr
            370                 375                 380
Cys Val Val Val Asp Val Ser His Glu Asp Pro Glu Val Lys Phe Asn
385                 390                 395                 400
Trp Tyr Val Asp Gly Val Glu Val His Asn Ala Lys Thr Lys Pro Arg
                405                 410                 415
Glu Glu Gln Tyr Asn Ser Thr Tyr Arg Val Val Ser Val Leu Thr Val
            420                 425                 430
Leu His Gln Asp Trp Leu Asn Gly Lys Glu Tyr Lys Cys Lys Val Ser
            435                 440                 445
```

```
Asn Lys Ala Leu Pro Ala Pro Ile Glu Lys Thr Ile Ser Lys Ala Lys
        450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
                565                 570

<210> SEQ ID NO 45
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Leu Gly Gly Gly
225                 230                 235                 240
```

Ser Gly Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
        260                 265                 270

Asn Phe Tyr Pro Arg Glu Ala Lys Val Gln Trp Lys Val Asp Asn Ala
    275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 46
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
                245                 250                 255

```
Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 47
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Val Glu Pro Lys Ser
225                 230                 235                 240

Ser Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 48
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 48

Asp Ile Gln Met Thr Gln Ser Pro Ser Ser Leu Ser Ala Ser Val Gly
 1               5                  10                  15

Asp Arg Val Thr Ile Thr Cys Lys Ala Ser Arg Asp Val Ala Ile Ala
             20                  25                  30

Val Ala Trp Tyr Gln Gln Lys Pro Gly Lys Val Pro Lys Leu Leu Ile
         35                  40                  45

Tyr Trp Ala Ser Thr Arg His Thr Gly Val Pro Ser Arg Phe Ser Gly
     50                  55                  60
```

```
Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                 85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
            115                 120                 125

Pro Gly Arg Ser Leu Arg Leu Ser Cys Ala Ala Ser Gly Phe Ile Phe
        130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
        450                 455                 460

Thr Ile Ser Lys Ala Lys Gly Gln Pro Arg Glu Pro Gln Val Tyr Thr
465                 470                 475                 480
```

```
Leu Pro Pro Ser Arg Glu Glu Met Thr Lys Asn Gln Val Ser Leu Thr
            485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
            515                 520                 525

Asp Ser Asp Gly Ser Phe Phe Leu Tyr Ser Lys Leu Thr Val Asp Lys
            530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
            565                 570                 575

<210> SEQ ID NO 49
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
            165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
        210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
            260                 265                 270
```

```
Asn Phe Tyr Pro Arg Glu Ala Lys Val Gln Trp Lys Val Asp Asn Ala
            275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 50
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285
```

```
Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

<210> SEQ ID NO 51
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys Gly Gly Gly Ser
        100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
        130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
        260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
        290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 52
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

-continued

Phe Thr Phe Gly Pro Gly Thr Lys Val Asp Ile Lys Gly Gly Ser
             100                 105                 110

Gly Gly Gly Gly Gln Val Gln Leu Val Gln Ser Gly Ala Glu Val Lys
         115                 120                 125

Lys Pro Gly Ser Ser Val Lys Val Ser Cys Lys Ala Ser Gly Tyr Thr
         130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                 165                 170                 175

Asn Glu Asn Phe Lys Gly Lys Val Thr Ile Thr Ala Asp Lys Ser Thr
             180                 185                 190

Ser Thr Ala Tyr Met Glu Leu Ser Ser Leu Arg Ser Glu Asp Thr Ala
         195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Cys
             245                 250                 255

Ser Arg Ser Thr Ser Glu Ser Thr Ala Ala Leu Gly Cys Leu Val Lys
         260                 265                 270

Asp Tyr Phe Pro Glu Pro Val Thr Val Ser Trp Asn Ser Gly Ala Leu
         275                 280                 285

Thr Ser Gly Val His Thr Phe Pro Ala Val Leu Gln Ser Ser Gly Leu
         290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                 325                 330                 335

Asp Lys Arg Val Glu Ser Lys Tyr Gly Pro Pro Cys Pro Pro Cys Pro
             340                 345                 350

Ala Pro Glu Phe Leu Gly Gly Pro Ser Val Phe Leu Phe Pro Pro Lys
         355                 360                 365

Pro Lys Asp Thr Leu Met Ile Ser Arg Thr Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                 405                 410                 415

Gln Phe Asn Ser Thr Tyr Arg Val Val Ser Val Leu Thr Val Leu His
             420                 425                 430

Gln Asp Trp Leu Asn Gly Lys Glu Tyr Lys Cys Lys Val Ser Asn Lys
         435                 440                 445

Gly Leu Pro Ser Ser Ile Glu Lys Thr Ile Ser Lys Ala Lys Gly Gln
         450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                 485                 490                 495

Ser Asp Ile Ala Val Glu Trp Glu Ser Asn Gly Gln Pro Glu Asn Asn
             500                 505                 510

Tyr Lys Thr Thr Pro Pro Val Leu Asp Ser Asp Gly Ser Phe Phe Leu

-continued

```
            515                 520                 525
Tyr Ser Arg Leu Thr Val Asp Lys Ser Arg Trp Gln Glu Gly Asn Val
            530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 53
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
```

```
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
                340                 345                 350

Glu Cys

<210> SEQ ID NO 54
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
                100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
                180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
                260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320
```

```
Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
        355                 360                 365

Pro Lys Asp Thr Leu Tyr Ile Thr Arg Glu Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Gly Leu Pro Ser Ser Ile Glu Lys Thr Ile Ser Lys Ala Lys Gly Gln
    450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Arg Leu Thr Val Asp Lys Ser Arg Trp Gln Glu Gly Asn Val
530                 535                 540

Phe Ser Cys Ser Val Met His Glu Ala Leu His Asn His Tyr Thr Gln
545                 550                 555                 560

Lys Ser Leu Ser Leu Ser Leu Gly
                565
```

<210> SEQ ID NO 55
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110
```

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
        130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 56
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

```
Gly Gly Gly Gly Gln Val Gln Leu Val Gln Ser Gly Ala Glu Val Lys
            115                 120                 125
Lys Pro Gly Ser Ser Val Lys Val Ser Cys Lys Ala Ser Gly Tyr Thr
130                 135                 140
Phe Thr Asp Gln Thr Ile His Trp Met Arg Gln Ala Pro Gly Gln Gly
145                 150                 155                 160
Leu Glu Trp Ile Gly Tyr Ile Tyr Pro Arg Asp Asp Ser Pro Lys Tyr
                165                 170                 175
Asn Glu Asn Phe Lys Gly Lys Val Thr Ile Thr Ala Asp Lys Ser Thr
            180                 185                 190
Ser Thr Ala Tyr Met Glu Leu Ser Ser Leu Arg Ser Glu Asp Thr Ala
        195                 200                 205
Val Tyr Tyr Cys Ala Ile Pro Asp Arg Ser Gly Tyr Ala Trp Phe Ile
    210                 215                 220
Tyr Trp Gly Gln Gly Thr Leu Val Thr Val Ser Ser Leu Gly Gly Gly
225                 230                 235                 240
Ser Gly Ala Ser Thr Lys Gly Pro Ser Val Phe Pro Leu Ala Pro Cys
                245                 250                 255
Ser Arg Ser Thr Ser Glu Ser Thr Ala Ala Leu Gly Cys Leu Val Lys
            260                 265                 270
Asp Tyr Phe Pro Glu Pro Val Thr Val Ser Trp Asn Ser Gly Ala Leu
        275                 280                 285
Thr Ser Gly Val His Thr Phe Pro Ala Val Leu Gln Ser Ser Gly Leu
    290                 295                 300
Tyr Ser Leu Ser Ser Val Val Thr Val Pro Ser Ser Ser Leu Gly Thr
305                 310                 315                 320
Lys Thr Tyr Thr Cys Asn Val Asp His Lys Pro Ser Asn Thr Lys Val
                325                 330                 335
Asp Lys Arg Val Glu Ser Lys Tyr Gly Pro Pro Cys Pro Pro Cys Pro
            340                 345                 350
Ala Pro Glu Phe Leu Gly Gly Pro Ser Val Phe Leu Phe Pro Pro Lys
        355                 360                 365
Pro Lys Asp Thr Leu Met Ile Ser Arg Thr Pro Glu Val Thr Cys Val
    370                 375                 380
Val Val Asp Val Ser Gln Glu Asp Pro Glu Val Gln Phe Asn Trp Tyr
385                 390                 395                 400
Val Asp Gly Val Glu Val His Asn Ala Lys Thr Lys Pro Arg Glu Glu
                405                 410                 415
Gln Phe Asn Ser Thr Tyr Arg Val Val Ser Val Leu Thr Val Leu His
            420                 425                 430
Gln Asp Trp Leu Asn Gly Lys Glu Tyr Lys Cys Lys Val Ser Asn Lys
        435                 440                 445
Gly Leu Pro Ser Ser Ile Glu Lys Thr Ile Ser Lys Ala Lys Gly Gln
    450                 455                 460
Pro Arg Glu Pro Gln Val Tyr Thr Leu Pro Pro Ser Gln Glu Glu Met
465                 470                 475                 480
Thr Lys Asn Gln Val Ser Leu Thr Cys Leu Val Lys Gly Phe Tyr Pro
                485                 490                 495
Ser Asp Ile Ala Val Glu Trp Glu Ser Asn Gly Gln Pro Glu Asn Asn
            500                 505                 510
Tyr Lys Thr Thr Pro Pro Val Leu Asp Ser Asp Gly Ser Phe Phe Leu
        515                 520                 525
Tyr Ser Arg Leu Thr Val Asp Lys Ser Arg Trp Gln Glu Gly Asn Val
```

```
                530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 57
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
            245                 250                 255

Ile Phe Pro Pro Ser Asp Glu Gln Leu Lys Ser Gly Thr Ala Ser Val
        260                 265                 270

Val Cys Leu Leu Asn Asn Phe Tyr Pro Arg Glu Ala Lys Val Gln Trp
    275                 280                 285

Lys Val Asp Asn Ala Leu Gln Ser Gly Asn Ser Gln Glu Ser Val Thr
        290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
```

```
                    325                 330                 335
Thr His Gln Gly Leu Ser Ser Pro Val Thr Lys Ser Phe Asn Arg Gly
                340                 345                 350

Glu Cys

<210> SEQ ID NO 58
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335
```

Asp Lys Arg Val Glu Ser Lys Tyr Gly Pro Pro Cys Pro Pro Cys Pro
                340                 345                 350

Ala Pro Glu Phe Leu Gly Gly Pro Ser Val Phe Leu Phe Pro Pro Lys
            355                 360                 365

Pro Lys Asp Thr Leu Tyr Ile Thr Arg Glu Pro Glu Val Thr Cys Val
        370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Gly Leu Pro Ser Ser Ile Glu Lys Thr Ile Ser Lys Ala Lys Gly Gln
450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Arg Leu Thr Val Asp Lys Ser Arg Trp Gln Glu Gly Asn Val
530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 59
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

```
Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
                180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Asn Tyr Tyr
210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 60
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
                100                 105                 110

Gly Gly Gly Gly Gln Val Gln Leu Val Gln Ser Gly Ala Glu Val Lys
            115                 120                 125
```

-continued

```
Lys Pro Gly Ser Ser Val Lys Val Ser Cys Lys Ala Ser Gly Tyr Thr
            130                 135                 140
Phe Thr Asp Gln Thr Ile His Trp Met Arg Gln Ala Pro Gly Gln Gly
145                 150                 155                 160
Leu Glu Trp Ile Gly Tyr Ile Tyr Pro Arg Asp Asp Ser Pro Lys Tyr
                    165                 170                 175
Asn Glu Asn Phe Lys Gly Lys Val Thr Ile Thr Ala Asp Lys Ser Thr
                180                 185                 190
Ser Thr Ala Tyr Met Glu Leu Ser Ser Leu Arg Ser Glu Asp Thr Ala
            195                 200                 205
Val Tyr Tyr Cys Ala Ile Pro Asp Arg Ser Gly Tyr Ala Trp Phe Ile
210                 215                 220
Tyr Trp Gly Gln Gly Thr Leu Val Thr Val Ser Ser Phe Asn Arg Gly
225                 230                 235                 240
Glu Ser Ala Ser Thr Lys Gly Pro Ser Val Phe Pro Leu Ala Pro Ser
                245                 250                 255
Ser Lys Ser Thr Ser Gly Gly Thr Ala Ala Leu Gly Cys Leu Val Lys
            260                 265                 270
Asp Tyr Phe Pro Glu Pro Val Thr Val Ser Trp Asn Ser Gly Ala Leu
            275                 280                 285
Thr Ser Gly Val His Thr Phe Pro Ala Val Leu Gln Ser Ser Gly Leu
        290                 295                 300
Tyr Ser Leu Ser Ser Val Val Thr Val Pro Ser Ser Ser Leu Gly Thr
305                 310                 315                 320
Gln Thr Tyr Ile Cys Asn Val Asn His Lys Pro Ser Asn Thr Lys Val
                325                 330                 335
Asp Lys Arg Val Glu Pro Lys Ser Cys Asp Lys Thr His Thr Cys Pro
                340                 345                 350
Pro Cys Pro Ala Pro Glu Ala Ala Gly Gly Pro Ser Val Phe Leu Phe
            355                 360                 365
Pro Pro Lys Pro Lys Asp Thr Leu Met Ile Ser Arg Thr Pro Glu Val
            370                 375                 380
Thr Cys Val Val Val Asp Val Ser His Glu Asp Pro Glu Val Lys Phe
385                 390                 395                 400
Asn Trp Tyr Val Asp Gly Val Glu Val His Asn Ala Lys Thr Lys Pro
                405                 410                 415
Arg Glu Glu Gln Tyr Asn Ser Thr Tyr Arg Val Val Ser Val Leu Thr
            420                 425                 430
Val Leu His Gln Asp Trp Leu Asn Gly Lys Glu Tyr Lys Cys Lys Val
            435                 440                 445
Ser Asn Lys Ala Leu Pro Ala Pro Ile Glu Lys Thr Ile Ser Lys Ala
450                 455                 460
Lys Gly Gln Pro Arg Glu Pro Gln Val Tyr Thr Leu Pro Pro Ser Arg
465                 470                 475                 480
Glu Glu Met Thr Lys Asn Gln Val Ser Leu Thr Cys Leu Val Lys Gly
                485                 490                 495
Phe Tyr Pro Ser Asp Ile Ala Val Glu Trp Glu Ser Asn Gly Gln Pro
                500                 505                 510
Glu Asn Asn Tyr Lys Thr Pro Pro Val Leu Asp Ser Asp Gly Ser
            515                 520                 525
Phe Phe Leu Tyr Ser Lys Leu Thr Val Asp Lys Ser Arg Trp Gln Gln
    530                 535                 540
Gly Asn Val Phe Ser Cys Ser Val Met His Glu Ala Leu His Asn His
```

```
                545                 550                 555                 560
Tyr Thr Gln Lys Ser Leu Ser Leu Ser Pro Gly
                    565                 570

<210> SEQ ID NO 61
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
```

Glu Cys

<210> SEQ ID NO 62
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

```
Pro Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
                420                 425                 430

Val Leu His Gln Asp Trp Leu Asn Gly Lys Glu Tyr Lys Cys Lys Val
                435                 440                 445

Ser Asn Lys Ala Leu Pro Ala Pro Ile Glu Lys Thr Ile Ser Lys Ala
                450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
                515                 520                 525

Phe Phe Leu Tyr Ser Lys Leu Thr Val Asp Lys Ser Arg Trp Gln Gln
                530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 63
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
                35                  40                  45

Tyr Trp Ala Ser Thr Arg His Thr Gly Val Pro Ser Arg Phe Ser Gly
            50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
                130                 135                 140
```

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 64
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

```
Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
        210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
        290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
        355                 360                 365

Pro Lys Asp Thr Leu Met Ile Ser Arg Thr Pro Glu Val Thr Cys Val
        370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Gly Leu Pro Ser Ser Ile Glu Lys Thr Ile Ser Lys Ala Lys Gly Gln
        450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Arg Leu Thr Val Asp Lys Ser Arg Trp Gln Glu Gly Asn Val
        530                 535                 540

Phe Ser Cys Ser Val Met His Glu Ala Leu His Asn His Tyr Thr Gln
545                 550                 555                 560

Lys Ser Leu Ser Leu Ser Leu Gly
```

<210> SEQ ID NO 65
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 66
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 66

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
        355                 360                 365
```

Pro Lys Asp Thr Leu Tyr Ile Thr Arg Glu Pro Glu Val Thr Cys Val
            370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Gly Leu Pro Ser Ser Ile Glu Lys Thr Ile Ser Lys Ala Lys Gly Gln
    450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Arg Leu Thr Val Asp Lys Ser Arg Trp Gln Glu Gly Asn Val
    530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 67
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

```
Glu Trp Val Ala Phe Met Ser Tyr Asp Gly Ser Asn Lys Lys Tyr Ala
                165                 170                 175
Asp Ser Val Lys Gly Arg Phe Thr Ile Ser Arg Asp Asn Ser Lys Asn
            180                 185                 190
Thr Leu Tyr Leu Gln Met Asn Ser Leu Arg Ala Glu Asp Thr Ala Val
        195                 200                 205
Tyr Tyr Cys Ala Arg Asp Arg Gly Ile Ala Ala Gly Asn Tyr Tyr
    210                 215                 220
Tyr Tyr Gly Met Asp Val Trp Gly Gln Gly Thr Thr Val Thr Val Ser
225                 230                 235                 240
Ser Val Glu Pro Lys Ser Ser Arg Thr Val Ala Ala Pro Ser Val Phe
            245                 250                 255
Ile Phe Pro Pro Ser Asp Glu Gln Leu Lys Ser Gly Thr Ala Ser Val
        260                 265                 270
Val Cys Leu Leu Asn Asn Phe Tyr Pro Arg Glu Ala Lys Val Gln Trp
    275                 280                 285
Lys Val Asp Asn Ala Leu Gln Ser Gly Asn Ser Gln Glu Ser Val Thr
            290                 295                 300
Glu Gln Asp Ser Lys Asp Ser Thr Tyr Ser Leu Ser Ser Thr Leu Thr
305                 310                 315                 320
Leu Ser Lys Ala Asp Tyr Glu Lys His Lys Val Tyr Ala Cys Glu Val
                325                 330                 335
Thr His Gln Gly Leu Ser Ser Pro Val Thr Lys Ser Phe Asn Arg Gly
            340                 345                 350
Glu Cys

<210> SEQ ID NO 68
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 68

Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Gly Ser Gly
            100                 105                 110
Gly Gly Gly Gln Val Gln Leu Val Glu Ser Gly Gly Val Val Gln
        115                 120                 125
Pro Gly Arg Ser Leu Arg Leu Ser Cys Ala Ala Ser Gly Phe Ile Phe
    130                 135                 140
Ser Ser Tyr Ala Met His Trp Val Arg Gln Ala Pro Gly Asn Gly Leu
145                 150                 155                 160
```

```
Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575
```

<210> SEQ ID NO 69
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 69

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 70
<211> LENGTH: 573
<212> TYPE: PRT

<213> ORGANISM: Artificial Sequence
<220> FEATURE:
<223> OTHER INFORMATION: Synthetic Polypeptide

<400> SEQUENCE: 70

Asp Ile Gln Met Thr Gln Ser Pro Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
            245                 250                 255

Pro Leu Ala Pro Cys Ser Arg Ser Thr Ser Glu Ser Thr Ala Ala Leu
        260                 265                 270

Gly Cys Leu Val Lys Asp Tyr Phe Pro Glu Pro Val Thr Val Ser Trp
275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
            325                 330                 335

Ser Asn Thr Lys Val Asp Lys Arg Val Glu Ser Lys Tyr Gly Pro Pro
        340                 345                 350

Cys Pro Pro Cys Pro Ala Pro Glu Phe Leu Gly Gly Pro Ser Val Phe
355                 360                 365

Leu Phe Pro Pro Lys Pro Lys Asp Thr Leu Met Ile Ser Arg Thr Pro
370                 375                 380

Glu Val Thr Cys Val Val Val Asp Val Ser Gln Glu Asp Pro Glu Val

```
                385                 390                 395                 400
        Gln Phe Asn Trp Tyr Val Asp Gly Val Glu Val His Asn Ala Lys Thr
                            405                 410                 415

Lys Pro Arg Glu Glu Gln Phe Asn Ser Thr Tyr Arg Val Val Ser Val
                        420                 425                 430

Leu Thr Val Leu His Gln Asp Trp Leu Asn Gly Lys Glu Tyr Lys Cys
                    435                 440                 445

Lys Val Ser Asn Lys Gly Leu Pro Ser Ser Ile Glu Lys Thr Ile Ser
                450                 455                 460

Lys Ala Lys Gly Gln Pro Arg Glu Pro Gln Val Tyr Thr Leu Pro Pro
        465                 470                 475                 480

Ser Gln Glu Glu Met Thr Lys Asn Gln Val Ser Leu Thr Cys Leu Val
                            485                 490                 495

Lys Gly Phe Tyr Pro Ser Asp Ile Ala Val Glu Trp Glu Ser Asn Gly
                        500                 505                 510

Gln Pro Glu Asn Asn Tyr Lys Thr Thr Pro Pro Val Leu Asp Ser Asp
                    515                 520                 525

Gly Ser Phe Phe Leu Tyr Ser Arg Leu Thr Val Asp Lys Ser Arg Trp
                530                 535                 540

Gln Glu Gly Asn Val Phe Ser Cys Ser Val Met His Glu Ala Leu His
        545                 550                 555                 560

Asn His Tyr Thr Gln Lys Ser Leu Ser Leu Ser Leu Gly
                            565                 570

<210> SEQ ID NO 71
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 71

Glu Ile Val Leu Thr Gln Ser Pro Ala Thr Leu Ser Leu Ser Pro Gly
        1               5                   10                  15

Glu Arg Ala Thr Leu Ser Cys Arg Ala Ser Gln Ser Val Tyr Ser Tyr
                    20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
        65                  70                  75                  80

Glu Asp Phe Ala Val Tyr Tyr Cys Gln Gln Arg Ser Asn Trp Pro Pro
                        85                  90                  95

Phe Thr Phe Gly Pro Gly Thr Lys Val Asp Ile Lys Gly Gly Gly Ser
                    100                 105                 110

Gly Gly Gly Gly Gln Val Gln Leu Val Gln Ser Gly Ala Glu Val Lys
                115                 120                 125

Lys Pro Gly Ser Ser Val Lys Val Ser Cys Lys Ala Ser Gly Tyr Thr
            130                 135                 140

Phe Thr Asp Gln Thr Ile His Trp Met Arg Gln Ala Pro Gly Gln Gly
        145                 150                 155                 160

Leu Glu Trp Ile Gly Tyr Ile Tyr Pro Arg Asp Asp Ser Pro Lys Tyr
                        165                 170                 175

Asn Glu Asn Phe Lys Gly Lys Val Thr Ile Thr Ala Asp Lys Ser Thr
```

```
                    180                 185                 190
Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
            275                 280                 285

Leu Gln Ser Gly Asn Ser Gln Glu Ser Val Thr Glu Gln Asp Ser Lys
            290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
            325                 330                 335

Ser Ser Pro Val Thr Lys Ser Phe Asn Arg Gly Glu Cys
            340                 345

<210> SEQ ID NO 72
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
            85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
            130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
            165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
```

```
            195                 200                 205
Tyr Tyr Cys Ala Arg Asp Arg Gly Ile Ala Ala Gly Gly Asn Tyr Tyr
210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Cys Ser Arg Ser Thr Ser Glu Ser Thr Ala Ala Leu
                260                 265                 270

Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
        290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
                325                 330                 335

Ser Asn Thr Lys Val Asp Lys Arg Val Glu Ser Lys Tyr Gly Pro Pro
            340                 345                 350

Cys Pro Pro Cys Pro Ala Pro Glu Phe Leu Gly Gly Pro Ser Val Phe
        355                 360                 365

Leu Phe Pro Pro Lys Pro Lys Asp Thr Leu Tyr Ile Thr Arg Glu Pro
370                 375                 380

Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
                405                 410                 415

Lys Pro Arg Glu Glu Gln Phe Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Gly Leu Pro Ser Ser Ile Glu Lys Thr Ile Ser
450                 455                 460

Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Arg Leu Thr Val Asp Lys Ser Arg Trp
530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly
                565                 570

<210> SEQ ID NO 73
<211> LENGTH: 349
<212> TYPE: PRT
<213> ORGANISM: Artificial Sequence
<220> FEATURE:
<223> OTHER INFORMATION: Synthetic Polypeptide
```

<400> SEQUENCE: 73

| | | | | | | | | | | | | | | |
|---|---|---|---|---|---|---|---|---|---|---|---|---|---|---|
|Glu|Ile|Val|Leu|Thr|Gln|Ser|Pro|Ala|Thr|Leu|Ser|Leu|Ser|Pro|Gly|
|1| | | |5| | | |10| | | |15| | |
|Glu|Arg|Ala|Thr|Leu|Ser|Cys|Arg|Ala|Ser|Gln|Ser|Val|Tyr|Ser|Tyr|
| | | |20| | | | |25| | | | |30| | |
|Leu|Ala|Trp|Tyr|Gln|Gln|Lys|Pro|Gly|Gln|Ala|Pro|Arg|Leu|Leu|Ile|
| | | |35| | | | |40| | | | |45| | |
|Tyr|Asp|Ala|Ser|Asn|Arg|Ala|Thr|Gly|Ile|Pro|Ala|Arg|Phe|Ser|Gly|
| |50| | | | |55| | | | |60| | | | |
|Ser|Gly|Ser|Gly|Thr|Asp|Phe|Thr|Leu|Thr|Ile|Ser|Ser|Leu|Glu|Pro|
|65| | | | |70| | | | |75| | | | |80|
|Glu|Asp|Phe|Ala|Val|Tyr|Tyr|Cys|Gln|Gln|Arg|Ser|Asn|Trp|Pro|Pro|
| | | | |85| | | | |90| | | | |95| |
|Phe|Thr|Phe|Gly|Pro|Gly|Thr|Lys|Val|Asp|Ile|Lys|Gly|Gly|Gly|Ser|
| | | |100| | | | |105| | | | |110| | |
|Gly|Gly|Gly|Gly|Gln|Val|Gln|Leu|Val|Gln|Ser|Gly|Ala|Glu|Val|Lys|
| | |115| | | | |120| | | | |125| | | |
|Lys|Pro|Gly|Ser|Ser|Val|Lys|Val|Ser|Cys|Lys|Ala|Ser|Gly|Tyr|Thr|
| |130| | | | |135| | | | |140| | | | |
|Phe|Thr|Asp|Gln|Thr|Ile|His|Trp|Met|Arg|Gln|Ala|Pro|Gly|Gln|Gly|
|145| | | | |150| | | | |155| | | | |160|
|Leu|Glu|Trp|Ile|Gly|Tyr|Ile|Tyr|Pro|Arg|Asp|Asp|Ser|Pro|Lys|Tyr|
| | | | |165| | | | |170| | | | |175| |
|Asn|Glu|Asn|Phe|Lys|Gly|Lys|Val|Thr|Ile|Thr|Ala|Asp|Lys|Ser|Thr|
| | | |180| | | | |185| | | | |190| | |
|Ser|Thr|Ala|Tyr|Met|Glu|Leu|Ser|Ser|Leu|Arg|Ser|Glu|Asp|Thr|Ala|
| | |195| | | | |200| | | | |205| | | |
|Val|Tyr|Tyr|Cys|Ala|Ile|Pro|Asp|Arg|Ser|Gly|Tyr|Ala|Trp|Phe|Ile|
| |210| | | | |215| | | | |220| | | | |
|Tyr|Trp|Gly|Gln|Gly|Thr|Leu|Val|Thr|Val|Ser|Ser|Leu|Gly|Gly|Gly|
|225| | | | |230| | | | |235| | | | |240|
|Ser|Gly|Arg|Thr|Val|Ala|Ala|Pro|Ser|Val|Phe|Ile|Phe|Pro|Pro|Ser|
| | | |245| | | | |250| | | | |255| | |
|Asp|Glu|Gln|Leu|Lys|Ser|Gly|Thr|Ala|Ser|Val|Val|Cys|Leu|Leu|Asn|
| | | |260| | | | |265| | | | |270| | |
|Asn|Phe|Tyr|Pro|Arg|Glu|Ala|Lys|Val|Gln|Trp|Lys|Val|Asp|Asn|Ala|
| | |275| | | | |280| | | | |285| | | |
|Leu|Gln|Ser|Gly|Asn|Ser|Gln|Glu|Ser|Val|Thr|Glu|Gln|Asp|Ser|Lys|
| |290| | | | |295| | | | |300| | | | |
|Asp|Ser|Thr|Tyr|Ser|Leu|Ser|Ser|Thr|Leu|Thr|Leu|Ser|Lys|Ala|Asp|
|305| | | | |310| | | | |315| | | | |320|
|Tyr|Glu|Lys|His|Lys|Val|Tyr|Ala|Cys|Glu|Val|Thr|His|Gln|Gly|Leu|
| | | | |325| | | | |330| | | | |335| |
|Ser|Ser|Pro|Val|Thr|Lys|Ser|Phe|Asn|Arg|Gly|Glu|Cys| | | |
| | | |340| | | | |345| | | | | | | |

<210> SEQ ID NO 74
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 74

Asp Ile Gln Met Thr Gln Ser Pro Ser Ser Leu Ser Ala Ser Val Gly

-continued

```
  1               5                   10                  15
Asp Arg Val Thr Ile Thr Cys Lys Ala Ser Arg Asp Val Ala Ile Ala
             20                  25                  30

Val Ala Trp Tyr Gln Gln Lys Pro Gly Lys Val Pro Lys Leu Leu Ile
             35                  40                  45

Tyr Trp Ala Ser Thr Arg His Thr Gly Val Pro Ser Arg Phe Ser Gly
             50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                     85                  90                  95

Thr Phe Gly Ser Gly Thr Lys Leu Glu Ile Lys Gly Gly Gly Ser Gly
                    100                 105                 110

Gly Gly Gly Gln Val Gln Leu Val Glu Ser Gly Gly Gly Val Val Gln
                115                 120                 125

Pro Gly Arg Ser Leu Arg Leu Ser Cys Ala Ala Ser Gly Phe Ile Phe
            130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                    165                 170                 175

Asp Ser Val Lys Gly Arg Phe Thr Ile Ser Arg Asp Asn Ser Lys Asn
                180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Gly Asn Tyr Tyr
210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                    245                 250                 255

Pro Leu Ala Pro Ser Ser Lys Ser Thr Ser Gly Gly Thr Ala Ala Leu
                260                 265                 270

Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
            290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                    325                 330                 335

Ser Asn Thr Lys Val Asp Lys Arg Val Glu Pro Lys Ser Cys Asp Lys
                340                 345                 350

Thr His Thr Cys Pro Pro Cys Pro Ala Pro Glu Leu Leu Gly Gly Pro
            355                 360                 365

Ser Val Phe Leu Phe Pro Pro Lys Pro Lys Asp Thr Leu Met Ile Ser
            370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                    405                 410                 415

Ala Lys Thr Lys Pro Arg Glu Glu Gln Tyr Asn Ser Thr Tyr Arg Val
                420                 425                 430
```

```
Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

<210> SEQ ID NO 75
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220
```

```
Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
        260                 265                 270

Asn Phe Tyr Pro Arg Glu Ala Lys Val Gln Trp Lys Val Asp Asn Ala
    275                 280                 285

Leu Gln Ser Gly Asn Ser Gln Glu Ser Val Thr Glu Gln Asp Ser Lys
        290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 76
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
            85                  90                  95

Thr Phe Gly Ser Gly Thr Lys Leu Glu Ile Lys Gly Gly Gly Ser Gly
        100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240
```

```
Ser Phe Asn Arg Gly Glu Ser Ala Ser Thr Lys Gly Pro Ser Val Phe
            245                 250                 255

Pro Leu Ala Pro Cys Ser Arg Ser Thr Ser Glu Ser Thr Ala Ala Leu
            260                 265                 270

Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
            290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
            325                 330                 335

Ser Asn Thr Lys Val Asp Lys Arg Val Glu Ser Lys Tyr Gly Pro Pro
            340                 345                 350

Cys Pro Pro Cys Pro Ala Pro Glu Phe Leu Gly Gly Pro Ser Val Phe
            355                 360                 365

Leu Phe Pro Pro Lys Pro Lys Asp Thr Leu Met Ile Ser Arg Thr Pro
            370                 375                 380

Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
            405                 410                 415

Lys Pro Arg Glu Glu Gln Phe Asn Ser Thr Tyr Arg Val Val Ser Val
            420                 425                 430

Leu Thr Val Leu His Gln Asp Trp Leu Asn Gly Lys Glu Tyr Lys Cys
            435                 440                 445

Lys Val Ser Asn Lys Gly Leu Pro Ser Ser Ile Glu Lys Thr Ile Ser
            450                 455                 460

Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Leu Tyr Ser Arg Leu Thr Val Asp Lys Ser Arg Trp
            530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly
            565                 570

<210> SEQ ID NO 77
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30
```

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 78
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                245                 250                 255

Pro Leu Ala Pro Cys Ser Arg Ser Thr Ser Glu Ser Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
                325                 330                 335

Ser Asn Thr Lys Val Asp Lys Arg Val Glu Ser Lys Tyr Gly Pro Pro
            340                 345                 350

Cys Pro Pro Cys Pro Ala Pro Glu Phe Leu Gly Gly Pro Ser Val Phe
        355                 360                 365

Leu Phe Pro Pro Lys Pro Lys Asp Thr Leu Tyr Ile Thr Arg Glu Pro
    370                 375                 380

Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
                405                 410                 415

Lys Pro Arg Glu Glu Gln Phe Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Gly Leu Pro Ser Ser Ile Glu Lys Thr Ile Ser
    450                 455                 460

-continued

```
Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Arg Leu Thr Val Asp Lys Ser Arg Trp
    530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly
                565                 570

<210> SEQ ID NO 79
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 79

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255
```

Asp Glu Gln Leu Lys Ser Gly Thr Ala Ser Val Val Cys Leu Leu Asn
                260                 265                 270

Asn Phe Tyr Pro Arg Glu Ala Lys Val Gln Trp Lys Val Asp Asn Ala
                275                 280                 285

Leu Gln Ser Gly Asn Ser Gln Glu Ser Val Thr Glu Gln Asp Ser Lys
        290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
                340                 345

<210> SEQ ID NO 80
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 80

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
                100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
                180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
                260                 265                 270

```
Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 81
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60
```

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 82
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 82

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

Glu Asp Phe Ala Val Tyr Tyr Cys Gln Gln Arg Ser Asn Trp Pro Pro
65                  70                  75                  80

Phe Thr Phe Gly Pro Gly Thr Lys Val Asp Ile Lys Gly Gly Gly Ser
            85                  90                  95

Gly Gly Gly Gly Gln Val Gln Leu Val Gln Ser Gly Ala Glu Val Lys
        100                 105                 110

Lys Pro Gly Ser Ser Val Lys Val Ser Cys Lys Ala Ser Gly Tyr Thr
    115                 120                 125

Phe Thr Asp Gln Thr Ile His Trp Met Arg Gln Ala Pro Gly Gln Gly
130                 135                 140

Leu Glu Trp Ile Gly Tyr Ile Tyr Pro Arg Asp Asp Ser Pro Lys Tyr
145                 150                 155                 160

Asn Glu Asn Phe Lys Gly Lys Val Thr Ile Thr Ala Asp Lys Ser Thr
            165                 170                 175

Ser Thr Ala Tyr Met Glu Leu Ser Ser Leu Arg Ser Glu Asp Thr Ala
        180                 185                 190

Val Tyr Tyr Cys Ala Ile Pro Asp Arg Ser Gly Tyr Ala Trp Phe Ile
    195                 200                 205

Tyr Trp Gly Gln Gly Thr Leu Val Thr Val Ser Ser Leu Gly Gly Gly
210                 215                 220

Ser Gly Ala Ser Thr Lys Gly Pro Ser Val Phe Pro Leu Ala Pro Ser
225                 230                 235                 240

Ser Lys Ser Thr Ser Gly Gly Thr Ala Ala Leu Gly Cys Leu Val Lys
            245                 250                 255

Asp Tyr Phe Pro Glu Pro Val Thr Val Ser Trp Asn Ser Gly Ala Leu
        260                 265                 270

Thr Ser Gly Val His Thr Phe Pro Ala Val Leu Gln Ser Ser Gly Leu
    275                 280                 285

Tyr Ser Leu Ser Ser Val Val Thr Val Pro Ser Ser Ser Leu Gly Thr
290                 295                 300

Gln Thr Tyr Ile Cys Asn Val Asn His Lys Pro Ser Asn Thr Lys Val
305                 310                 315                 320

Asp Lys Arg Val Glu Pro Lys Ser Cys Asp Lys Thr His Thr Cys Pro
            325                 330                 335

Pro Cys Pro Ala Pro Glu Leu Leu Gly Gly Pro Ser Val Phe Leu Phe
        340                 345                 350

Pro Pro Lys Pro Lys Asp Thr Leu Met Ile Ser Arg Thr Pro Glu Val
    355                 360                 365

Thr Cys Val Val Val Asp Val Ser His Glu Asp Pro Glu Val Lys Phe
370                 375                 380

Asn Trp Tyr Val Asp Gly Val Glu Val His Asn Ala Lys Thr Lys Pro
385                 390                 395                 400

Arg Glu Glu Gln Tyr Asn Ser Thr Tyr Arg Val Val Ser Val Leu Thr
            405                 410                 415

Val Leu His Gln Asp Trp Leu Asn Gly Lys Glu Tyr Lys Cys Lys Val
        420                 425                 430

Ser Asn Lys Ala Leu Pro Ala Pro Ile Glu Lys Thr Ile Ser Lys Ala
    435                 440                 445

Lys Gly Gln Pro Arg Glu Pro Gln Val Tyr Thr Leu Pro Pro Ser Arg
450                 455                 460

Glu Glu Met Thr Lys Asn Gln Val Ser Leu Thr Cys Leu Val Lys Gly
465                 470                 475                 480

485                 490                 495

```
Phe Tyr Pro Ser Asp Ile Ala Val Glu Trp Glu Ser Asn Gly Gln Pro
            500                 505                 510

Glu Asn Asn Tyr Lys Thr Thr Pro Val Leu Asp Ser Asp Gly Ser
        515                 520                 525

Phe Phe Leu Tyr Ser Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 83
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285
```

```
Lys Val Asp Asn Ala Leu Gln Ser Gly Asn Ser Gln Glu Ser Val Thr
            290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 84
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 84

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285
```

Thr Ser Gly Val His Thr Phe Pro Ala Val Leu Gln Ser Ser Gly Leu
290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Cys Pro
            340                 345                 350

Ala Pro Glu Phe Leu Gly Gly Pro Ser Val Phe Leu Phe Pro Pro Lys
                355                 360                 365

Pro Lys Asp Thr Leu Met Ile Ser Arg Thr Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
                420                 425                 430

Gln Asp Trp Leu Asn Gly Lys Glu Tyr Lys Cys Lys Val Ser Asn Lys
            435                 440                 445

Gly Leu Pro Ser Ser Ile Glu Lys Thr Ile Ser Lys Ala Lys Gly Gln
450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
            515                 520                 525

Tyr Ser Arg Leu Thr Val Asp Lys Ser Arg Trp Gln Glu Gly Asn Val
            530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 85
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

-continued

```
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Gly Ser Gly
            100                 105                 110
Gly Gly Gly Gln Val Gln Leu Val Glu Ser Gly Gly Val Val Gln
        115                 120                 125
Pro Gly Arg Ser Leu Arg Leu Ser Cys Ala Ala Ser Gly Phe Ile Phe
    130                 135                 140
Ser Ser Tyr Ala Met His Trp Val Arg Gln Ala Pro Gly Asp Gly Leu
145                 150                 155                 160
Glu Trp Val Ala Phe Met Ser Tyr Asp Gly Ser Asn Lys Lys Tyr Ala
                165                 170                 175
Asp Ser Val Lys Gly Arg Phe Thr Ile Ser Arg Asp Asn Ser Lys Asn
            180                 185                 190
Thr Leu Tyr Leu Gln Met Asn Ser Leu Arg Ala Glu Asp Thr Ala Val
        195                 200                 205
Tyr Tyr Cys Ala Arg Asp Arg Gly Ile Ala Ala Gly Asn Tyr Tyr
    210                 215                 220
Tyr Tyr Gly Met Asp Val Trp Gly Gln Gly Thr Thr Val Thr Val Ser
225                 230                 235                 240
Ser Leu Gly Gly Gly Ser Gly Arg Thr Val Ala Ala Pro Ser Val Phe
                245                 250                 255
Ile Phe Pro Pro Ser Asp Glu Gln Leu Lys Ser Gly Thr Ala Ser Val
            260                 265                 270
Val Cys Leu Leu Asn Asn Phe Tyr Pro Arg Glu Ala Lys Val Gln Trp
        275                 280                 285
Lys Val Asp Asn Ala Leu Gln Ser Gly Asn Ser Gln Glu Ser Val Thr
    290                 295                 300
Glu Gln Asp Ser Lys Asp Ser Thr Tyr Ser Leu Ser Ser Thr Leu Thr
305                 310                 315                 320
Leu Ser Lys Ala Asp Tyr Glu Lys His Lys Val Tyr Ala Cys Glu Val
                325                 330                 335
Thr His Gln Gly Leu Ser Ser Pro Val Thr Lys Ser Phe Asn Arg Gly
            340                 345                 350
Glu Cys

<210> SEQ ID NO 86
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 86

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Tyr Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
```

```
                   85                  90                  95
Phe Thr Phe Gly Pro Gly Thr Lys Val Asp Ile Lys Gly Gly Ser
           100                 105                 110

Gly Gly Gly Gly Gln Val Gln Leu Val Gln Ser Gly Ala Glu Val Lys
           115                 120                 125

Lys Pro Gly Ser Ser Val Lys Val Ser Cys Lys Ala Ser Gly Tyr Thr
           130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
                180                 185                 190

Ser Thr Ala Tyr Met Glu Leu Ser Ser Leu Arg Ser Glu Asp Thr Ala
                195                 200                 205

Val Tyr Tyr Cys Ala Ile Pro Asp Arg Ser Gly Tyr Ala Trp Phe Ile
            210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
            355                 360                 365

Pro Lys Asp Thr Leu Tyr Ile Thr Arg Glu Pro Glu Val Thr Cys Val
    370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
            435                 440                 445

Gly Leu Pro Ser Ser Ile Glu Lys Thr Ile Ser Lys Ala Lys Gly Gln
    450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
                500                 505                 510
```

```
Tyr Lys Thr Thr Pro Pro Val Leu Asp Ser Asp Gly Ser Phe Phe Leu
            515                 520                 525

Tyr Ser Arg Leu Thr Val Asp Lys Ser Arg Trp Gln Glu Gly Asn Val
        530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 87
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300
```

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
            325                 330                 335

Thr His Gln Gly Leu Ser Ser Pro Val Thr Lys Ser Phe Asn Arg Gly
        340                 345                 350

Glu Cys

<210> SEQ ID NO 88
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
        290                 295                 300

Tyr Ser Leu Ser Ser Val Val Thr Val Pro Ser Ser Leu Gly Thr
305                 310                 315                 320

Gln Thr Tyr Ile Cys Asn Val Asn His Lys Pro Ser Asn Thr Lys Val
            325                 330                 335

Asp Lys Arg Val Glu Pro Lys Ser Cys Asp Lys Thr His Thr Cys Pro
        340                 345                 350

Pro Cys Pro Ala Pro Glu Ala Ala Gly Gly Pro Ser Val Phe Leu Phe
    355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 89
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Ser Gly
            100                 105                 110

Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
            130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Gly Asn Tyr Tyr
            210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
            290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 90
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser

```
                100                 105                 110
Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Ser Pro Lys Tyr
            165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
            210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
            245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
            290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
            325                 330                 335

Asp Lys Arg Val Glu Pro Lys Ser Cys Asp Lys Thr His Thr Cys Pro
            340                 345                 350

Pro Cys Pro Ala Pro Glu Leu Leu Gly Gly Pro Ser Val Phe Leu Phe
            355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
            405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
            435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
            485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
            515                 520                 525
```

```
Phe Phe Leu Tyr Ser Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570
```

<210> SEQ ID NO 91
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320
```

Leu Ser Lys Ala Asp Tyr Glu Lys His Lys Val Tyr Ala Cys Glu Val
            325                 330                 335

Thr His Gln Gly Leu Ser Ser Pro Val Thr Lys Ser Phe Asn Arg Gly
            340                 345                 350

Glu Cys

<210> SEQ ID NO 92
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
            165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Cys
            245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
            290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                    325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
            355                 360                 365

Pro Lys Asp Thr Leu Met Ile Ser Arg Thr Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
            405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
            435                 440                 445

Gly Leu Pro Ser Ser Ile Glu Lys Thr Ile Ser Lys Ala Lys Gly Gln
            450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
            485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
            515                 520                 525

Tyr Ser Arg Leu Thr Val Asp Lys Ser Arg Trp Gln Glu Gly Asn Val
530                 535                 540

Phe Ser Cys Ser Val Met His Glu Ala Leu His Asn His Tyr Thr Gln
545                 550                 555                 560

Lys Ser Leu Ser Leu Ser Leu Gly
            565

<210> SEQ ID NO 93
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

```
Gly Gly Gly Gln Val Gln Leu Val Glu Ser Gly Gly Val Val Gln
            115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                    165                 170                 175

Asp Ser Val Lys Gly Arg Phe Thr Ile Ser Arg Asp Asn Ser Lys Asn
                180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Gly Asn Tyr Tyr
210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                    245                 250                 255

Ile Phe Pro Pro Ser Asp Glu Gln Leu Lys Ser Gly Thr Ala Ser Val
                260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                    325                 330                 335

Thr His Gln Gly Leu Ser Ser Pro Val Thr Lys Ser Phe Asn Arg Gly
                340                 345                 350

Glu Cys

<210> SEQ ID NO 94
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                    85                  90                  95

Phe Thr Phe Gly Pro Gly Thr Lys Val Asp Ile Lys Gly Gly Gly Ser
                100                 105                 110

Gly Gly Gly Gly Gln Val Gln Leu Val Gln Ser Gly Ala Glu Val Lys
```

-continued

```
            115                 120                 125
Lys Pro Gly Ser Ser Val Lys Val Ser Cys Lys Ala Ser Gly Tyr Thr
            130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Ser Pro Lys Tyr
                    165                 170                 175

Asn Glu Asn Phe Lys Gly Lys Val Thr Ile Thr Ala Asp Lys Ser Thr
                180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
            210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
            290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
            355                 360                 365

Pro Lys Asp Thr Leu Tyr Ile Thr Arg Glu Pro Glu Val Thr Cys Val
            370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
                420                 425                 430

Gln Asp Trp Leu Asn Gly Lys Glu Tyr Lys Cys Lys Val Ser Asn Lys
            435                 440                 445

Gly Leu Pro Ser Ser Ile Glu Lys Thr Ile Ser Lys Ala Lys Gly Gln
            450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
            515                 520                 525

Tyr Ser Arg Leu Thr Val Asp Lys Ser Arg Trp Gln Glu Gly Asn Val
530                 535                 540
```

Phe Ser Cys Ser Val Met His Glu Ala Leu His Asn His Tyr Thr Gln
545                 550                 555                 560

Lys Ser Leu Ser Leu Ser Leu Gly
            565

<210> SEQ ID NO 95
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Val Glu Pro Lys Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

```
Thr His Gln Gly Leu Ser Ser Pro Val Thr Lys Ser Phe Asn Arg Gly
            340                 345                 350

Glu Cys

<210> SEQ ID NO 96
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Val Val Thr Val Pro Ser
305                 310                 315                 320

Ser Ser Leu Gly Thr Gln Thr Tyr Ile Cys Asn Val Asn His Lys Pro
                325                 330                 335
```

Ser Asn Thr Lys Val Asp Lys Arg Val Glu Pro Lys Ser Cys Asp Lys
                340                 345                 350

Thr His Thr Cys Pro Pro Cys Pro Ala Pro Glu Ala Ala Gly Gly Pro
        355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
        420                 425                 430

Val Ser Val Leu Thr Val Leu His Gln Asp Trp Leu Asn Gly Lys Glu
    435                 440                 445

Tyr Lys Cys Lys Val Ser Asn Lys Ala Leu Pro Ala Pro Ile Glu Lys
        450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
        500                 505                 510

Ser Asn Gly Gln Pro Glu Asn Asn Tyr Lys Thr Thr Pro Pro Val Leu
    515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

<210> SEQ ID NO 97
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 98
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
130                 135                 140

```
Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
                180                 185                 190

Thr Leu Tyr Leu Gln Met Asn Ser Leu Arg Ala Glu Asp Thr Ala Val
            195                 200                 205

Tyr Tyr Cys Ala Arg Asp Arg Gly Ile Ala Ala Gly Asn Tyr Tyr
        210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
```

<210> SEQ ID NO 99
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 99

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

-continued

```
<210> SEQ ID NO 100
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
            130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Ala Ser Thr Lys Gly Pro Ser Val Phe
                245                 250                 255

Pro Leu Ala Pro Cys Ser Arg Ser Thr Ser Glu Ser Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
                325                 330                 335

Ser Asn Thr Lys Val Asp Lys Arg Val Glu Ser Lys Tyr Gly Pro Pro
            340                 345                 350

Cys Pro Pro Cys Pro Ala Pro Glu Phe Leu Gly Gly Pro Ser Val Phe
        355                 360                 365

Leu Phe Pro Pro Lys Pro Lys Asp Thr Leu Met Ile Ser Arg Thr Pro
```

```
             370                 375                 380
Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
                405                 410                 415

Lys Pro Arg Glu Gln Phe Asn Ser Thr Tyr Arg Val Val Ser Val
            420                 425                 430

Leu Thr Val Leu His Gln Asp Trp Leu Asn Gly Lys Glu Tyr Lys Cys
                435                 440                 445

Lys Val Ser Asn Lys Gly Leu Pro Ser Ser Ile Glu Lys Thr Ile Ser
            450                 455                 460

Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Leu Tyr Ser Arg Leu Thr Val Asp Lys Ser Arg Trp
            530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly
                565                 570

<210> SEQ ID NO 101
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
```

```
                          165                 170                 175
Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
                260                 265                 270

Asn Phe Tyr Pro Arg Glu Ala Lys Val Gln Trp Lys Val Asp Asn Ala
                275                 280                 285

Leu Gln Ser Gly Asn Ser Gln Glu Ser Val Thr Glu Gln Asp Ser Lys
            290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 102
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
```

```
            180                 185                 190
Thr Leu Tyr Leu Gln Met Asn Ser Leu Arg Ala Glu Asp Thr Ala Val
            195                 200                 205
Tyr Tyr Cys Ala Arg Asp Arg Gly Ile Ala Ala Gly Gly Asn Tyr Tyr
            210                 215                 220
Tyr Tyr Gly Met Asp Val Trp Gly Gln Gly Thr Thr Val Thr Val Ser
225                 230                 235                 240
Ser Leu Gly Gly Gly Ser Gly Ala Ser Thr Lys Gly Pro Ser Val Phe
                245                 250                 255
Pro Leu Ala Pro Cys Ser Arg Ser Thr Ser Glu Ser Thr Ala Ala Leu
                260                 265                 270
Gly Cys Leu Val Lys Asp Tyr Phe Pro Glu Pro Val Thr Val Ser Trp
            275                 280                 285
Asn Ser Gly Ala Leu Thr Ser Gly Val His Thr Phe Pro Ala Val Leu
            290                 295                 300
Gln Ser Ser Gly Leu Tyr Ser Leu Ser Ser Val Val Thr Val Pro Ser
305                 310                 315                 320
Ser Ser Leu Gly Thr Lys Thr Tyr Thr Cys Asn Val Asp His Lys Pro
                325                 330                 335
Ser Asn Thr Lys Val Asp Lys Arg Val Glu Ser Lys Tyr Gly Pro Pro
                340                 345                 350
Cys Pro Pro Cys Pro Ala Pro Glu Phe Leu Gly Gly Pro Ser Val Phe
            355                 360                 365
Leu Phe Pro Pro Lys Pro Lys Asp Thr Leu Tyr Ile Thr Arg Glu Pro
            370                 375                 380
Glu Val Thr Cys Val Val Val Asp Val Ser Gln Glu Asp Pro Glu Val
385                 390                 395                 400
Gln Phe Asn Trp Tyr Val Asp Gly Val Glu Val His Asn Ala Lys Thr
                405                 410                 415
Lys Pro Arg Glu Glu Gln Phe Asn Ser Thr Tyr Arg Val Val Ser Val
                420                 425                 430
Leu Thr Val Leu His Gln Asp Trp Leu Asn Gly Lys Glu Tyr Lys Cys
            435                 440                 445
Lys Val Ser Asn Lys Gly Leu Pro Ser Ser Ile Glu Lys Thr Ile Ser
            450                 455                 460
Lys Ala Lys Gly Gln Pro Arg Glu Pro Gln Val Tyr Thr Leu Pro Pro
465                 470                 475                 480
Ser Gln Glu Glu Met Thr Lys Asn Gln Val Ser Leu Thr Cys Leu Val
                485                 490                 495
Lys Gly Phe Tyr Pro Ser Asp Ile Ala Val Glu Trp Glu Ser Asn Gly
                500                 505                 510
Gln Pro Glu Asn Asn Tyr Lys Thr Thr Pro Pro Val Leu Asp Ser Asp
            515                 520                 525
Gly Ser Phe Phe Leu Tyr Ser Arg Leu Thr Val Asp Lys Ser Arg Trp
            530                 535                 540
Gln Glu Gly Asn Val Phe Ser Cys Ser Val Met His Glu Ala Leu His
545                 550                 555                 560
Asn His Tyr Thr Gln Lys Ser Leu Ser Leu Ser Leu Gly
                565                 570

<210> SEQ ID NO 103
<211> LENGTH: 349
<212> TYPE: PRT
<213> ORGANISM: Artificial Sequence
```

<220> FEATURE:
<223> OTHER INFORMATION: Synthetic Polypeptide

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 104
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 104

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Gly Ser Gly
            100                 105                 110
Gly Gly Gly Gln Val Gln Leu Val Glu Ser Gly Gly Val Val Gln
        115                 120                 125
Pro Gly Arg Ser Leu Arg Leu Ser Cys Ala Ala Ser Gly Phe Ile Phe
    130                 135                 140
Ser Ser Tyr Ala Met His Trp Val Arg Gln Ala Pro Gly Asp Gly Leu
145                 150                 155                 160
Glu Trp Val Ala Phe Met Ser Tyr Asp Gly Ser Asn Lys Lys Tyr Ala
                165                 170                 175
Asp Ser Val Lys Gly Arg Phe Thr Ile Ser Arg Asp Asn Ser Lys Asn
            180                 185                 190
Thr Leu Tyr Leu Gln Met Asn Ser Leu Arg Ala Glu Asp Thr Ala Val
        195                 200                 205
Tyr Tyr Cys Ala Arg Asp Arg Gly Ile Ala Ala Gly Asn Tyr Tyr
    210                 215                 220
Tyr Tyr Gly Met Asp Val Trp Gly Gln Gly Thr Thr Val Thr Val Ser
225                 230                 235                 240
Ser Phe Asn Arg Gly Glu Ser Ala Ser Thr Lys Gly Pro Ser Val Phe
                245                 250                 255
Pro Leu Ala Pro Ser Ser Lys Ser Thr Ser Gly Gly Thr Ala Ala Leu
            260                 265                 270
Gly Cys Leu Val Lys Asp Tyr Phe Pro Glu Pro Val Thr Val Ser Trp
        275                 280                 285
Asn Ser Gly Ala Leu Thr Ser Gly Val His Thr Phe Pro Ala Val Leu
290                 295                 300
Gln Ser Ser Gly Leu Tyr Ser Leu Ser Ser Val Val Thr Val Pro Ser
305                 310                 315                 320
Ser Ser Leu Gly Thr Gln Thr Tyr Ile Cys Asn Val Asn His Lys Pro
                325                 330                 335
Ser Asn Thr Lys Val Asp Lys Arg Val Glu Pro Lys Ser Cys Asp Lys
            340                 345                 350
Thr His Thr Cys Pro Pro Cys Pro Ala Pro Glu Ala Ala Gly Gly Pro
        355                 360                 365
Ser Val Phe Leu Phe Pro Pro Lys Pro Lys Asp Thr Leu Met Ile Ser
    370                 375                 380
Arg Thr Pro Glu Val Thr Cys Val Val Val Asp Val Ser His Glu Asp
385                 390                 395                 400
Pro Glu Val Lys Phe Asn Trp Tyr Val Asp Gly Val Glu Val His Asn
                405                 410                 415
```

Ala Lys Thr Lys Pro Arg Glu Glu Gln Tyr Asn Ser Thr Tyr Arg Val
                420                 425                 430

Val Ser Val Leu Thr Val Leu His Gln Asp Trp Leu Asn Gly Lys Glu
            435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

<210> SEQ ID NO 105
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

```
Val Tyr Tyr Cys Ala Ile Pro Asp Arg Ser Gly Tyr Ala Trp Phe Ile
        210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 106
<211> LENGTH: 576
<212> TYPE: PRT
<213> ORGANISM: Artificial Sequence
<220> FEATURE:
<223> OTHER INFORMATION: Synthetic Polypeptide

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220
```

Tyr Tyr Gly Met Asp Val Trp Gly Gln Gly Thr Val Thr Val Ser
225                 230                 235                 240

Ser Phe Asn Arg Gly Glu Ser Ala Ser Thr Lys Gly Pro Ser Val Phe
            245                 250                 255

Pro Leu Ala Pro Ser Ser Lys Ser Thr Ser Gly Gly Thr Ala Ala Leu
        260                 265                 270

Gly Cys Leu Val Lys Asp Tyr Phe Pro Glu Pro Val Thr Val Ser Trp
    275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
            325                 330                 335

Ser Asn Thr Lys Val Asp Lys Arg Val Glu Pro Lys Ser Cys Asp Lys
        340                 345                 350

Thr His Thr Cys Pro Pro Cys Pro Ala Pro Glu Leu Leu Gly Gly Pro
    355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
            405                 410                 415

Ala Lys Thr Lys Pro Arg Glu Glu Gln Tyr Asn Ser Thr Tyr Arg Val
        420                 425                 430

Val Ser Val Leu Thr Val Leu His Gln Asp Trp Leu Asn Gly Lys Glu
    435                 440                 445

Tyr Lys Cys Lys Val Ser Asn Lys Ala Leu Pro Ala Pro Ile Glu Lys
450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
            485                 490                 495

Cys Leu Val Lys Gly Phe Tyr Pro Ser Asp Ile Ala Val Glu Trp Glu
        500                 505                 510

Ser Asn Gly Gln Pro Glu Asn Asn Tyr Lys Thr Thr Pro Pro Val Leu
    515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
            565                 570                 575

<210> SEQ ID NO 107
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 107

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 108
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30
```

Val Ala Trp Tyr Gln Gln Lys Pro Gly Lys Val Pro Lys Leu Leu Ile
          35                  40                  45

Tyr Trp Ala Ser Thr Arg His Thr Gly Val Pro Ser Arg Phe Ser Gly
     50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                 85                  90                  95

Thr Phe Gly Ser Gly Thr Lys Leu Glu Ile Lys Gly Gly Gly Ser Gly
             100                 105                 110

Gly Gly Gly Gln Val Gln Leu Val Glu Ser Gly Gly Gly Val Val Gln
         115                 120                 125

Pro Gly Arg Ser Leu Arg Leu Ser Cys Ala Ala Ser Gly Phe Ile Phe
     130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                 165                 170                 175

Asp Ser Val Lys Gly Arg Phe Thr Ile Ser Arg Asp Asn Ser Lys Asn
             180                 185                 190

Thr Leu Tyr Leu Gln Met Asn Ser Leu Arg Ala Glu Asp Thr Ala Val
         195                 200                 205

Tyr Tyr Cys Ala Arg Asp Arg Gly Ile Ala Ala Gly Gly Asn Tyr Tyr
     210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                 245                 250                 255

Pro Leu Ala Pro Cys Ser Arg Ser Thr Ser Glu Ser Thr Ala Ala Leu
             260                 265                 270

Gly Cys Leu Val Lys Asp Tyr Phe Pro Glu Pro Val Thr Val Ser Trp
         275                 280                 285

Asn Ser Gly Ala Leu Thr Ser Gly Val His Thr Phe Pro Ala Val Leu
     290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
                 325                 330                 335

Ser Asn Thr Lys Val Asp Lys Arg Val Glu Ser Lys Tyr Gly Pro Pro
             340                 345                 350

Cys Pro Pro Cys Pro Ala Pro Glu Phe Leu Gly Gly Pro Ser Val Phe
         355                 360                 365

Leu Phe Pro Pro Lys Pro Lys Asp Thr Leu Met Ile Ser Arg Thr Pro
     370                 375                 380

Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
                 405                 410                 415

Lys Pro Arg Glu Glu Gln Phe Asn Ser Thr Tyr Arg Val Val Ser Val
             420                 425                 430

Leu Thr Val Leu His Gln Asp Trp Leu Asn Gly Lys Glu Tyr Lys Cys
         435                 440                 445

```
Lys Val Ser Asn Lys Gly Leu Pro Ser Ser Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
                515                 520                 525

Gly Ser Phe Phe Leu Tyr Ser Arg Leu Thr Val Asp Lys Ser Arg Trp
530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly
                565                 570

<210> SEQ ID NO 109
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Val Glu Pro Lys
225                 230                 235                 240
```

```
Ser Ser Arg Thr Val Ala Ala Pro Ser Val Phe Ile Phe Pro Pro Ser
            245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
            275                 280                 285

Leu Gln Ser Gly Asn Ser Gln Glu Ser Val Thr Glu Gln Asp Ser Lys
            290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
                340                 345

<210> SEQ ID NO 110
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Gly Val Val Gln
        115                 120                 125

Pro Gly Arg Ser Leu Arg Leu Ser Cys Ala Ala Ser Gly Phe Ile Phe
130                 135                 140

Ser Ser Tyr Ala Met His Trp Val Arg Gln Ala Pro Gly Asp Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Asn Tyr Tyr
    210                 215                 220

Tyr Tyr Gly Met Asp Val Trp Gly Gln Gly Thr Thr Val Thr Val Ser
225                 230                 235                 240

Ser Phe Asn Arg Gly Glu Ser Ala Ser Thr Lys Gly Pro Ser Val Phe
                245                 250                 255
```

```
Pro Leu Ala Pro Cys Ser Arg Ser Thr Ser Glu Ser Thr Ala Ala Leu
            260                 265                 270

Gly Cys Leu Val Lys Asp Tyr Phe Pro Glu Pro Val Thr Val Ser Trp
        275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
                325                 330                 335

Ser Asn Thr Lys Val Asp Lys Arg Val Glu Ser Lys Tyr Gly Pro Pro
            340                 345                 350

Cys Pro Pro Cys Pro Ala Pro Glu Phe Leu Gly Gly Pro Ser Val Phe
        355                 360                 365

Leu Phe Pro Pro Lys Pro Lys Asp Thr Leu Tyr Ile Thr Arg Glu Pro
    370                 375                 380

Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
                405                 410                 415

Lys Pro Arg Glu Glu Gln Phe Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Gly Leu Pro Ser Ser Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Gln Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Arg Leu Thr Val Asp Lys Ser Arg Trp
    530                 535                 540

Gln Glu Gly Asn Val Phe Ser Cys Ser Val Met His Glu Ala Leu His
545                 550                 555                 560

Asn His Tyr Thr Gln Lys Ser Leu Ser Leu Ser Leu Gly
                565                 570

<210> SEQ ID NO 111
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 111

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 112
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 112

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Tyr Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
```

```
                        485                 490                 495
Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 113
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Ser Cys Ala Ala Ser Gly Phe Ile Phe
    130                 135                 140

Ser Ser Tyr Ala Met His Trp Val Arg Gln Ala Pro Gly Asn Gly Leu
145                 150                 155                 160

Glu Trp Val Ala Phe Met Ser Tyr Asp Gly Ser Asn Lys Lys Tyr Ala
                165                 170                 175

Asp Ser Val Lys Gly Arg Phe Thr Ile Ser Arg Asp Asn Ser Lys Asn
            180                 185                 190

Thr Leu Tyr Leu Gln Met Asn Ser Leu Arg Ala Glu Asp Thr Ala Val
        195                 200                 205

Tyr Tyr Cys Ala Arg Asp Arg Gly Ile Ala Ala Gly Gly Asn Tyr Tyr
    210                 215                 220

Tyr Tyr Gly Met Asp Val Trp Gly Gln Gly Thr Thr Val Thr Val Ser
225                 230                 235                 240

Ser Leu Gly Gly Gly Ser Gly Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
```

```
                275                 280                 285
Lys Val Asp Asn Ala Leu Gln Ser Gly Asn Ser Gln Glu Ser Val Thr
        290                 295                 300
Glu Gln Asp Ser Lys Asp Ser Thr Tyr Ser Leu Ser Ser Thr Leu Thr
305                 310                 315                 320
Leu Ser Lys Ala Asp Tyr Glu Lys His Lys Val Tyr Ala Cys Glu Val
                325                 330                 335
Thr His Gln Gly Leu Ser Ser Pro Val Thr Lys Ser Phe Asn Arg Gly
        340                 345                 350
Glu Cys

<210> SEQ ID NO 114
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 114

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Tyr
            20                  25                  30
Leu Ala Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Arg Tyr Asn Arg Ala Pro Tyr
                85                  90                  95
Thr Phe Gly Gln Gly Thr Lys Val Glu Ile Lys Gly Gly Ser Gly
            100                 105                 110
Gly Gly Gly Gln Val Gln Leu Val Gln Ser Gly Ala Glu Val Lys Lys
        115                 120                 125
Pro Gly Ser Ser Val Lys Val Ser Cys Lys Ala Ser Gly Tyr Thr Phe
    130                 135                 140
Thr Asp Gln Thr Ile His Trp Met Arg Gln Ala Pro Gly Gln Gly Leu
145                 150                 155                 160
Glu Trp Ile Gly Tyr Ile Tyr Pro Arg Asp Asp Ser Pro Lys Tyr Asn
                165                 170                 175
Glu Asn Phe Lys Gly Lys Val Thr Ile Thr Ala Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Ala Ile Pro Asp Arg Ser Gly Tyr Ala Trp Phe Ile Tyr
    210                 215                 220
Trp Gly Gln Gly Thr Leu Val Thr Val Ser Ser Leu Gly Gly Gly Ser
225                 230                 235                 240
Gly Ala Ser Thr Lys Gly Pro Ser Val Phe Pro Leu Ala Pro Ser Ser
                245                 250                 255
Lys Ser Thr Ser Gly Gly Thr Ala Ala Leu Gly Cys Leu Val Lys Asp
            260                 265                 270
Tyr Phe Pro Glu Pro Val Thr Val Ser Trp Asn Ser Gly Ala Leu Thr
        275                 280                 285
```

```
Ser Gly Val His Thr Phe Pro Ala Val Leu Gln Ser Ser Gly Leu Tyr
        290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
            325                 330                 335

Lys Arg Val Glu Pro Lys Ser Cys Asp Lys Thr His Thr Cys Pro Pro
        340                 345                 350

Cys Pro Ala Pro Glu Leu Leu Gly Gly Pro Ser Val Phe Leu Phe Pro
    355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
            405                 410                 415

Glu Glu Gln Tyr Asn Ser Thr Tyr Arg Val Val Ser Val Leu Thr Val
        420                 425                 430

Leu His Gln Asp Trp Leu Asn Gly Lys Glu Tyr Lys Cys Lys Val Ser
    435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
        500                 505                 510

Asn Asn Tyr Lys Thr Thr Pro Pro Val Leu Asp Ser Asp Gly Ser Phe
    515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
            565                 570

<210> SEQ ID NO 115
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80
```

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 116
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

```
Thr Phe Gly Gln Gly Thr Lys Val Glu Ile Lys Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
            130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Cys Ser
            245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
            275                 280                 285

Ser Gly Val His Thr Phe Pro Ala Val Leu Gln Ser Ser Gly Leu Tyr
            290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
            355                 360                 365

Lys Asp Thr Leu Met Ile Ser Arg Thr Pro Glu Val Thr Cys Val Val
            370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Gly
            435                 440                 445

Leu Pro Ser Ser Ile Glu Lys Thr Ile Ser Lys Ala Lys Gly Gln Pro
            450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510
```

Lys Thr Thr Pro Pro Val Leu Asp Ser Asp Gly Ser Phe Leu Tyr
            515                 520                 525

Ser Arg Leu Thr Val Asp Lys Ser Arg Trp Gln Glu Gly Asn Val Phe
530                 535                 540

Ser Cys Ser Val Met His Glu Ala Leu His Asn His Tyr Thr Gln Lys
545                 550                 555                 560

Ser Leu Ser Leu Ser Leu Gly
                565

<210> SEQ ID NO 117
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

```
Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
            325                 330                 335

Ser Ser Pro Val Thr Lys Ser Phe Asn Arg Gly Glu Cys
        340                 345
```

<210> SEQ ID NO 118
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
290                 295                 300

Ser Leu Ser Ser Val Val Thr Val Pro Ser Ser Ser Leu Gly Thr Lys
305                 310                 315                 320
```

Thr Tyr Thr Cys Asn Val Asp His Lys Pro Ser Asn Thr Lys Val Asp
            325                 330                 335

Lys Arg Val Glu Ser Lys Tyr Gly Pro Pro Cys Pro Pro Cys Pro Ala
        340                 345                 350

Pro Glu Phe Leu Gly Gly Pro Ser Val Phe Leu Phe Pro Pro Lys Pro
        355                 360                 365

Lys Asp Thr Leu Tyr Ile Thr Arg Glu Pro Glu Val Thr Cys Val Val
370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
            405                 410                 415

Phe Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Gly
        435                 440                 445

Leu Pro Ser Ser Ile Glu Lys Thr Ile Ser Lys Ala Lys Gly Gln Pro
        450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
            485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
        530                 535                 540

Ser Cys Ser Val Met His Glu Ala Leu His Asn His Tyr Thr Gln Lys
545                 550                 555                 560

Ser Leu Ser Leu Ser Leu Gly
            565

<210> SEQ ID NO 119
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
            85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Leu Val Gln
            115                 120                 125

Pro Gly Arg Ser Leu Arg Leu Ser Cys Ala Ala Ser Gly Phe Thr Phe
        130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 120
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

```
Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Phe Asn Arg Gly Glu
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
            340                 345                 350

Cys Pro Ala Pro Glu Ala Ala Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
```

```
                545                 550                 555                 560
Thr Gln Lys Ser Leu Ser Leu Ser Pro Gly
                565                 570

<210> SEQ ID NO 121
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
```

-continued

```
                340                 345
```

<210> SEQ ID NO 122
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Phe Asn Arg Gly Glu
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
```

```
                355                 360                 365
Pro Lys Pro Lys Asp Thr Leu Met Ile Ser Arg Thr Pro Glu Val Thr
            370                 375                 380
Cys Val Val Asp Val Ser His Glu Asp Pro Glu Val Lys Phe Asn
385                 390                 395                 400
Trp Tyr Val Asp Gly Val Glu Val His Asn Ala Lys Thr Lys Pro Arg
                405                 410                 415
Glu Glu Gln Tyr Asn Ser Thr Tyr Arg Val Val Ser Val Leu Thr Val
            420                 425                 430
Leu His Gln Asp Trp Leu Asn Gly Lys Glu Tyr Lys Cys Lys Val Ser
                435                 440                 445
Asn Lys Ala Leu Pro Ala Pro Ile Glu Lys Thr Ile Ser Lys Ala Lys
            450                 455                 460
Gly Gln Pro Arg Glu Pro Gln Val Tyr Thr Leu Pro Pro Ser Arg Glu
465                 470                 475                 480
Glu Met Thr Lys Asn Gln Val Ser Leu Thr Cys Leu Val Lys Gly Phe
                485                 490                 495
Tyr Pro Ser Asp Ile Ala Val Glu Trp Glu Ser Asn Gly Gln Pro Glu
            500                 505                 510
Asn Asn Tyr Lys Thr Thr Pro Pro Val Leu Asp Ser Asp Gly Ser Phe
                515                 520                 525
Phe Leu Tyr Ser Lys Leu Thr Val Asp Lys Ser Arg Trp Gln Gln Gly
            530                 535                 540
Asn Val Phe Ser Cys Ser Val Met His Glu Ala Leu His Asn His Tyr
545                 550                 555                 560
Thr Gln Lys Ser Leu Ser Leu Ser Pro Gly
                565                 570

<210> SEQ ID NO 123
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 123

Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Gly Ser Gly
            100                 105                 110
Gly Gly Gly Glu Val Gln Leu Val Glu Ser Gly Gly Leu Val Gln
        115                 120                 125
Pro Gly Arg Ser Leu Arg Leu Ser Cys Ala Ala Ser Gly Phe Thr Phe
    130                 135                 140
Asp Asp Tyr Ala Met His Trp Val Arg Gln Ala Pro Gly Lys Gly Leu
```

```
            145                 150                 155                 160
    Glu Trp Val Ser Ala Ile Thr Trp Asn Ser Gly His Ile Asp Tyr Ala
                    165                 170                 175

Asp Ser Val Glu Gly Arg Phe Thr Ile Ser Arg Asp Asn Ala Lys Asn
                180                 185                 190

Ser Leu Tyr Leu Gln Met Asn Ser Leu Arg Ala Glu Asp Thr Ala Val
                    195                 200                 205

Tyr Tyr Cys Ala Lys Val Ser Tyr Leu Ser Thr Ala Ser Ser Leu Asp
                210                 215                 220

Tyr Trp Gly Gln Gly Thr Leu Val Thr Val Ser Ser Val Glu Pro Lys
    225                 230                 235                 240

Ser Ser Arg Thr Val Ala Ala Pro Ser Val Phe Ile Phe Pro Pro Ser
                        245                 250                 255

Asp Glu Gln Leu Lys Ser Gly Thr Ala Ser Val Val Cys Leu Leu Asn
                    260                 265                 270

Asn Phe Tyr Pro Arg Glu Ala Lys Val Gln Trp Lys Val Asp Asn Ala
                275                 280                 285

Leu Gln Ser Gly Asn Ser Gln Glu Ser Val Thr Glu Gln Asp Ser Lys
                290                 295                 300

Asp Ser Thr Tyr Ser Leu Ser Ser Thr Leu Thr Leu Ser Lys Ala Asp
    305                 310                 315                 320

Tyr Glu Lys His Lys Val Tyr Ala Cys Glu Val Thr His Gln Gly Leu
                        325                 330                 335

Ser Ser Pro Val Thr Lys Ser Phe Asn Arg Gly Glu Cys
                    340                 345

<210> SEQ ID NO 124
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 124

Asp Ile Gln Met Thr Gln Ser Pro Ser Ser Leu Ser Ala Ser Val Gly
    1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
                    35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
    65                  70                  75                  80

Glu Asp Val Ala Thr Tyr Tyr Cys Gln Arg Tyr Asn Arg Ala Pro Tyr
                    85                  90                  95

Thr Phe Gly Gln Gly Thr Lys Val Glu Ile Lys Gly Gly Gly Ser Gly
                100                 105                 110

Gly Gly Gly Gln Val Gln Leu Val Gln Ser Gly Ala Glu Val Lys Lys
                115                 120                 125

Pro Gly Ser Ser Val Lys Val Ser Cys Lys Ala Ser Gly Tyr Thr Phe
                    130                 135                 140

Thr Asp Gln Thr Ile His Trp Met Arg Gln Ala Pro Gly Gln Gly Leu
    145                 150                 155                 160

Glu Trp Ile Gly Tyr Ile Tyr Pro Arg Asp Asp Ser Pro Lys Tyr Asn
```

```
                165                 170                 175
Glu Asn Phe Lys Gly Lys Val Thr Ile Thr Ala Asp Lys Ser Thr Ser
                180                 185                 190

Thr Ala Tyr Met Glu Leu Ser Ser Leu Arg Ser Glu Asp Thr Ala Val
                195                 200                 205

Tyr Tyr Cys Ala Ile Pro Asp Arg Ser Gly Tyr Ala Trp Phe Ile Tyr
            210                 215                 220

Trp Gly Gln Gly Thr Leu Val Thr Val Ser Ser Phe Asn Arg Gly Glu
225                 230                 235                 240

Ser Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
                260                 265                 270

Tyr Phe Pro Glu Pro Val Thr Val Ser Trp Asn Ser Gly Ala Leu Thr
            275                 280                 285

Ser Gly Val His Thr Phe Pro Ala Val Leu Gln Ser Ser Gly Leu Tyr
        290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
                340                 345                 350

Pro Glu Phe Leu Gly Gly Pro Ser Val Phe Leu Phe Pro Pro Lys Pro
            355                 360                 365

Lys Asp Thr Leu Met Ile Ser Arg Thr Pro Glu Val Thr Cys Val Val
        370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Tyr Arg Val Val Ser Val Leu Thr Val Leu His Gln
                420                 425                 430

Asp Trp Leu Asn Gly Lys Glu Tyr Lys Cys Lys Val Ser Asn Lys Gly
            435                 440                 445

Leu Pro Ser Ser Ile Glu Lys Thr Ile Ser Lys Ala Lys Gly Gln Pro
        450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
        530                 535                 540

Ser Cys Ser Val Met His Glu Ala Leu His Asn His Tyr Thr Gln Lys
545                 550                 555                 560

Ser Leu Ser Leu Ser Leu Gly
            565

<210> SEQ ID NO 125
```

<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Leu Val Gln
        115                 120                 125

Pro Gly Arg Ser Leu Arg Leu Ser Cys Ala Ala Ser Gly Phe Thr Phe
130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 126
<211> LENGTH: 567
<212> TYPE: PRT
<213> ORGANISM: Artificial Sequence

```
<220> FEATURE:
<223> OTHER INFORMATION: Synthetic Polypeptide

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Phe Asn Arg Gly Glu
225                 230                 235                 240

Ser Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
        355                 360                 365

Lys Asp Thr Leu Tyr Ile Thr Arg Glu Pro Glu Val Thr Cys Val Val
    370                 375                 380

Val Asp Val Ser Gln Glu Asp Pro Glu Val Gln Phe Asn Trp Tyr Val
385                 390                 395                 400
```

Asp Gly Val Glu Val His Asn Ala Lys Thr Lys Pro Arg Glu Glu Gln
            405                 410                 415

Phe Asn Ser Thr Tyr Arg Val Val Ser Val Leu Thr Val Leu His Gln
        420                 425                 430

Asp Trp Leu Asn Gly Lys Glu Tyr Lys Cys Lys Val Ser Asn Lys Gly
    435                 440                 445

Leu Pro Ser Ser Ile Glu Lys Thr Ile Ser Lys Ala Lys Gly Gln Pro
450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
    530                 535                 540

Ser Cys Ser Val Met His Glu Ala Leu His Asn His Tyr Thr Gln Lys
545                 550                 555                 560

Ser Leu Ser Leu Ser Leu Gly
                565

<210> SEQ ID NO 127
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

```
Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Val Glu Pro Lys
225                 230                 235                 240

Ser Ser Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
    290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345
```

<210> SEQ ID NO 128
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205
```

Tyr Tyr Cys Ala Lys Val Ser Tyr Leu Ser Thr Ala Ser Ser Leu Asp
                210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
                260                 265                 270

Asp Tyr Phe Pro Glu Pro Val Thr Val Ser Trp Asn Ser Gly Ala Leu
                275                 280                 285

Thr Ser Gly Val His Thr Phe Pro Ala Val Leu Gln Ser Ser Gly Leu
                290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
                340                 345                 350

Pro Cys Pro Ala Pro Glu Ala Ala Gly Gly Pro Ser Val Phe Leu Phe
                355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
                420                 425                 430

Val Leu His Gln Asp Trp Leu Asn Gly Lys Glu Tyr Lys Cys Lys Val
                435                 440                 445

Ser Asn Lys Ala Leu Pro Ala Pro Ile Glu Lys Thr Ile Ser Lys Ala
                450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
                515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 129
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 129

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 130
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 130

Asp Ile Gln Met Thr Gln Ser Pro Ser Ser Leu Ser Ala Ser Val Gly
1               5                   10                  15
```

-continued

```
Asp Arg Val Thr Ile Thr Cys Lys Ala Ser Arg Asp Val Ala Ile Ala
         20                  25                  30

Val Ala Trp Tyr Gln Gln Lys Pro Gly Lys Val Pro Lys Leu Leu Ile
             35                  40                  45

Tyr Trp Ala Ser Thr Arg His Thr Gly Val Pro Ser Arg Phe Ser Gly
 50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                 85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
            115                 120                 125

Pro Gly Arg Ser Leu Arg Leu Ser Cys Ala Ala Ser Gly Phe Thr Phe
130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
            195                 200                 205

Tyr Tyr Cys Ala Lys Val Ser Tyr Leu Ser Thr Ala Ser Ser Leu Asp
210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Leu Leu Gly Gly Pro Ser Val Phe Leu Phe
            355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430
```

Val Leu His Gln Asp Trp Leu Asn Gly Lys Glu Tyr Lys Cys Lys Val
            435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
            485                 490                 495

Phe Tyr Pro Ser Asp Ile Ala Val Glu Trp Glu Ser Asn Gly Gln Pro
        500                 505                 510

Glu Asn Asn Tyr Lys Thr Thr Pro Pro Val Leu Asp Ser Asp Gly Ser
    515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 131
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly Ser
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

```
Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
            245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
            275                 280                 285

Gln Ser Gly Asn Ser Gln Glu Ser Val Thr Glu Gln Asp Ser Lys Asp
            290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
            325                 330                 335

Ser Pro Val Thr Lys Ser Phe Asn Arg Gly Glu Cys
            340                 345

<210> SEQ ID NO 132
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
            85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
            165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Leu Gly Gly Gly
225                 230                 235                 240
```

```
Ser Gly Ala Ser Thr Lys Gly Pro Ser Val Phe Pro Leu Ala Pro Cys
            245                 250                 255

Ser Arg Ser Thr Ser Glu Ser Thr Ala Ala Leu Gly Cys Leu Val Lys
        260                 265                 270

Asp Tyr Phe Pro Glu Pro Val Thr Val Ser Trp Asn Ser Gly Ala Leu
    275                 280                 285

Thr Ser Gly Val His Thr Phe Pro Ala Val Leu Gln Ser Ser Gly Leu
290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Pro Cys Pro
            340                 345                 350

Ala Pro Glu Phe Leu Gly Gly Pro Ser Val Phe Leu Phe Pro Pro Lys
        355                 360                 365

Pro Lys Asp Thr Leu Met Ile Ser Arg Thr Pro Glu Val Thr Cys Val
    370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Gly Leu Pro Ser Ser Ile Glu Lys Thr Ile Ser Lys Ala Lys Gly Gln
    450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Arg Leu Thr Val Asp Lys Ser Arg Trp Gln Glu Gly Asn Val
    530                 535                 540

Phe Ser Cys Ser Val Met His Glu Ala Leu His Asn His Tyr Thr Gln
545                 550                 555                 560

Lys Ser Leu Ser Leu Ser Leu Gly
                565
```

<210> SEQ ID NO 133
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30
```

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 134
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

-continued

```
Tyr Trp Ala Ser Thr Arg His Thr Gly Val Pro Ser Arg Phe Ser Gly
 50                  55                  60
Ser Gly Ser Arg Thr Asp Phe Thr Leu Thr Ile Ser Ser Leu Gln Pro
 65                  70                  75                  80
Glu Asp Val Ala Asp Tyr Phe Cys His Gln Tyr Ser Ser Tyr Pro Phe
                 85                  90                  95
Thr Phe Gly Ser Gly Thr Lys Leu Glu Ile Lys Gly Gly Gly Ser Gly
            100                 105                 110
Gly Gly Gly Glu Val Gln Leu Val Glu Ser Gly Gly Gly Leu Val Gln
        115                 120                 125
Pro Gly Arg Ser Leu Arg Leu Ser Cys Ala Ala Ser Gly Phe Thr Phe
130                 135                 140
Asp Asp Tyr Ala Met His Trp Val Arg Gln Ala Pro Gly Lys Gly Leu
145                 150                 155                 160
Glu Trp Val Ser Ala Ile Thr Trp Asn Ser Gly His Ile Asp Tyr Ala
                165                 170                 175
Asp Ser Val Glu Gly Arg Phe Thr Ile Ser Arg Asp Asn Ala Lys Asn
            180                 185                 190
Ser Leu Tyr Leu Gln Met Asn Ser Leu Arg Ala Glu Asp Thr Ala Val
        195                 200                 205
Tyr Tyr Cys Ala Lys Val Ser Tyr Leu Ser Thr Ala Ser Ser Leu Asp
210                 215                 220
Tyr Trp Gly Gln Gly Thr Leu Val Thr Val Ser Ser Leu Gly Gly Gly
225                 230                 235                 240
Ser Gly Ala Ser Thr Lys Gly Pro Ser Val Phe Pro Leu Ala Pro Cys
                245                 250                 255
Ser Arg Ser Thr Ser Glu Ser Thr Ala Ala Leu Gly Cys Leu Val Lys
            260                 265                 270
Asp Tyr Phe Pro Glu Pro Val Thr Val Ser Trp Asn Ser Gly Ala Leu
        275                 280                 285
Thr Ser Gly Val His Thr Phe Pro Ala Val Leu Gln Ser Ser Gly Leu
290                 295                 300
Tyr Ser Leu Ser Ser Val Val Thr Val Pro Ser Ser Ser Leu Gly Thr
305                 310                 315                 320
Lys Thr Tyr Thr Cys Asn Val Asp His Lys Pro Ser Asn Thr Lys Val
                325                 330                 335
Asp Lys Arg Val Glu Ser Lys Tyr Gly Pro Pro Cys Pro Pro Cys Pro
            340                 345                 350
Ala Pro Glu Phe Leu Gly Gly Pro Ser Val Phe Leu Phe Pro Pro Lys
        355                 360                 365
Pro Lys Asp Thr Leu Tyr Ile Thr Arg Glu Pro Glu Val Thr Cys Val
370                 375                 380
Val Val Asp Val Ser Gln Glu Asp Pro Glu Val Gln Phe Asn Trp Tyr
385                 390                 395                 400
Val Asp Gly Val Glu Val His Asn Ala Lys Thr Lys Pro Arg Glu Glu
                405                 410                 415
Gln Phe Asn Ser Thr Tyr Arg Val Val Ser Val Leu Thr Val Leu His
            420                 425                 430
Gln Asp Trp Leu Asn Gly Lys Glu Tyr Lys Cys Lys Val Ser Asn Lys
        435                 440                 445
Gly Leu Pro Ser Ser Ile Glu Lys Thr Ile Ser Lys Ala Lys Gly Gln
450                 455                 460
Pro Arg Glu Pro Gln Val Tyr Thr Leu Pro Pro Ser Gln Glu Glu Met
```

```
            465                 470                 475                 480
Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
                500                 505                 510

Tyr Lys Thr Thr Pro Pro Val Leu Asp Ser Asp Gly Ser Phe Phe Leu
                515                 520                 525

Tyr Ser Arg Leu Thr Val Asp Lys Ser Arg Trp Gln Glu Gly Asn Val
                530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 135
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
                100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
            130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
        210                 215                 220

Trp Gly Gln Gly Thr Leu Val Thr Val Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
```

```
              260                 265                 270
Phe Tyr Pro Arg Glu Ala Lys Val Gln Trp Lys Val Asp Asn Ala Leu
            275                 280                 285

Gln Ser Gly Asn Ser Gln Glu Ser Val Thr Glu Gln Asp Ser Lys Asp
        290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 136
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 136

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
```

```
                275                 280                 285
Thr Ser Gly Val His Thr Phe Pro Ala Val Leu Gln Ser Ser Gly Leu
    290                 295                 300
Tyr Ser Leu Ser Ser Val Val Thr Val Pro Ser Ser Ser Leu Gly Thr
305                 310                 315                 320
Gln Thr Tyr Ile Cys Asn Val Asn His Lys Pro Ser Asn Thr Lys Val
                325                 330                 335
Asp Lys Arg Val Glu Pro Lys Ser Cys Asp Lys Thr His Thr Cys Pro
            340                 345                 350
Pro Cys Pro Ala Pro Glu Leu Leu Gly Gly Pro Ser Val Phe Leu Phe
        355                 360                 365
Pro Pro Lys Pro Lys Asp Thr Leu Met Ile Ser Arg Thr Pro Glu Val
    370                 375                 380
Thr Cys Val Val Val Asp Val Ser His Glu Asp Pro Glu Val Lys Phe
385                 390                 395                 400
Asn Trp Tyr Val Asp Gly Val Glu Val His Asn Ala Lys Thr Lys Pro
                405                 410                 415
Arg Glu Glu Gln Tyr Asn Ser Thr Tyr Arg Val Val Ser Val Leu Thr
            420                 425                 430
Val Leu His Gln Asp Trp Leu Asn Gly Lys Glu Tyr Lys Cys Lys Val
        435                 440                 445
Ser Asn Lys Ala Leu Pro Ala Pro Ile Glu Lys Thr Ile Ser Lys Ala
    450                 455                 460
Lys Gly Gln Pro Arg Glu Pro Gln Val Tyr Thr Leu Pro Pro Ser Arg
465                 470                 475                 480
Glu Glu Met Thr Lys Asn Gln Val Ser Leu Thr Cys Leu Val Lys Gly
                485                 490                 495
Phe Tyr Pro Ser Asp Ile Ala Val Glu Trp Glu Ser Asn Gly Gln Pro
            500                 505                 510
Glu Asn Asn Tyr Lys Thr Thr Pro Pro Val Leu Asp Ser Asp Gly Ser
        515                 520                 525
Phe Phe Leu Tyr Ser Lys Leu Thr Val Asp Lys Ser Arg Trp Gln Gln
    530                 535                 540
Gly Asn Val Phe Ser Cys Ser Val Met His Glu Ala Leu His Asn His
545                 550                 555                 560
Tyr Thr Gln Lys Ser Leu Ser Leu Ser Pro Gly
                565                 570

<210> SEQ ID NO 137
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 137

Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
```

```
                65                  70                  75                  80
        Glu Asp Val Ala Asp Tyr Phe Cys His Gln Tyr Ser Ser Tyr Pro Phe
                            85                  90                  95
        Thr Phe Gly Ser Gly Thr Lys Leu Glu Ile Lys Gly Gly Gly Ser Gly
                        100                 105                 110
        Gly Gly Gly Gln Val Gln Leu Val Glu Ser Gly Gly Val Val Gln
                    115                 120                 125
        Pro Gly Arg Ser Leu Arg Leu Ser Cys Ala Ala Ser Gly Phe Ile Phe
                130                 135                 140
        Ser Ser Tyr Ala Met His Trp Val Arg Gln Ala Pro Gly Asn Gly Leu
        145                 150                 155                 160
        Glu Trp Val Ala Phe Met Ser Tyr Asp Gly Ser Asn Lys Lys Tyr Ala
                            165                 170                 175
        Asp Ser Val Lys Gly Arg Phe Thr Ile Ser Arg Asp Asn Ser Lys Asn
                        180                 185                 190
        Thr Leu Tyr Leu Gln Met Asn Ser Leu Arg Ala Glu Asp Thr Ala Val
                    195                 200                 205
        Tyr Tyr Cys Ala Arg Asp Arg Gly Ile Ala Ala Gly Gly Asn Tyr Tyr
                210                 215                 220
        Tyr Tyr Gly Met Asp Val Trp Gly Gln Gly Thr Thr Val Thr Val Ser
        225                 230                 235                 240
        Ser Leu Gly Gly Gly Ser Gly Arg Thr Val Ala Ala Pro Ser Val Phe
                            245                 250                 255
        Ile Phe Pro Pro Ser Asp Glu Gln Leu Lys Ser Gly Thr Ala Ser Val
                        260                 265                 270
        Val Cys Leu Leu Asn Asn Phe Tyr Pro Arg Glu Ala Lys Val Gln Trp
                    275                 280                 285
        Lys Val Asp Asn Ala Leu Gln Ser Gly Asn Ser Gln Glu Ser Val Thr
                290                 295                 300
        Glu Gln Asp Ser Lys Asp Ser Thr Tyr Ser Leu Ser Ser Thr Leu Thr
        305                 310                 315                 320
        Leu Ser Lys Ala Asp Tyr Glu Lys His Lys Val Tyr Ala Cys Glu Val
                            325                 330                 335
        Thr His Gln Gly Leu Ser Ser Pro Val Thr Lys Ser Phe Asn Arg Gly
                        340                 345                 350
        Glu Cys

<210> SEQ ID NO 138
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 138

Asp Ile Gln Met Thr Gln Ser Pro Ser Ser Leu Ser Ala Ser Val Gly
        1               5                   10                  15
        Asp Arg Val Thr Ile Thr Cys Lys Ala Ser Arg Asp Val Ala Ile Ala
                            20                  25                  30
        Val Ala Trp Tyr Gln Gln Lys Pro Gly Lys Val Pro Lys Leu Leu Ile
                        35                  40                  45
        Tyr Trp Ala Ser Thr Arg His Thr Gly Val Pro Ser Arg Phe Ser Gly
                    50                  55                  60
        Ser Gly Ser Arg Thr Asp Phe Thr Leu Thr Ile Ser Ser Leu Gln Pro
        65                  70                  75                  80
```

```
Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Ser Gly
            100                 105                 110

Gly Gly Gly Glu Val Gln Leu Val Glu Ser Gly Gly Gly Leu Val Gln
            115                 120                 125

Pro Gly Arg Ser Leu Arg Leu Ser Cys Ala Ala Ser Gly Phe Thr Phe
    130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
            195                 200                 205

Tyr Tyr Cys Ala Lys Val Ser Tyr Leu Ser Thr Ala Ser Ser Leu Asp
    210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
    275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Leu Leu Gly Gly Pro Ser Val Phe Leu Phe
    355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
    435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495
```

```
Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 139
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly Ser
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Val Glu Pro Lys Ser
225                 230                 235                 240

Ser Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285
```

```
Gln Ser Gly Asn Ser Gln Glu Ser Val Thr Glu Gln Asp Ser Lys Asp
        290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 140
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Arg Ser Leu Arg Leu Ser Cys Ala Ala Ser Gly Phe Thr Phe
130                 135                 140

Asp Asp Tyr Ala Met His Trp Val Arg Gln Ala Pro Gly Lys Gly Leu
145                 150                 155                 160

Glu Trp Val Ser Ala Ile Thr Trp Asn Ser Gly His Ile Asp Tyr Ala
                165                 170                 175

Asp Ser Val Glu Gly Arg Phe Thr Ile Ser Arg Asp Asn Ala Lys Asn
            180                 185                 190

Ser Leu Tyr Leu Gln Met Asn Ser Leu Arg Ala Glu Asp Thr Ala Val
        195                 200                 205

Tyr Tyr Cys Ala Lys Val Ser Tyr Leu Ser Thr Ala Ser Ser Leu Asp
210                 215                 220

Tyr Trp Gly Gln Gly Thr Leu Val Thr Val Ser Ser Phe Asn Arg Gly
225                 230                 235                 240

Glu Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
290                 295                 300
```

```
Tyr Ser Leu Ser Ser Val Thr Val Pro Ser Ser Leu Gly Thr
305                 310                 315                 320

Lys Thr Tyr Thr Cys Asn Val Asp His Lys Pro Ser Asn Thr Lys Val
            325                 330                 335

Asp Lys Arg Val Glu Ser Lys Tyr Gly Pro Pro Cys Pro Pro Cys Pro
        340                 345                 350

Ala Pro Glu Phe Leu Gly Gly Pro Ser Val Phe Leu Phe Pro Pro Lys
    355                 360                 365

Pro Lys Asp Thr Leu Met Ile Ser Arg Thr Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
                420                 425                 430

Gln Asp Trp Leu Asn Gly Lys Glu Tyr Lys Cys Lys Val Ser Asn Lys
            435                 440                 445

Gly Leu Pro Ser Ser Ile Glu Lys Thr Ile Ser Lys Ala Lys Gly Gln
450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
            515                 520                 525

Tyr Ser Arg Leu Thr Val Asp Lys Ser Arg Trp Gln Glu Gly Asn Val
530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 141
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Arg Tyr Asn Arg Ala Pro Tyr
                85                  90                  95
```

Thr Phe Gly Gln Gly Thr Lys Val Glu Ile Lys Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
        130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Val Glu Pro Lys Ser
225                 230                 235                 240

Ser Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 142
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

```
Gly Gly Gly Glu Val Gln Leu Val Glu Ser Gly Gly Leu Val Gln
            115                 120                 125
Pro Gly Arg Ser Leu Arg Leu Ser Cys Ala Ala Ser Gly Phe Thr Phe
130                 135                 140
Asp Asp Tyr Ala Met His Trp Val Arg Gln Ala Pro Gly Lys Gly Leu
145                 150                 155                 160
Glu Trp Val Ser Ala Ile Thr Trp Asn Ser Gly His Ile Asp Tyr Ala
                165                 170                 175
Asp Ser Val Glu Gly Arg Phe Thr Ile Ser Arg Asp Asn Ala Lys Asn
            180                 185                 190
Ser Leu Tyr Leu Gln Met Asn Ser Leu Arg Ala Glu Asp Thr Ala Val
        195                 200                 205
Tyr Tyr Cys Ala Lys Val Ser Tyr Leu Ser Thr Ala Ser Ser Leu Asp
    210                 215                 220
Tyr Trp Gly Gln Gly Thr Leu Val Thr Val Ser Ser Phe Asn Arg Gly
225                 230                 235                 240
Glu Ser Ala Ser Thr Lys Gly Pro Ser Val Phe Pro Leu Ala Pro Cys
                245                 250                 255
Ser Arg Ser Thr Ser Glu Ser Thr Ala Ala Leu Gly Cys Leu Val Lys
            260                 265                 270
Asp Tyr Phe Pro Glu Pro Val Thr Val Ser Trp Asn Ser Gly Ala Leu
        275                 280                 285
Thr Ser Gly Val His Thr Phe Pro Ala Val Leu Gln Ser Ser Gly Leu
    290                 295                 300
Tyr Ser Leu Ser Ser Val Val Thr Val Pro Ser Ser Ser Leu Gly Thr
305                 310                 315                 320
Lys Thr Tyr Thr Cys Asn Val Asp His Lys Pro Ser Asn Thr Lys Val
                325                 330                 335
Asp Lys Arg Val Glu Ser Lys Tyr Gly Pro Pro Cys Pro Pro Cys Pro
            340                 345                 350
Ala Pro Glu Phe Leu Gly Gly Pro Ser Val Phe Leu Phe Pro Pro Lys
        355                 360                 365
Pro Lys Asp Thr Leu Tyr Ile Thr Arg Glu Pro Glu Val Thr Cys Val
    370                 375                 380
Val Val Asp Val Ser Gln Glu Asp Pro Glu Val Gln Phe Asn Trp Tyr
385                 390                 395                 400
Val Asp Gly Val Glu Val His Asn Ala Lys Thr Lys Pro Arg Glu Glu
                405                 410                 415
Gln Phe Asn Ser Thr Tyr Arg Val Val Ser Val Leu Thr Val Leu His
            420                 425                 430
Gln Asp Trp Leu Asn Gly Lys Glu Tyr Lys Cys Lys Val Ser Asn Lys
        435                 440                 445
Gly Leu Pro Ser Ser Ile Glu Lys Thr Ile Ser Lys Ala Lys Gly Gln
    450                 455                 460
Pro Arg Glu Pro Gln Val Tyr Thr Leu Pro Pro Ser Gln Glu Glu Met
465                 470                 475                 480
Thr Lys Asn Gln Val Ser Leu Thr Cys Leu Val Lys Gly Phe Tyr Pro
                485                 490                 495
Ser Asp Ile Ala Val Glu Trp Glu Ser Asn Gly Gln Pro Glu Asn Asn
            500                 505                 510
Tyr Lys Thr Thr Pro Pro Val Leu Asp Ser Asp Gly Ser Phe Phe Leu
        515                 520                 525
Tyr Ser Arg Leu Thr Val Asp Lys Ser Arg Trp Gln Glu Gly Asn Val
```

```
                530                 535                 540
Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 143
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Val Glu Pro Lys Ser
225                 230                 235                 240

Ser Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
```

```
                        325                 330                 335
Ser Pro Val Thr Lys Ser Phe Asn Arg Gly Glu Cys
                340                 345

<210> SEQ ID NO 144
<211> LENGTH: 233
<212> TYPE: PRT
<213> ORGANISM: Homo sapiens

<400> SEQUENCE: 144

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 145
<211> LENGTH: 189
<212> TYPE: PRT
<213> ORGANISM: Homo sapiens

<400> SEQUENCE: 145

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
```

```
                65                  70                  75                  80
Gly Leu Arg Asp Asn Ser Gln Phe Cys Leu Gln Arg Ile His Gln Gly
                    85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 146
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 146

```
Asp Tyr Ala Met His
1               5
```

<210> SEQ ID NO 147
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 147

```
Ala Ile Thr Trp Asn Ser Gly His Ile Asp Tyr Ala Asp Ser Val Glu
1               5                   10                  15

Gly
```

<210> SEQ ID NO 148
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 148

```
Val Ser Tyr Leu Ser Thr Ala Ser Ser Leu Asp Tyr
1               5                   10
```

<210> SEQ ID NO 149
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 149

```
Arg Ala Ser Gln Gly Ile Arg Asn Tyr Leu Ala
1               5                   10
```

<210> SEQ ID NO 150

```
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 150

Ala Ala Ser Thr Leu Gln Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 151

Gln Arg Tyr Asn Arg Ala Pro Tyr Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 152

Ser Tyr Ala Met His
1               5

<210> SEQ ID NO 153
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 153

Phe Met Ser Tyr Asp Gly Ser Asn Lys Lys Tyr Ala Asp Ser Val Lys
1               5                   10                  15

Gly

<210> SEQ ID NO 154
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 154

Asn Tyr Tyr Tyr Tyr Gly Met Asp Val
1               5

<210> SEQ ID NO 155
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 155

Arg Ala Ser Gln Ser Val Tyr Ser Tyr Leu Ala
1               5                   10
```

```
<210> SEQ ID NO 156
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 156

Asp Ala Ser Asn Arg Ala Thr
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 157

Gln Gln Arg Ser Asn Trp Pro Pro Phe Thr
1               5                   10

<210> SEQ ID NO 158
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 158

Asp Gln Thr Ile His
1               5

<210> SEQ ID NO 159
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 159

Tyr Ile Tyr Pro Arg Asp Asp Ser Pro Lys Tyr Asn Glu Asn Phe Lys
1               5                   10                  15

Gly

<210> SEQ ID NO 160
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 160

Pro Asp Arg Ser Gly Tyr Ala Trp Phe Ile Tyr
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 161

Lys Ala Ser Arg Asp Val Ala Ile Ala Val Ala
1               5                   10
```

```
<210> SEQ ID NO 162
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 162

Trp Ala Ser Thr Arg His Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 163

His Gln Tyr Ser Ser Tyr Pro Phe Thr
1               5
```